United States Patent
Lee et al.

(10) Patent No.: US 12,201,017 B2
(45) Date of Patent: Jan. 14, 2025

(54) LIGHT-EMITTING DEVICE AND ELECTRONIC APPARATUS INCLUDING THE LIGHT-EMITTING DEVICE

(71) Applicant: Samsung Display Co., Ltd., Yongin-si (KR)

(72) Inventors: Yoonkyoo Lee, Yongin-si (KR); Jinwon Sun, Yongin-si (KR); Jungsub Lee, Yongin-si (KR)

(73) Assignee: SAMSUNG DISPLAY CO., LTD., Yongin-si (KR)

(*) Notice: Subject to any disclaimer, the term of this patent is extended or adjusted under 35 U.S.C. 154(b) by 728 days.

(21) Appl. No.: 17/369,366

(22) Filed: Jul. 7, 2021

(65) Prior Publication Data
US 2022/0020939 A1    Jan. 20, 2022

(30) Foreign Application Priority Data
Jul. 17, 2020 (KR) .................. 10-2020-0089156

(51) Int. Cl.
| | |
|---|---|
| H10K 50/11 | (2023.01) |
| C07D 209/86 | (2006.01) |
| C07F 7/08 | (2006.01) |
| C09K 11/06 | (2006.01) |
| H10K 85/40 | (2023.01) |
| H10K 85/60 | (2023.01) |
| H10K 50/844 | (2023.01) |
| H10K 59/123 | (2023.01) |
| H10K 101/00 | (2023.01) |
| H10K 101/10 | (2023.01) |

(52) U.S. Cl.
CPC ........... H10K 85/40 (2023.02); C07D 209/86 (2013.01); C07F 7/0812 (2013.01); C09K 11/06 (2013.01); H10K 85/6572 (2023.02); C07B 2200/05 (2013.01); C09K 2211/1018 (2013.01); H10K 50/11 (2023.02); H10K 50/844 (2023.02); H10K 59/123 (2023.02); H10K 85/654 (2023.02); H10K 2101/10 (2023.02); H10K 2101/90 (2023.02)

(58) Field of Classification Search
None
See application file for complete search history.

(56) References Cited

U.S. PATENT DOCUMENTS

| | | | |
|---|---|---|---|
| 7,754,346 B2 | 7/2010 | Okada | |
| 9,783,564 B2 | 10/2017 | Kottas et al. | |
| 10,211,414 B2 | 2/2019 | Li et al. | |
| 10,333,077 B2 | 6/2019 | Cho et al. | |
| 2009/0128008 A1 | 5/2009 | Ise et al. | |
| 2010/0084967 A1 † | 4/2010 | Takeda | |
| 2011/0101312 A1* | 5/2011 | LeCloux | C07D 487/04 544/212 |
| 2011/0147717 A1* | 6/2011 | LeCloux | H10K 85/633 564/429 |
| 2015/0325796 A1 † | 11/2015 | Tada | |
| 2017/0117488 A1 | 4/2017 | Ahn et al. | |
| 2018/0337361 A1* | 11/2018 | Lee | H10K 85/631 |
| 2019/0036055 A1* | 1/2019 | Lin | H10K 50/18 |
| 2019/0058136 A1 | 2/2019 | MacInnis et al. | |
| 2019/0119312 A1* | 4/2019 | Chen | C07F 15/0086 |
| 2019/0189935 A1 † | 6/2019 | Beers | |
| 2019/0296254 A1* | 9/2019 | Ko | H10K 85/346 |
| 2019/0393431 A1 | 12/2019 | Layek et al. | |
| 2020/0079735 A1* | 3/2020 | Ma | H10K 85/6572 |
| 2020/0119289 A1* | 4/2020 | Lin | H10K 85/346 |
| 2020/0140471 A1* | 5/2020 | Chen | C07F 15/0086 |
| 2022/0177492 A1* | 6/2022 | Fleetham | C07B 59/002 |
| 2023/0041530 A1* | 2/2023 | Fleetham | H10K 85/631 |

FOREIGN PATENT DOCUMENTS

| | | |
|---|---|---|
| JP | 2009-231516 | 10/2009 |
| JP | 4903416 | 3/2012 |
| KR | 10-2010-0014603 | 2/2010 |
| KR | 10-2014-0144152 | 12/2014 |
| KR | 10-2015-0097703 | 8/2015 |
| KR | 10-2018-0027468 | 3/2018 |
| KR | 10-2019-0112232 | 10/2019 |
| KR | 10-2072807 | 2/2020 |
| KR | 10-2020-0034626 | 3/2020 |

OTHER PUBLICATIONS

Chun Chih Tong et al., "Enhancement of OLED Efficiencies and High-Voltage Stabilities of Light-Emitting Materials by Deuteration", J. Phys. Chem. C, Feb. 2, 2007, pp. 3490-3494, vol. 111, No. 8.

\* cited by examiner
† cited by third party

Primary Examiner — Robert S Loewe
(74) Attorney, Agent, or Firm — KILE PARK REED & HOUTTEMAN PLLC

(57) ABSTRACT

The disclosure relates to a light-emitting device including a first electrode, a second electrode facing the first electrode, and an interlayer disposed between the first electrode and the second electrode and including an emission layer. The interlayer includes a first compound represented by Formula 1 of the specification, a second compound represented by Formula 2 of the specification, and a third compound, which is a blue phosphorescent compound. The disclosure also relates to an electronic apparatus including the light-emitting device.

18 Claims, 3 Drawing Sheets

LIGHT-EMITTING DEVICE AND ELECTRONIC APPARATUS INCLUDING THE LIGHT-EMITTING DEVICE

CROSS-REFERENCE TO RELATED APPLICATION(S)

This application claims priority to and benefits of Korean Patent Application No. 10-2020-0089156 under 35 U.S.C. § 119, filed on Jul. 17, 2020 in the Korean Intellectual Property Office, the entire contents of which are incorporated herein by reference.

BACKGROUND

1. Technical Field

Embodiments relate to a light-emitting device and an electronic apparatus including the light-emitting device.

2. Description of the Related Art

Among light emitting devices, organic light-emitting devices are self-emission devices that have wide viewing angles, high contrast ratios, short response times, and excellent characteristics in terms of brightness, driving voltage, and response speed, compared to devices in the art.

Organic light-emitting devices may include a first electrode disposed on a substrate, a hole transport region, an emission layer, an electron transport region, and a second electrode sequentially stacked on the first electrode. Holes provided from the first electrode may move toward the emission layer through the hole transport region, and electrons provided from the second electrode may move toward the emission layer through the electron transport region. Carriers, such as the holes and the electrons, recombine in the emission layer to produce excitons. These excitons transition from an excited state to a ground state to thereby generate light.

SUMMARY

Embodiments relate to a light-emitting device including a compound having excellent light emission efficiency and high stability, and an electronic apparatus including the light-emitting device.

Additional aspects will be set forth in part in the description which follows and, in part, will be apparent from the description, or may be learned by practice of the embodiments of the disclosure.

According to an aspect, a light-emitting device may include a first electrode, a second electrode facing the first electrode, an interlayer disposed between the first electrode and the second electrode and including an emission layer. The interlayer may include a first compound represented by Formula 1, a second compound represented by Formula 2, and a third compound, and the third compound may be a blue phosphorescent compound.

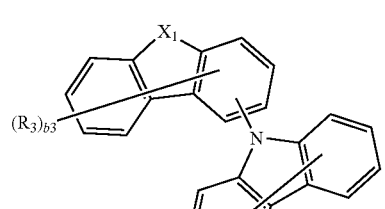

[Formula 1]

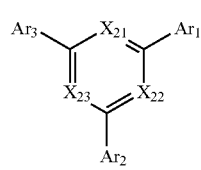

[Formula 2]

In Formula 1,
$X_1$ may be $C(R_1)(R_2)$, $Si(R_1)(R_2)$, $N-[(L_1)_{a1}-(R_1)_{b1}]$, O, or S,
$L_1$ may be a $C_4$-$C_{60}$ carbocyclic group unsubstituted or substituted with at least one $R_{10a}$ or a $C_1$-$C_{60}$ heterocyclic group unsubstituted or substituted with at least one $R_{10a}$,
a1 may be an integer from 0 to 5,
$R_1$ to $R_4$ may each independently be hydrogen, deuterium, —F, —Cl, —Br, —I, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, $-B(Q_1)(Q_2)$, $-P(Q_1)(Q_2)$, $-C(=O)(Q_1)$, or $-Si(Q_1)(Q_2)(Q_3)$,
b1 may be an integer from 0 to 10,
b3 may be an integer from 0 to 7,
b4 may be an integer from 0 to 8, and
the first compound may include at least one deuterium (D),
in Formula 2,
$X_{21}$ may be $C(R_{21})$ or N,
$X_{22}$ may be $C(R_{22})$ or N,
$X_{23}$ may be $C(R_{23})$ or N,
at least one of $X_{21}$, $X_{22}$, and $X_{23}$ may be N,
$Ar_1$ to $Ar_3$ may each independently be a $C_4$-$C_{60}$ carbocyclic group unsubstituted or substituted with at least one $R_{10a}$, a $C_1$-$C_{60}$ heterocyclic group unsubstituted or substituted with at least one $R_{10a}$, $-C(Q_1)(Q_2)(Q_3)$, or $-Si(Q_1)(Q_2)(Q_3)$,
$R_{21}$, $R_{22}$, and $R_{23}$ may each independently be the same as described in connection with $R_1$ in Formula 1
$R_{10a}$ may be
deuterium (-D), —F, —Cl, —Br, —I, a hydroxyl group, a cyano group, or a nitro group,
a $C_1$-$C_{60}$ alkyl group, a $C_2$-$C_{60}$ alkenyl group, a $C_2$-$C_{60}$ alkynyl group, or a $C_1$-$C_{60}$ alkoxy group, each unsubstituted or substituted with deuterium, —F, —Cl, —Br, —I, a hydroxyl group, a cyano group, a nitro group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, —C($Q_{11}$)($Q_{12}$)($Q_{13}$), —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), —P(=O)($Q_{11}$)($Q_{12}$), or any combination thereof, a $C_3$-$C_{60}$ carbocyclic group, a $C_1$-$C_{60}$ heterocyclic group, a $C_6$-$C_{60}$ aryloxy group, or a $C_6$-$C_{60}$ arylthio group, each unsubstituted or substituted with deuterium, —F, —Cl, —Br, —I, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, —C($Q_{21}$)($Q_{22}$)($Q_{23}$), —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), —P(=O)($Q_{21}$)($Q_{22}$), or any combination thereof, or —C($Q_{31}$)($Q_{32}$)($Q_{33}$), —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), or —P(=O)($Q_{31}$)($Q_{32}$), and $Q_1$ to $Q_3$, $Q_{11}$ to $Q_{13}$, $Q_{21}$ to $Q_{23}$, and $Q_{31}$ to $Q_{33}$ may each independently be hydrogen, deuterium, —F, —Cl, —Br, —I, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ carbocyclic group or a $C_1$-$C_{60}$ heterocyclic group, each unsubstituted or substituted with deuterium, —F, a cyano group, a $C_1$-$C_{60}$ alkyl group, a $C_1$-$C_{60}$ alkoxy group, a phenyl group, a biphenyl group, or any combination thereof.

In an embodiment, the light-emitting device may emit blue light having a maximum luminescence wavelength in a range of about 400 nm to about 500 nm, and the emission layer may have a difference of about 0.5 eV between a singlet energy level and a triplet energy level.

In an embodiment, the light emitting device may further include a capping layer disposed outside the second electrode. The capping layer may include a carbocyclic compound, a heterocyclic compound, an amine group-containing compound, a porphyrine derivative, a phthalocyanine derivative, a naphthalocyanine derivative, an alkali metal complex, an alkaline earth-metal complex, or any combination thereof.

According to another aspect, an electronic apparatus that includes the light-emitting device may further include a thin-film transistor. The thin-film transistor may include a source electrode and a drain electrode, and the first electrode of the light-emitting device may be electrically connected to the source electrode or the drain electrode.

In an embodiment, the electronic apparatus may further include an encapsulation portion. The encapsulation portion may include an organic layer, an inorganic layer, or any combination thereof.

In an embodiment, the electronic apparatus may further include a color filter, a color conversion layer, a touch screen layer, a polarizing layer, or any combination thereof.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION OF THE EMBODIMENTS

Figure 1:
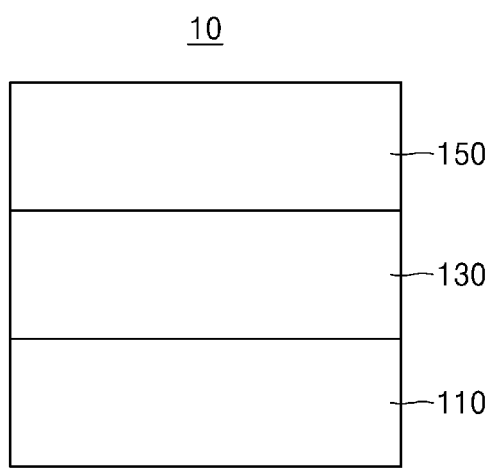
FIG. 1 is a schematic cross-sectional view of a structure of a light-emitting device according to an embodiment.

Reference will now be made in detail to embodiments, examples of which are illustrated in the accompanying drawings, wherein like reference numerals refer to like elements throughout. In this regard, the embodiments may have different forms and should not be construed as being limited to the descriptions set forth herein. Accordingly, the embodiments are merely described below, by referring to the figures, to explain aspects of the description.

Sizes of elements in the drawings may be exaggerated for convenience of explanation. Therefore, as the sizes and thicknesses of components in the drawings may be arbitrarily illustrated for convenience of explanation, the following embodiments of the disclosure are not limited thereto.

As used herein, the expressions used in the singular such as "a," "an," and "the" are intended to include the plural forms as well, unless the context clearly indicates otherwise.

It should be understood that the terms "comprises," "comprising," "includes," "including," "have," "having," "contains," "containing," and the like are intended to specify the presence of stated features, integers, steps, operations, elements, components, or combinations thereof in the disclosure, but do not preclude the presence or addition of one or more other features, integers, steps, operations, elements, components, or combinations thereof.

In the description, it will be understood that when an element (a region, a layer, a section, or the like) is referred to as being "on", "connected to" or "coupled to" another element, it can be directly on, connected or coupled to the other element, or one or more intervening elements may be disposed therebetween.

As used herein, the term "and/or" includes any and all combinations of one or more of the associated listed items. For example, "A and/or B" may be understood to mean "A, B, or A and B." The terms "and" and "or" may be used in the conjunctive or disjunctive sense and may be understood to be equivalent to "and/or".

The term "at least one of" is intended to include the meaning of "at least one selected from" for the purpose of its meaning and interpretation. For example, "at least one of A and B" may be understood to mean "A, B, or A and B." When preceding a list of elements, the term, "at least one of," modifies the entire list of elements and does not modify the individual elements of the list.

It will be understood that, although the terms "first", "second", etc. may be used herein to describe various elements, these elements should not be limited by these terms. These terms are only used to distinguish one element from another. For example, a first element could be termed a second element, and, similarly, a second element could be termed a first element, without departing from the scope of the embodiments of the inventive concept.

The terms "below," "lower," "above," "upper," and the like are used to describe the relationship of the configurations shown in the drawings. The terms are used as a relative concept and are described with reference to the direction indicated in the drawings.

The terms "about" or "approximately" as used herein is inclusive of the stated value and means within an acceptable range of deviation for the recited value as determined by one of ordinary skill in the art, considering the measurement in question and the error associated with measurement of the recited quantity (i.e., the limitations of the measurement system). For example, "about" may mean within one or more standard deviations, or within ±20%, ±10%, or ±5% of the stated value.

Unless otherwise defined or implied herein, all terms (including technical and scientific terms) used have the same meaning as commonly understood by those skilled in the art to which this disclosure pertains. It will be further understood that terms, such as those defined in commonly used dictionaries, should be interpreted as having a meaning that is consistent with their meaning in the context of the relevant art and should not be interpreted in an ideal or excessively formal sense unless clearly defined in the specification.

The light-emitting device may include a first electrode, a second electrode facing the first electrode, and an interlayer disposed between the first electrode and the second electrode and including an emission layer.

The interlayer may include a first compound represented by Formula 1, a second compound represented by Formula 2, and a third compound, and the third compound may be a blue phosphorescent compound:

[Formula 1]

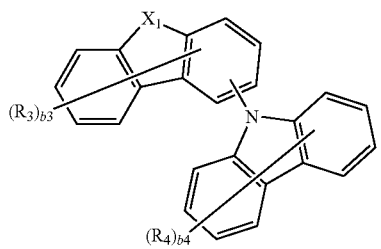

[Formula 2]

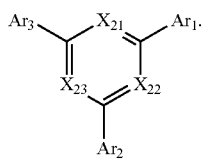

In Formula 1, $X_1$ may be $C(R_1)(R_2)$, $Si(R_1)(R_2)$, N-[$(L_1)_{a1}$-$(R_1)_{b1}$], O, or S.

In an embodiment, $X_1$ may be $C(R_1)(R_2)$ or N-[$(L_1)_{a1}$-$(R_1)_{b1}$].

In Formula 1, $L_1$ may be a $C_4$-$C_{60}$ carbocyclic group unsubstituted or substituted with at least one $R_{10a}$ or a $C_1$-$C_{60}$ heterocyclic group unsubstituted or substituted with at least one $R_{10a}$.

In an embodiment, $L_1$ may be a π electron-rich $C_3$-$C_{60}$ cyclic group unsubstituted or substituted with at least one $R_{10a}$.

In an embodiment, $L_1$ may be a benzene group or a carbazole group, each unsubstituted or substituted with at least one $R_{10a}$; or $-Si(Q_1)(Q_2)(Q_3)$.

In Formula 1, a1 may be an integer from 0 to 5.

In Formula 1, $R_1$ to $R_4$ may each independently be hydrogen, deuterium, $-F$, $-Cl$, $-Br$, $-I$, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, $-B(Q_1)(Q_2)$, $-P(Q_1)(Q_2)$, $-C(=O)(Q_1)$, or $-Si(Q_1)(Q_2)(Q_3)$.

In an embodiment, $R_1$ to $R_4$ in Formula 1 may each independently be: hydrogen, deuterium, $-F$, $-Cl$, $-Br$, $-I$, a hydroxyl group, a cyano group, or a nitro group;

a $C_1$-$C_{20}$ alkyl group, a $C_2$-$C_{20}$ alkenyl group, a $C_2$-$C_{20}$ alkynyl group, or a $C_1$-$C_{20}$ alkoxy group, each unsubstituted or substituted with deuterium, $-F$, $-C_1$, $-Br$, $-I$, $-CD_3$, $-CD_2H$, $-CDH_2$, $-CF_3$, $-CF_2H$, $-CFH_2$, a hydroxyl group, a cyano group, a nitro group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, $-Si(Q_{31})(Q_{32})(Q_{33})$, $-N(Q_{31})(Q_{32})$, $-B(Q_{31})(Q_{32})$, $-C(=O)(Q_{31})$, $-S(=O)_2(Q_{31})$, $-P(=O)(Q_{31})(Q_{32})$, or any combination thereof; or a π electron-rich $C_3$-$C_{60}$ cyclic group unsubstituted or substituted with at least one $R_{10a}$.

In Formula 1, b1 may be an integer from 0 to 10, b3 may be an integer from 0 to 7, and b4 may be an integer from 0 to 8.

The first compound may include at least one deuterium (D).

In an embodiment, the first compound may include at least four deuterium atoms.

In an embodiment, the first compound may be represented by one of Formulae 1(1) to 1(4), but embodiments of the disclosure are not limited thereto:

1(1)

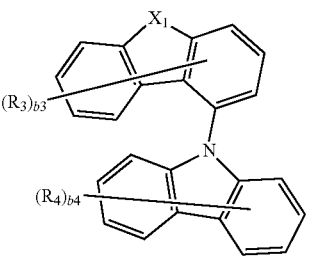

1(2)

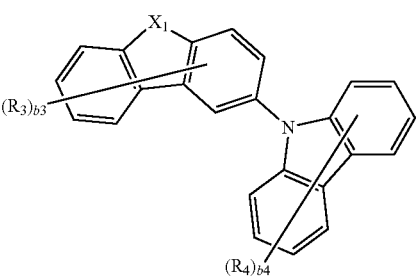

1(3)

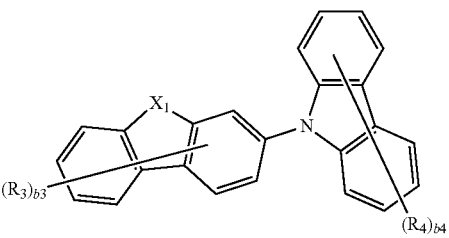

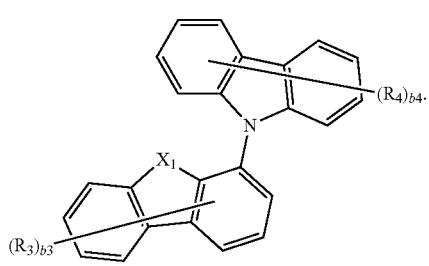
1(4)
In Formulae 1(1) to 1(4)
X₁, R₃, R₄, b3, and b4 may be the same as described in connection with Formula 1.
In an embodiment, the first compound may be selected from one of Compounds 1-1 to 1-9, but embodiments of the disclosure are not limited thereto:
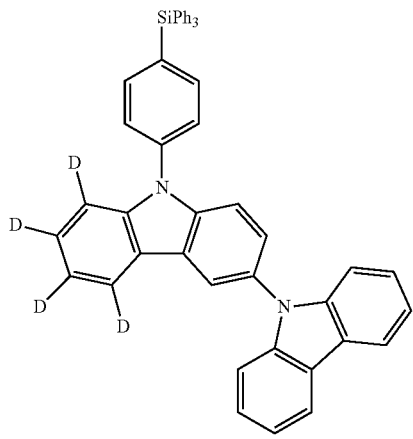
1-3
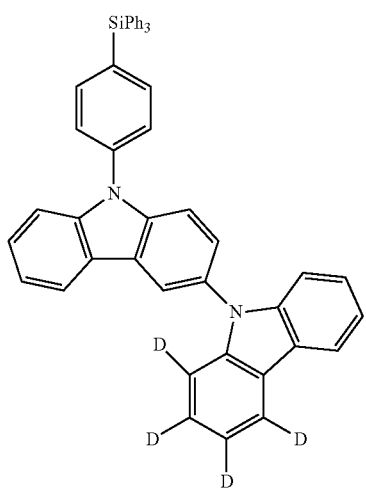
1-1
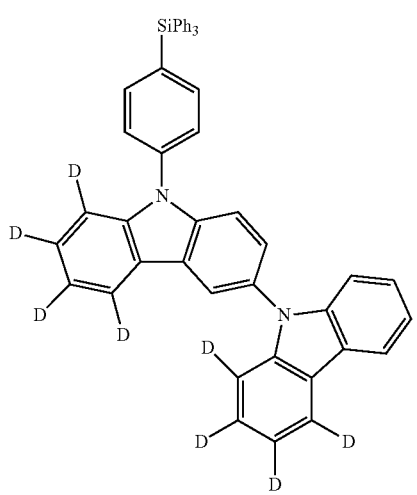
1-4
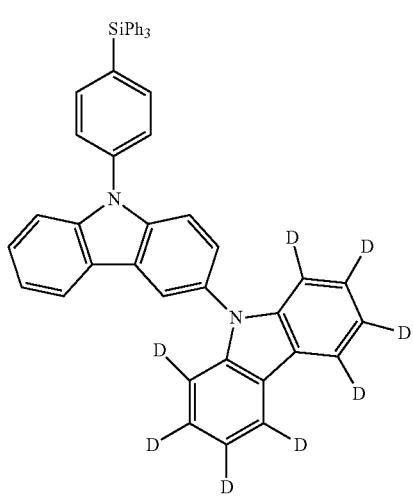
1-2
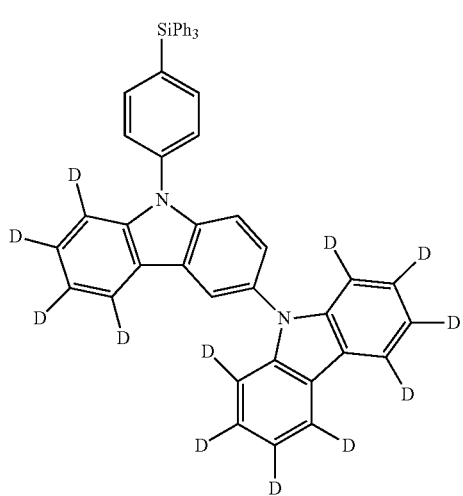
1-5

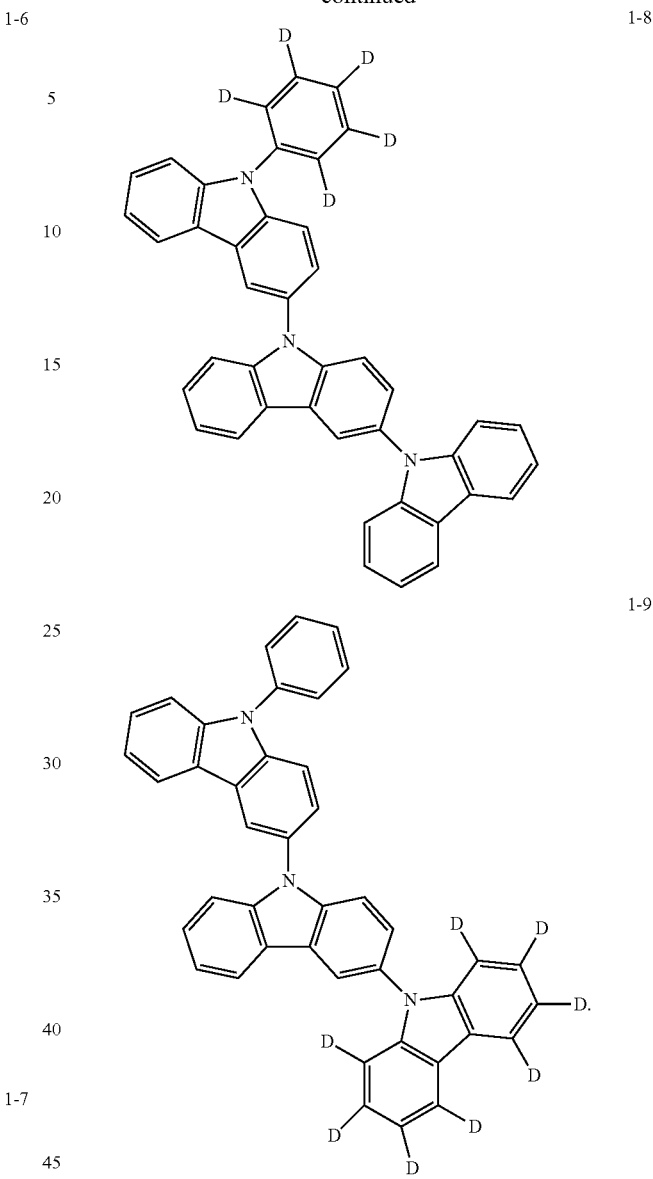

In Formula 2, $X_{21}$ may be $C(R_{21})$ or N, $X_{22}$ may be $C(R_{22})$ or N, $X_{23}$ may be $C(R_{23})$ or N, and at least one of $X_{21}$, $X_{22}$, and $X_{23}$ may be N.

In an embodiment, $X_{21}$ may be N, $X_{22}$ may be $C(R_{22})$, and $X_{23}$ may be $C(R_{23})$.

In embodiments, $X_{21}$ and $X_{22}$ may be N, and $X_{23}$ may be $C(R_{23})$.

In embodiments, $X_{21}$, $X_{22}$, and $X_{23}$ may be N.

In Formula 2, $Ar_1$ to $Ar_3$ may each independently be a $C_4$-$C_{60}$ carbocyclic group unsubstituted or substituted with at least one $R_{10a}$, a $C_1$-$C_{60}$ heterocyclic group unsubstituted or substituted with at least one $R_{10a}$, —$C(Q_1)(Q_2)(Q_3)$, or —$Si(Q_1)(Q_2)(Q_3)$.

In an embodiment, in Formula 2, $Ar_1$ to $Ar_3$ may each independently be:
  a benzene group, a naphthalene group, an anthracene group, a phenanthrene group, a triphenylene group, a pyrene group, a chrysene group, a cyclopentadiene group, a 1,2,3,4-tetrahydronaphthalene group, a thiophene group, a furan group, a pyrrole group, an indole group, an indene group, a benzosilole group, a benzothiophene group, a benzofuran group, a carbazole group, a fluorene group, a dibenzosilole group, a dibenzothiophene group, a dibenzofuran group, a pyridine group, a pyrimidine group, a pyrazine group, a pyridazine group, a triazine group, a quinoline group, an isoquinoline group, a quinoxaline group, a quinazoline group, a phenanthroline group, a pyrazole group, an imidazole group, a triazole group, an oxazole group, an isoxazole group, a thiazole group, an isothiazole group, an oxadiazole group, a thiadiazole group, a benzopyrazole group, a benzimidazole group, a benzoxazole group, a benzothiazole group, a benzoxadiazole group, a benzothiadiazole group, a 5,6,7,8-tetrahydroisoquinoline group, or a 5,6,7,8-tetrahydroquinoline group, each unsubstituted or substituted with at least one $R_{10a}$; or —$C(Q_1)(Q_2)(Q_3)$ or —$Si(Q_1)(Q_2)(Q_3)$.

In embodiments, $Ar_1$ to $Ar_3$ in Formula 2 may each independently be:
- a π electron-rich $C_3$-$C_{60}$ cyclic group unsubstituted or substituted with at least one $R_{10a}$; or
- —$C(Q_1)(Q_2)(Q_3)$ or —$Si(Q_1)(Q_2)(Q_3)$.

In embodiments, $Ar_1$ to $Ar_3$ in Formula 2 may each independently be:
- a benzene group, a cyclopentadiene group, a pyrrole group, a furan group, a thiophene group, a silole group, or a carbazole group, each unsubstituted or substituted with at least one $R_{10a}$; or
- —$C(Q_1)(Q_2)(Q_3)$ or —$Si(Q_1)(Q_2)(Q_3)$.

$R_{21}$, $R_{22}$, and $R_{23}$ in Formula 2 may each independently be the same as described in connection with $R_1$ in Formula 1.

In an embodiment, the second compound may be selected from one of Compounds 2-1 to 2-24, but embodiments of the disclosure are not limited thereto:

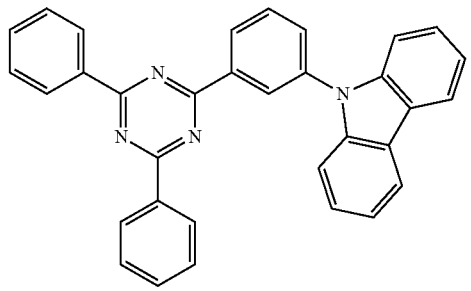

2-1

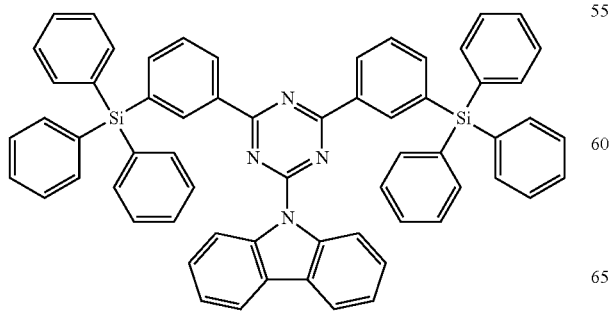

2-2

2-3

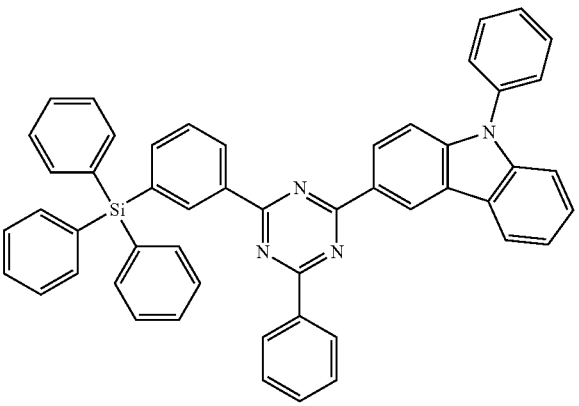

2-4

2-5

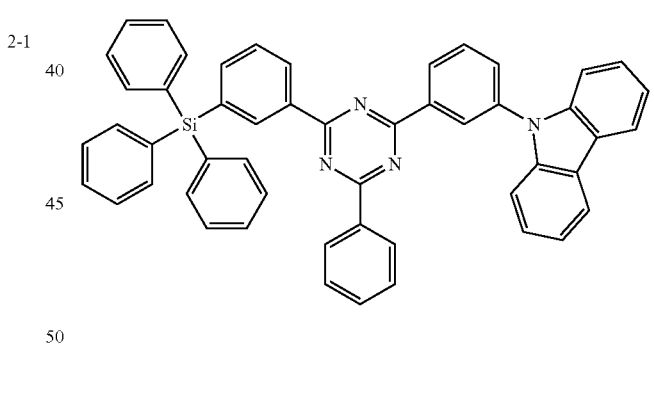

2-6

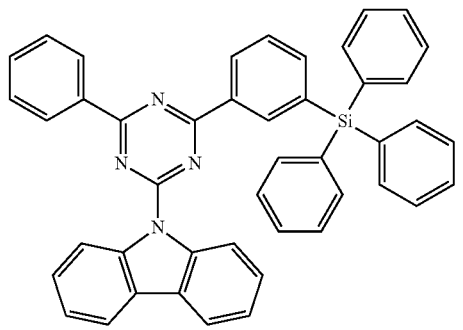

2-7
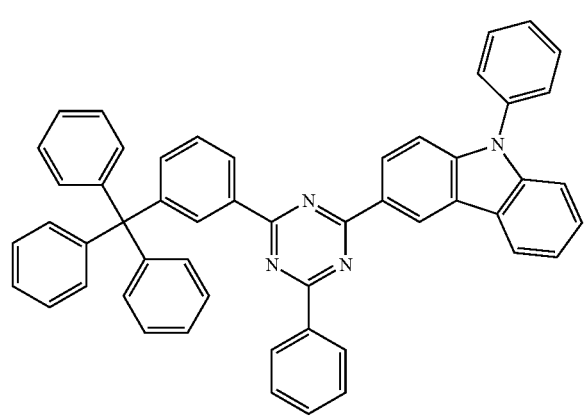
2-11
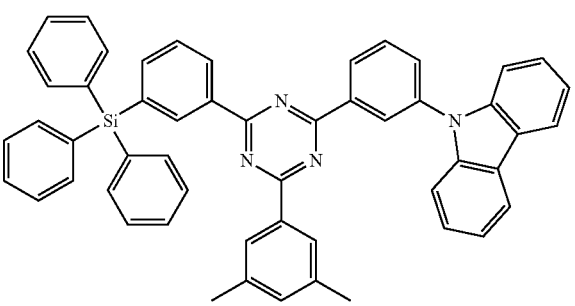
2-8
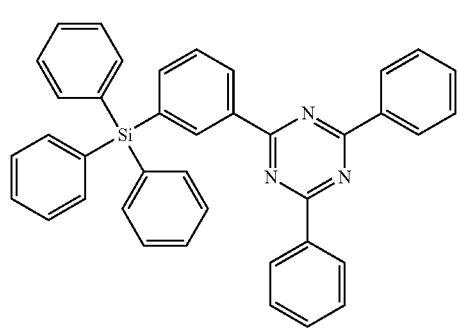
2-12
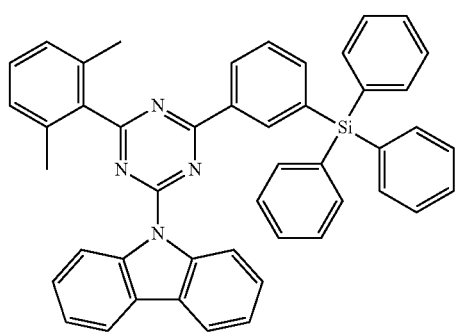
2-9
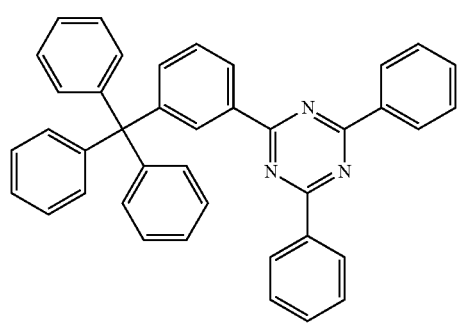
2-13
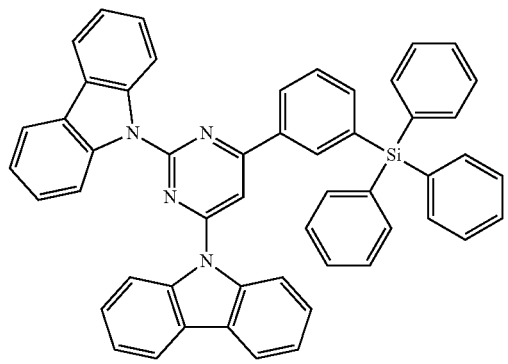
2-10
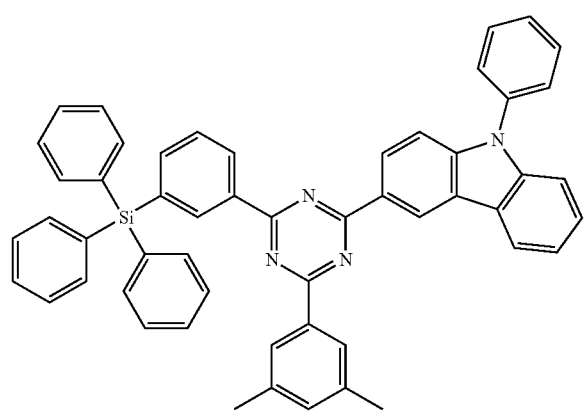
2-14
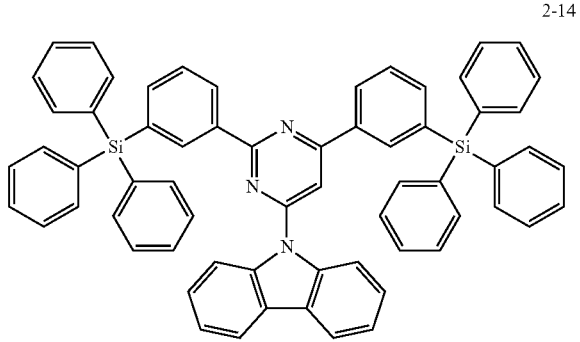

-continued
2-15
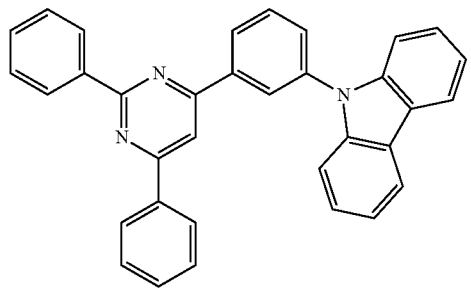
2-16
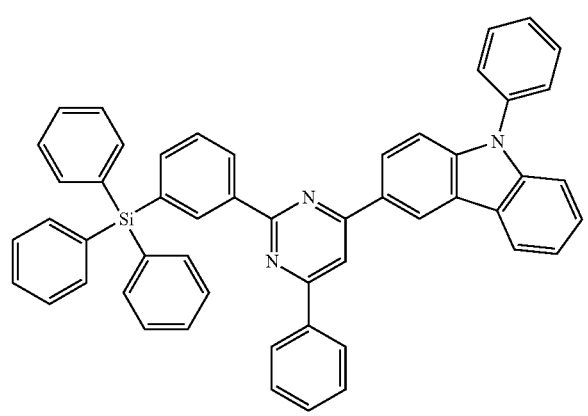
2-17
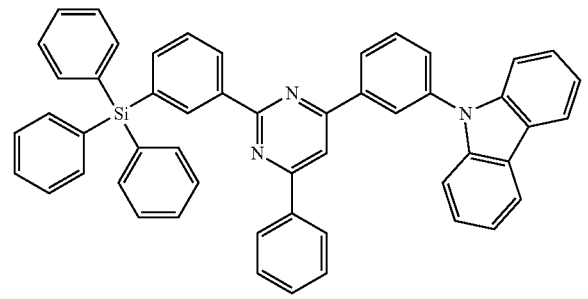
2-18
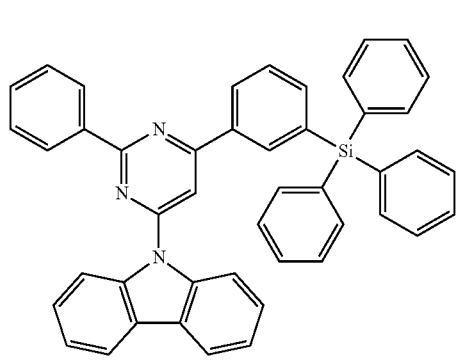
-continued
2-19
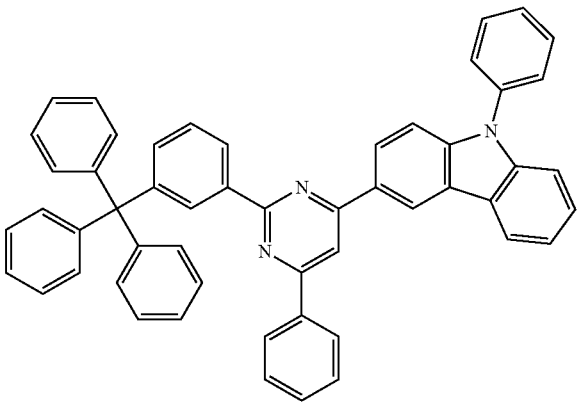
2-20
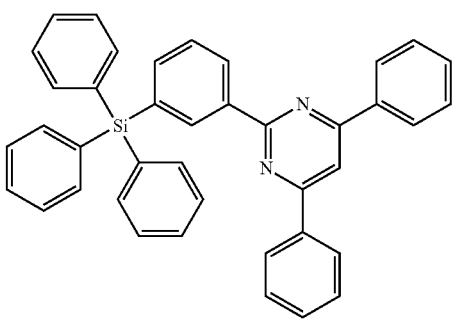
2-21
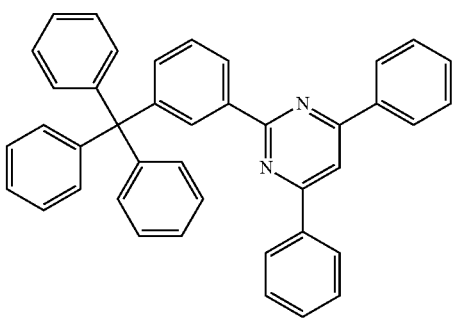
2-22
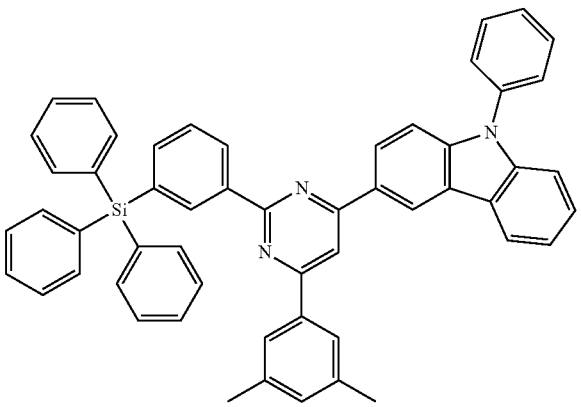

-continued 2-23
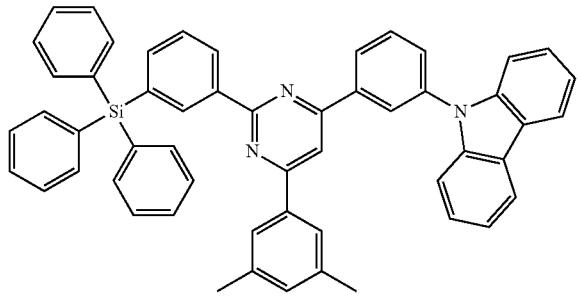

2-24
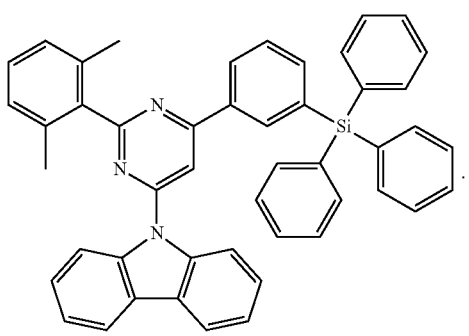

The third compound may be a platinum (Pt) complex.

In an embodiment, the third compound may be a platinum (Pt) complex including a tetradentate ligand.

In an embodiment, the third compound may include a carbene moiety in which carbon and Pt are bonded.

In an embodiment, the third compound may be represented by Formula 3:

[Formula 3]

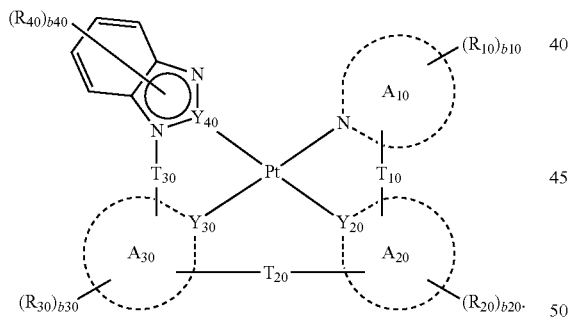

In Formula 3, $Y_{20}$, $Y_{30}$, and $Y_{40}$ may each independently be C or N, $T_{10}$ to $T_{30}$ may each independently be selected from a single bond, *—O—*', *—S—*', *—C($Z_{10a}$)($Z_{10b}$)—*', *—C($Z_{10a}$)=*', *—C($Z_{10a}$)=C($Z_{10b}$)—*', *—C(=O)—*', *—C(=S)—*', *—C≡C—*', *—B($Z_{10a}$)—*', *—N($Z_{10a}$)—*', *—P($Z_{10a}$)—*', and *—Si($Z_{10a}$)($Z_{10b}$)—*', $A_{10}$, $A_{20}$, and $A_{30}$ may each independently be a $C_4$-$C_{60}$ carbocyclic group or a $C_1$-$C_{60}$ heterocyclic group, $Z_{10a}$ and $Z_{10b}$ may each independently be the same as defined in connection with $R_1$ in Formula 1, $R_{10}$, $R_{20}$, $R_{30}$, and $R_{40}$ may each independently be the same as described in connection with $R_1$ in Formula 1, b10, b20, and b30 may each independently be an integer from 0 to 10, and b40 may be an integer from 0 to 5, and and *' each indicate a binding site to a neighboring atom.

In an embodiment, in Formula 3, $Y_{40}$ may be C, and a bond between $Y_{40}$ and Pt may be a coordinate bond.

In an embodiment, in Formula 3, a bond between $Y_{40}$ and Pt and a bond between N and Pt may each be a coordinate bond, and a bond between $Y_{30}$ and Pt and a bond between $Y_{20}$ and Pt may each be a covalent bond.

In an embodiment, in Formula 3, $T_{10}$ and $T_{30}$ may each be a single bond, and $T_{20}$ may not be a single bond.

In an embodiment, Formula 3 may satisfy at least one of Condition 1 to Condition 3:

Condition 1
$A_{10}$ is a pyridine group.
Condition 2
$A_{20}$ is a carbazole group.
Condition 3
$A_{30}$ is a benzene group.

In an embodiment, the third compound may be represented by one of Formulae 3(1) and 3(2):

3(1)
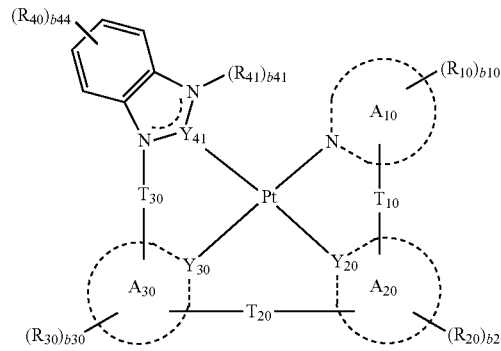

3(2)
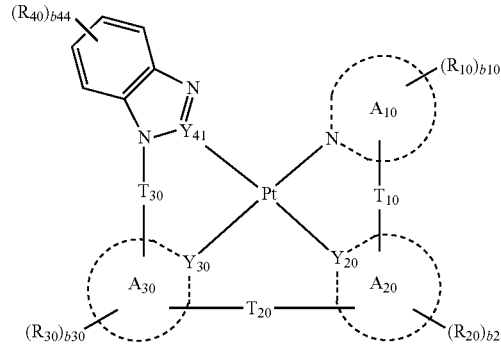

In Formulae 3(1) and 3(2), $Y_{20}$, $Y_{30}$, $T_{10}$, $T_{20}$, $T_{30}$, $A_{10}$, $A_{20}$, $A_{30}$, $R_{10}$, $R_{20}$, $R_{30}$, $R_{40}$, $b_{10}$, $b_{20}$, and $b_{30}$ may be the same as described in connection with Formula 3, $Y_{41}$ may be C, $R_{41}$ is the same as described in connection with $R_{40}$ in Formula 3, b41 may be 1, and b44 may be an integer from 0 to 4.

In an embodiment, the third compound may be selected from one of Compounds 3-1 to 3-4, but embodiments of the disclosure are not limited thereto:

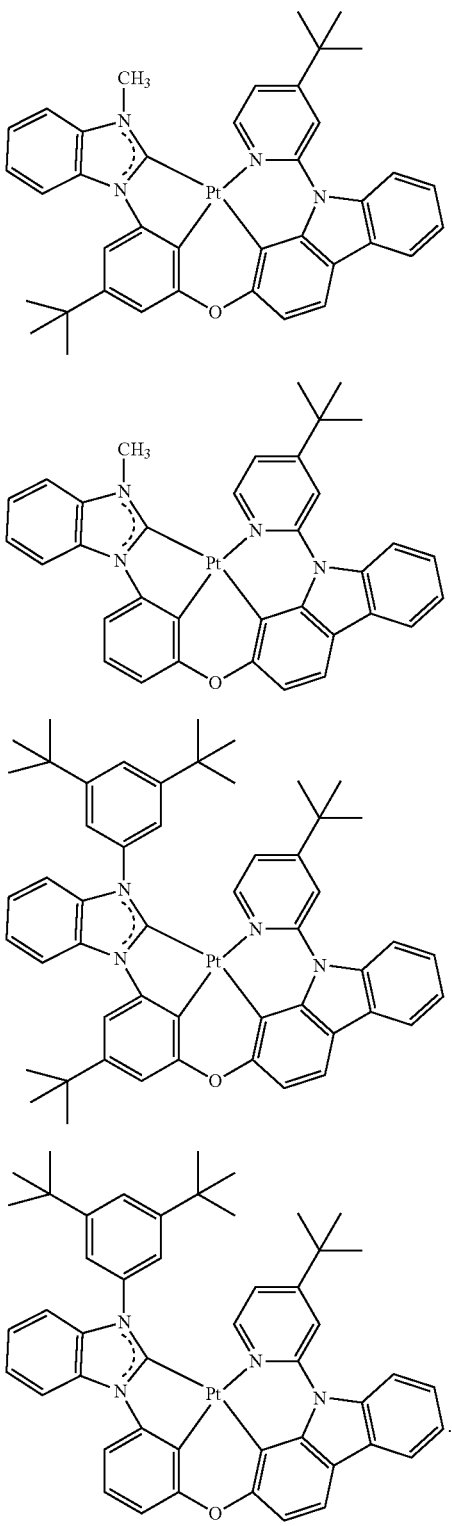

3-1

3-2

3-3

3-4

Because the first compound represented by Formula 1 provides high light emission efficiency, and the first compound includes at least one deuterium (D), resonance may be suppressed in the first compound, and charge mobility is excellent, thus a device including the first compound may have an improved lifespan and improved light emission efficiency. Charge transfer efficiency and exciton generation efficiency of the third compound may increase due to resonance suppression of the first compound, and thus an absolute quantity of excitons transferred to the third compound, which is luminescent, increases, resulting in improved light emission efficiency. Therefore, a light-emitting device, for example, an organic light-emitting device using the first compound, the second compound, and the third compound together as a material for an emission layer, may have excellent light emission efficiency and long lifespan, and in terms of a blue phosphorescent device, the lifespan of the device may be improved while high efficiency is maintained.

Synthesis methods of the first compound, the second compound, and the third compound may be recognizable by one of ordinary skill in the art with reference to Synthesis Examples and/or Examples provided below.

At least one of each of the first compound, the second compound, and the third compound may be used in a light-emitting device (for example, an organic light-emitting device). Thus, a light-emitting device may include a first electrode; a second electrode facing the first electrode; and an interlayer disposed between the first electrode and the second electrode and including an emission layer, wherein the interlayer may include a first compound as described in the specification, a second compound as described in the specification, and a third compound as described in the specification.

In an embodiment, the first compound and the second compound may act as a host, and
the third compound may act as a phosphorescent dopant such that phosphorescence may be emitted from the emission layer, or may act as a fluorescent dopant such that delayed fluorescence may be emitted from the emission layer.

In an embodiment, the first electrode of the light-emitting device may be an anode, the second electrode of the light-emitting device may be a cathode, the interlayer may further include a hole transport region between the first electrode and the emission layer and an electron transport region between the emission layer and the second electrode,
the hole transport region may include a hole injection layer, a hole transport layer, an emission auxiliary layer, an electron blocking layer, or any combination thereof, and
the electron transport region may include a hole blocking layer, an electron transport layer, an electron injection layer, or any combination thereof.

In an embodiment, at least one of the hole transport region and the emission layer may include an arylamine-containing compound, an acridine-containing compound, a carbazole-containing compound, or any combination thereof, or
at least one of the emission layer and the electron transport region may include a silicon-containing compound, a phosphine oxide-containing compound, a sulfur oxide-containing compound, a phosphorus oxide-containing compound, a triazine-containing compound, a pyrimidine-containing compound, a pyridine-containing compound, a dibenzofuran-containing compound, a dibenzothiophene-containing compound, or any combination thereof.

In embodiments, at least one of each of the first compound, the second compound, and the third compound may be included between a pair of electrodes of the light-emitting device. Accordingly, at least one of each of the first compound, the second compound, and the third compound may be included in the interlayer of the light-emitting device, for example, the emission layer of the interlayer.

In embodiments, the emission layer in the interlayer of the light-emitting device may include a dopant and a host, wherein the first compound and the second compound may be included in the host, and the third compound may be included in the dopant. Thus, the first compound and the second compound may act as a host, and the third compound may act as a dopant. The emission layer may emit red light, green light, blue light, and/or white light. In an embodiment, the emission layer may emit blue light. The blue light may have a maximum luminescence wavelength in a range of about 400 nm to about 500 nm. For example, the blue light may have a maximum luminescence wavelength in a range of about 450 nm to about 500 nm. In an embodiment, the emission layer may have a difference of equal to or less than about 0.5 eV between a singlet ($S_1$) energy level and a triplet ($T_1$) energy level.

In embodiments, the light-emitting device may further include at least one of a first capping layer disposed outside the first electrode and a second capping layer disposed outside the second electrode, wherein the first compound, the second compound, the third compound, or any combination thereof may be included in at least one of the first capping layer and the second capping layer. More details on the first capping layer and the second capping layer are the same as described in the specification.

In an embodiment, the light-emitting device may include: a first capping layer disposed outside the first electrode and including the first compound; a second capping layer disposed outside the second electrode and including the first compound; or the first capping layer and the second capping layer.

The term "interlayer" as used herein refers to a single layer or all layers located between the first electrode and the second electrode of the light-emitting device.

According to another aspect, an electronic apparatus including the light-emitting device is provided. The electronic apparatus may further include a thin-film transistor. In embodiments, the electronic apparatus may further include a thin-film transistor including a source electrode and a drain electrode, and the first electrode of the light-emitting device may be electrically connected to the source electrode or the drain electrode. In an embodiment, the electronic apparatus may further include a color filter, a color conversion layer, a touch screen layer, a polarizing layer, or any combination thereof. More details on the electronic apparatus are the same as described in the specification.

[Description of FIG. 1]

FIG. 1 is a schematic cross-sectional view of a light-emitting device 10 according to an embodiment. The light-emitting device 10 includes a first electrode 110, an interlayer 130, and a second electrode 150.

Hereinafter, a structure of the light-emitting device 10 according to an embodiment and a method of manufacturing the light-emitting device 10 will be described in connection with FIG. 1.

[First Electrode 110]

In FIG. 1, a substrate may be additionally located under the first electrode 110 or above the second electrode 150. The substrate may be a glass substrate or a plastic substrate. The substrate may be a flexible substrate. In embodiments, the substrate may include plastics with excellent heat resistance and durability, such as polyimide, polyethylene terephthalate (PET), polycarbonate, polyethylene naphthalate, polyarylate (PAR), polyetherimide, or any combination thereof.

The first electrode 110 may be formed by, for example, depositing or sputtering a material for forming the first electrode 110 on the substrate. When the first electrode 110 is an anode, a high work function material that can easily inject holes may be used as a material for forming the first electrode 110.

The first electrode 110 may be a reflective electrode, a semi-transmissive electrode, or a transmissive electrode. When the first electrode 110 is a transmissive electrode, a material for forming the first electrode 110 may include indium tin oxide (ITO), indium zinc oxide (IZO), tin oxide ($SnO_2$), zinc oxide (ZnO), or any combination thereof. In embodiments, when the first electrode 110 is a semi-transmissive electrode or a reflective electrode, magnesium (Mg), silver (Ag), aluminum (Al), aluminum-lithium (Al—Li), calcium (Ca), magnesium-indium (Mg—In), magnesium-silver (Mg—Ag), or any combination thereof may be used as a material for forming the first electrode 110.

The first electrode 110 may have a single-layered structure consisting of a single layer or a multi-layered structure including multiple layers. In an embodiment, the first electrode 110 may have a three-layered structure of ITO/Ag/ITO.

[Interlayer 130]

The interlayer 130 is disposed on the first electrode 110. The interlayer 130 includes an emission layer.

The interlayer 130 may further include a hole transport region between the first electrode 110 and the emission layer and an electron transport region between the emission layer and the second electrode 150.

The interlayer 130 may further include metal-containing compounds such as organometallic compounds, inorganic materials such as quantum dots, and the like, in addition to various organic materials.

In embodiments, the interlayer 130 may include, i) two or more emitting units sequentially stacked between the first electrode 110 and the second electrode 150 and ii) at least one charge generation layer between adjacent ones of the emitting units. When the interlayer 130 includes the emitting units and the at least one charge generation layer as described above, the light-emitting device 10 may be a tandem light-emitting device.

[Hole Transport Region in Interlayer 130]

The hole transport region may have i) a single-layered structure consisting of a single layer consisting of a single material, ii) a single-layered structure consisting of a single layer including different materials, or iii) a multi-layered structure including layers including different materials.

The hole transport region may include a hole injection layer, a hole transport layer, an emission auxiliary layer, an electron blocking layer, or any combination thereof.

In an embodiment, the hole transport region may have a multi-layered structure including a hole injection layer/hole transport layer structure, a hole injection layer/hole transport layer/emission auxiliary layer structure, a hole injection layer/emission auxiliary layer structure, a hole transport layer/emission auxiliary layer structure, or a hole injection layer/hole transport layer/electron blocking layer structure, wherein, in each structure, layers are stacked sequentially from the first electrode 110.

The hole transport region may include a compound represented by Formula 201, a compound represented by Formula 202, or any combination thereof:

[Formula 201]

$$R_{201}-(L_{201})_{xa1}-N\begin{matrix}(L_{202})_{xa2}-R_{202}\\ \\(L_{203})_{xa3}-R_{203}\end{matrix}$$

[Formula 202]

$$\begin{matrix}R_{201}-(L_{201})_{xa1}\\ \\R_{202}-(L_{202})_{xa2}\end{matrix}N-(L_{205})_{xa5}\left[N\begin{matrix}(L_{203})_{xa3}-R_{203}\\ \\(L_{204})_{xa4}-R_{204}\end{matrix}\right]_{na1}.$$

In Formulae 201 and 202, $L_{201}$ to $L_{204}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, $L_{205}$ may be *—O—*', *—S—*', *—N(Q$_{201}$)—*', a $C_1$-$C_{20}$ alkylene group unsubstituted or substituted with at least one $R_{10a}$, a $C_2$-$C_{20}$ alkenylene group unsubstituted or substituted with at least one $R_{10a}$, a $C_3$-$C_{60}$ carbocyclic group unsubstituted or substituted with at least one $R_{10a}$, or a $C_1$-$C_{60}$ heterocyclic group unsubstituted or substituted with at least one $R_{10a}$, xa1 to xa4 may each independently be an integer from 0 to 5, xa5 may be an integer from 1 to 10, $R_{201}$ to $R_{204}$ and $Q_{201}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, $R_{201}$ and $R_{202}$ may optionally be linked to each other via a single bond, a $C_1$-$C_5$ alkylene group unsubstituted or substituted with at least one $R_{10a}$, or a $C_2$-$C_5$ alkenylene group unsubstituted or substituted with at least one $R_{10a}$, to form a $C_8$-$C_{60}$ polycyclic group unsubstituted or substituted with at least one $R_{10a}$ (for example, a carbazole group) (for example, see Compound HT16 or the like), $R_{203}$ and $R_{204}$ may optionally be linked to each other via a single bond, a $C_1$-$C_5$ alkylene group unsubstituted or substituted with at least one $R_{10a}$, or a $C_2$-$C_5$ alkenylene group unsubstituted or substituted with at least one $R_{10a}$, to form a $C_8$-$C_{60}$ polycyclic group unsubstituted or substituted with at least one $R_{10a}$, and na1 may be an integer from 1 to 4.

In an embodiment, Formulae 201 and 202 may each include at least one of the groups represented by Formulae CY201 to CY217:

-continued

CY211
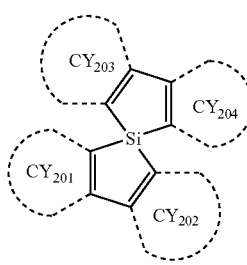

CY212

CY213
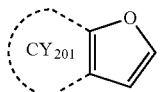

CY214
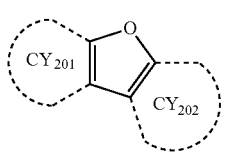

CY215

CY216
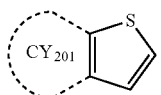

CY217
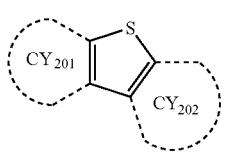

Regarding Formulae CY201 to CY217, $R_{10b}$ and $R_{10c}$ are the same as described in connection with $R_{10a}$, ring CY201 to ring CY204 may each independently be a $C_3$-$C_{20}$ carbocyclic group or a $C_1$-$C_{20}$ heterocyclic group, and at least one hydrogen in Formula CY201 to CY217 may be unsubstituted or substituted with at least one $R_{10a}$ described herein.

In an embodiment, ring CY201 to ring CY204 in Formulae CY201 to CY217 may each independently be a benzene group, a naphthalene group, a phenanthrene group, or an anthracene group.

In an embodiment, Formulae 201 and 202 may each include at least one of the groups represented by Formulae CY201 to CY203.

In an embodiment, Formula 201 may include at least one of the groups represented by Formulae CY201 to CY203 and at least one of the groups represented by Formulae CY204 to CY217.

In embodiments, in Formula 201, xa1 is 1, $R_{201}$ is a group represented by one of Formulae CY201 to CY203, xa2 is 0, and $R_{202}$ is a group represented by one of Formulae CY204 to CY207.

In embodiments, each of Formulae 201 and 202 may not include groups represented by Formulae CY201 to CY203.

In embodiments, each of Formulae 201 and 202 may not include groups represented by Formulae CY201 to CY203 and may include at least one of the groups represented by Formulae CY204 to CY217.

In an embodiment, each of Formulae 201 and 202 may not include groups represented by Formulae CY201 to CY217.

In an embodiment, the hole transport region may include one of Compounds HT1 to HT44, m-MTDATA, TDATA, 2-TNATA, NPB(NPD), β-NPB, TPD, Spiro-TPD, Spiro-NPB, methylated-NPB, TAPC, HMTPD, 4,4',4"-tris(N-carbazolyl)triphenylamine (TCTA), polyaniline/dodecylbenzenesulfonic acid (PANI/DBSA), poly(3,4-ethylenedioxythiophene)/poly(4-styrenesulfonate) (PEDOT/PSS), polyaniline/camphor sulfonic acid (PANI/CSA), polyaniline/poly(4-styrenesulfonate) (PANI/PSS), or any combination thereof:

HT1

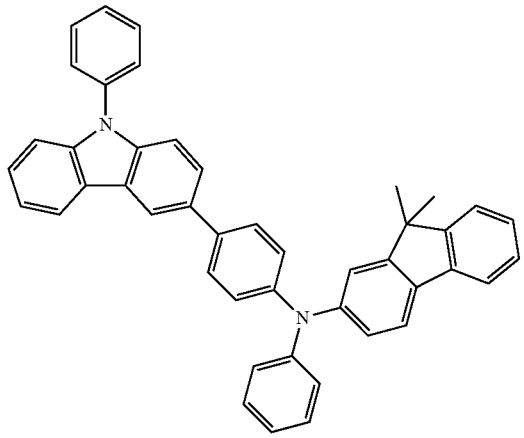

HT2

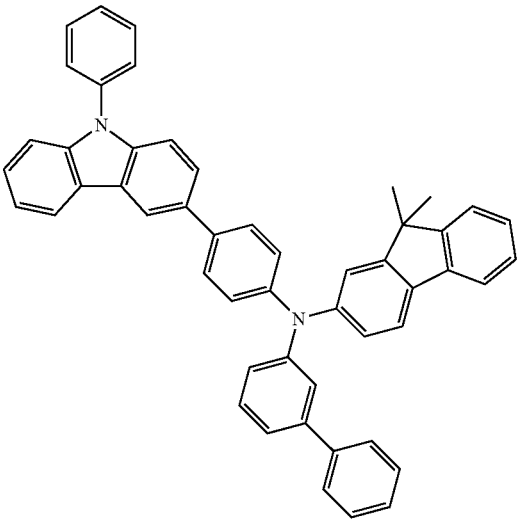

-continued
HT3
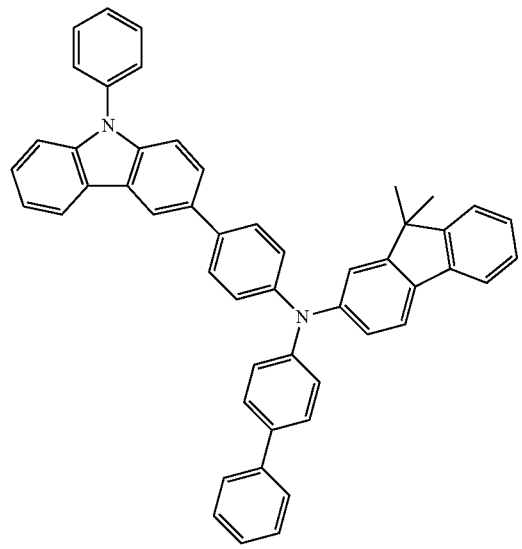
HT4
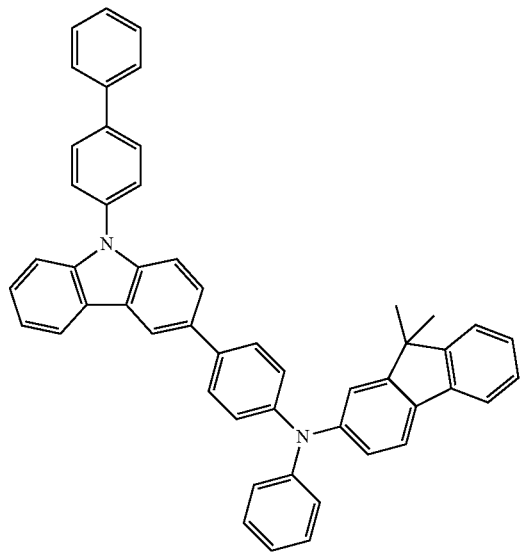
HT5
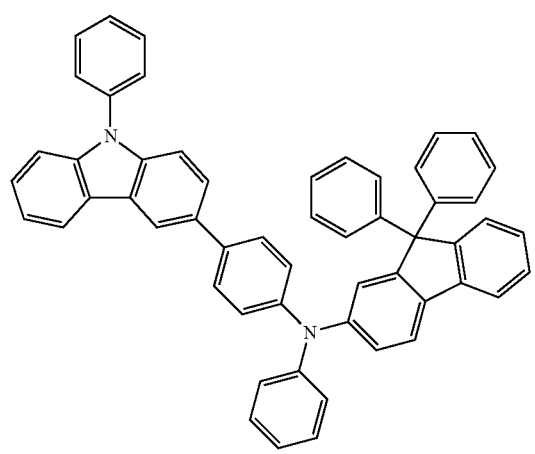
HT6
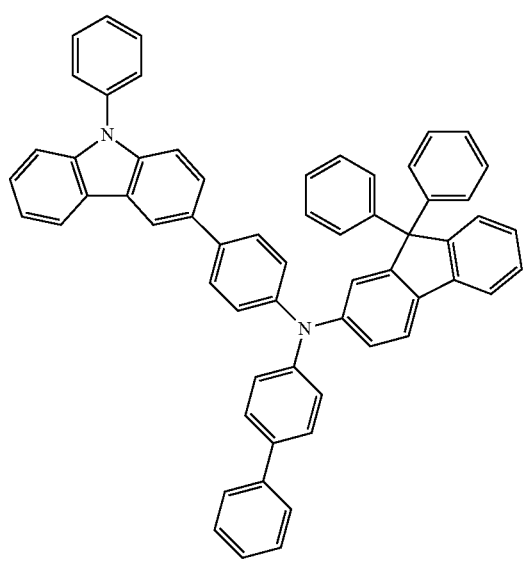

-continued
HT7
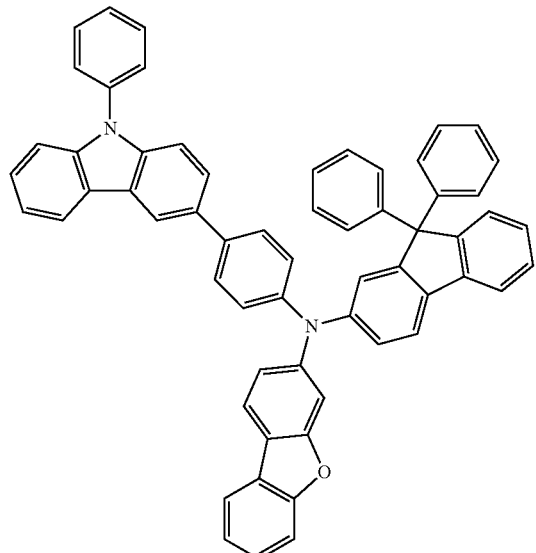
HT8
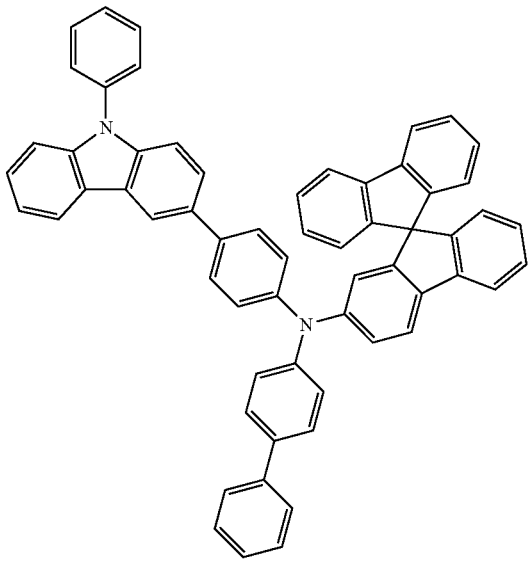
HT9
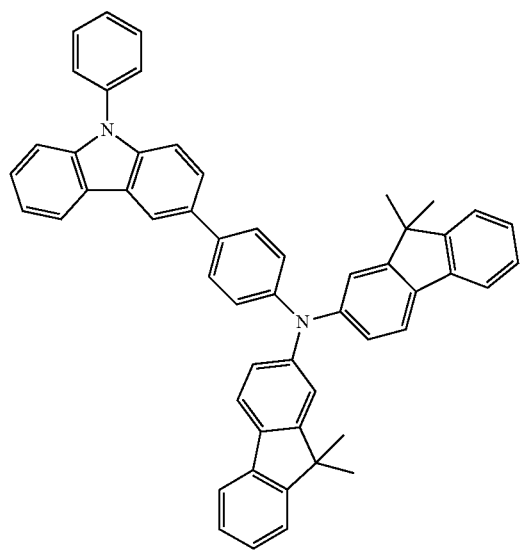
HT10
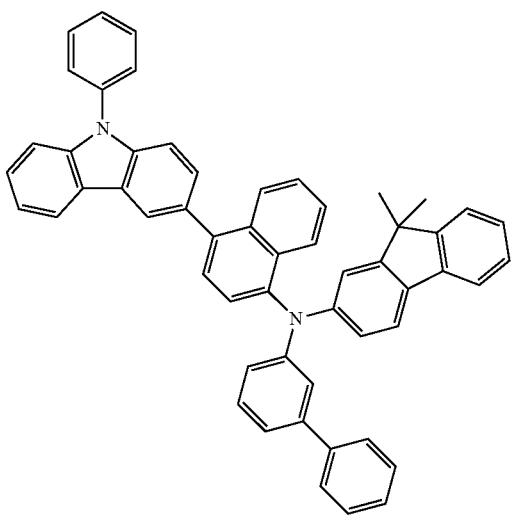
HT11
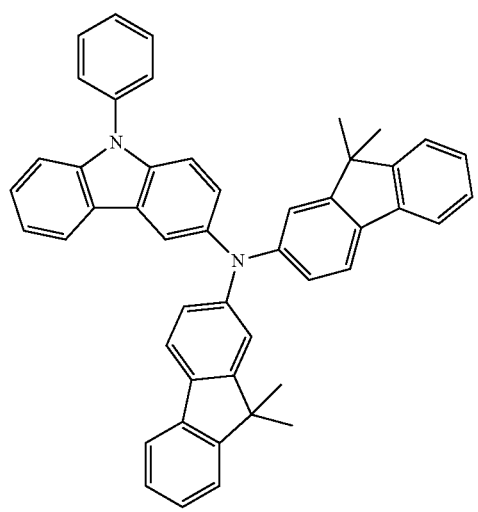
HT12
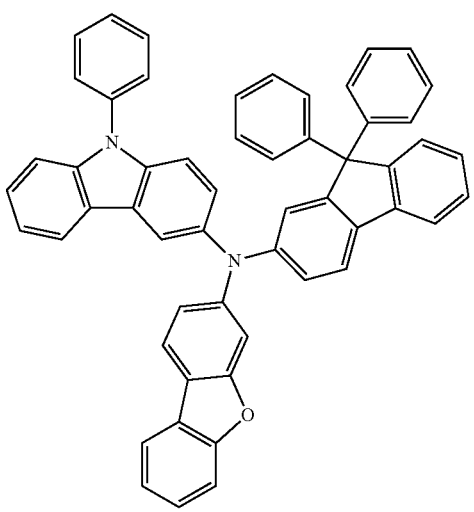

-continued
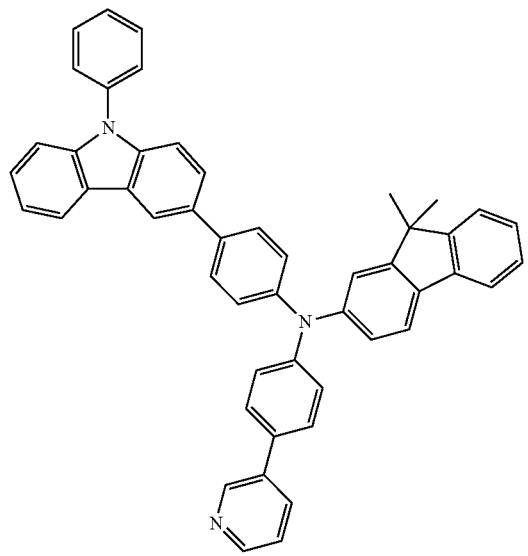

-continued
HT19
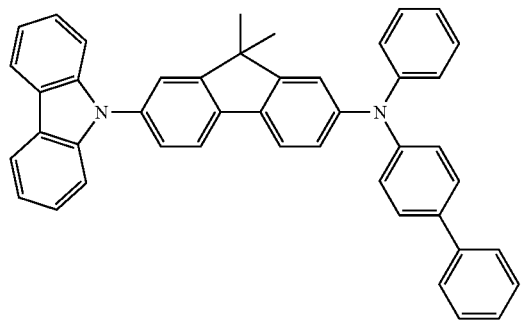
HT20
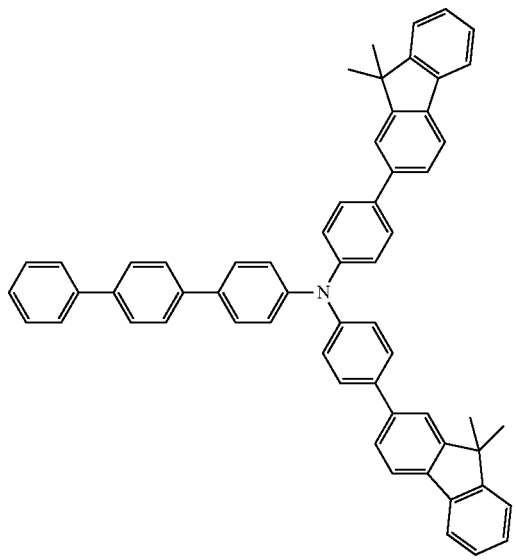
HT21
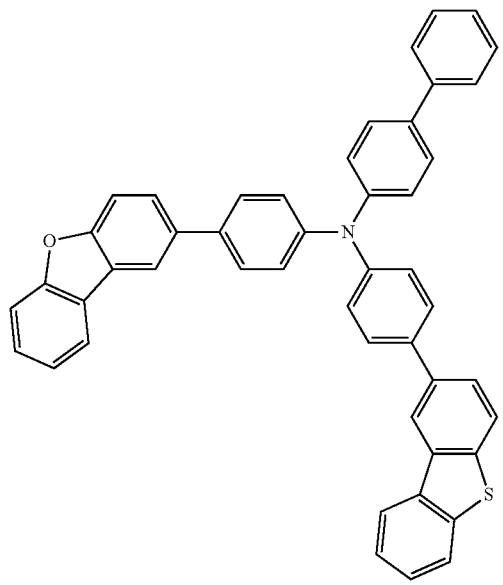
HT22
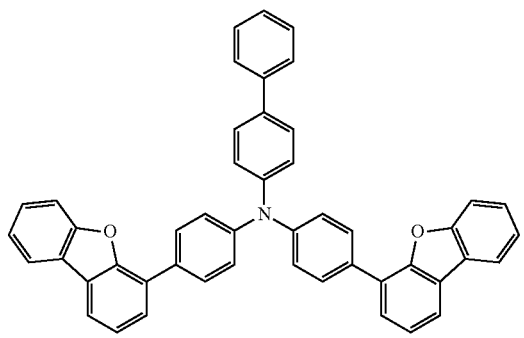
HT23
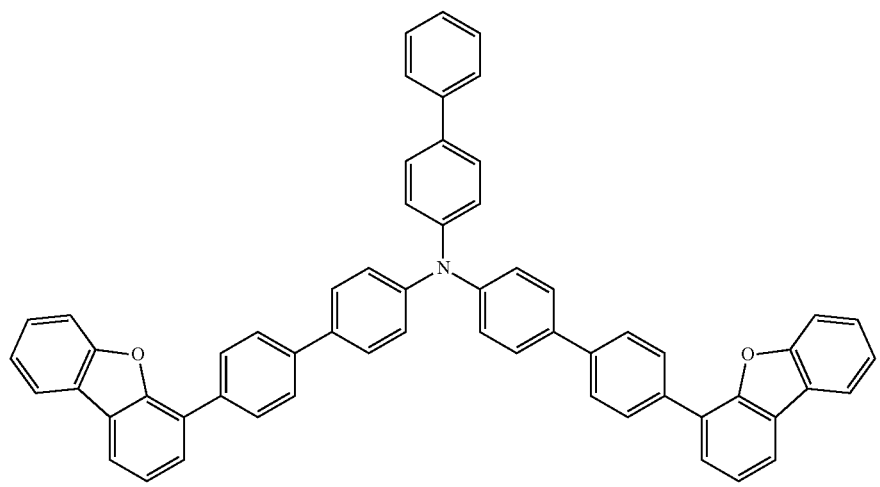

-continued
HT24
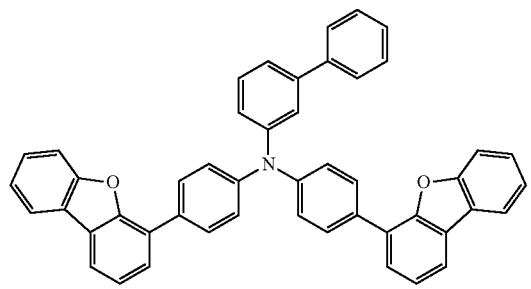
HT25
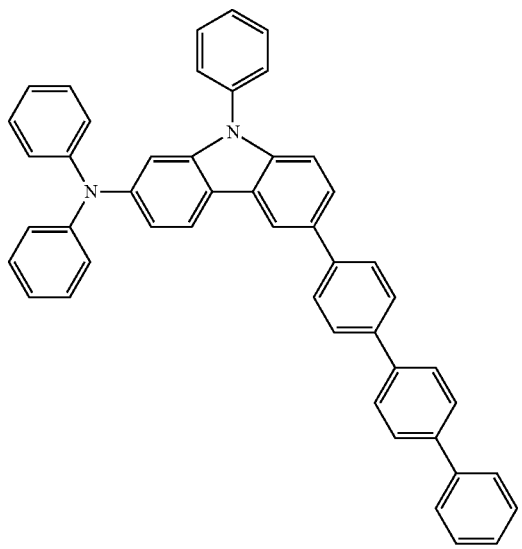
HT26
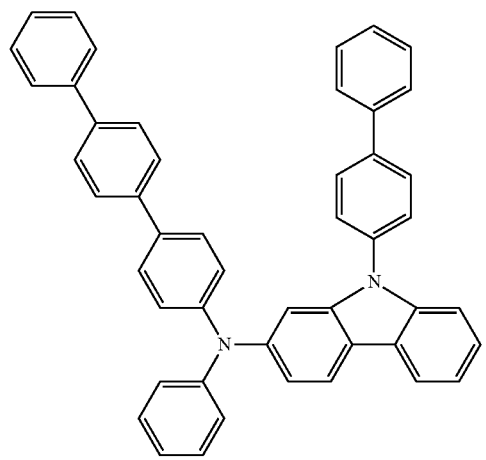
HT27
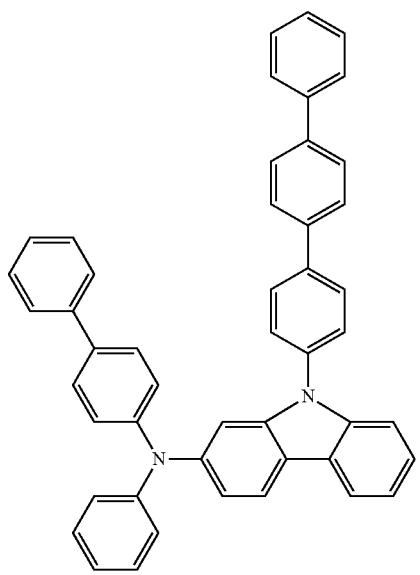
HT28
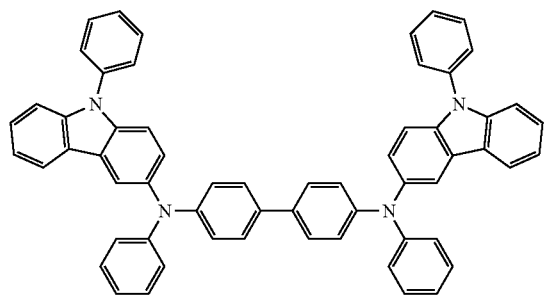
HT29
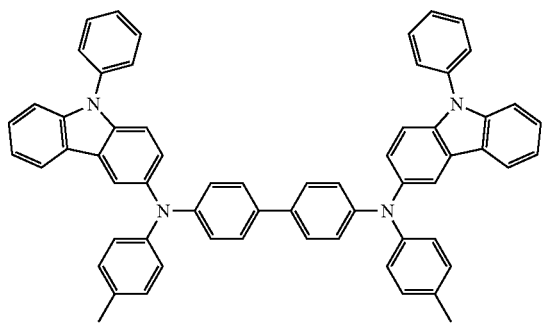

-continued
HT30
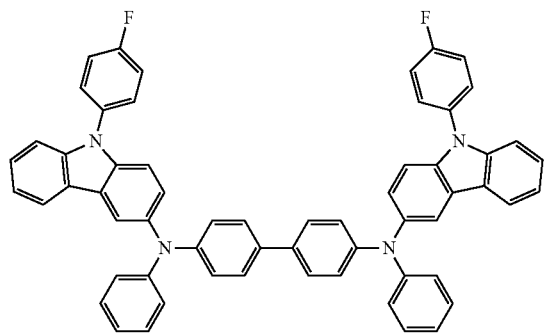
HT31
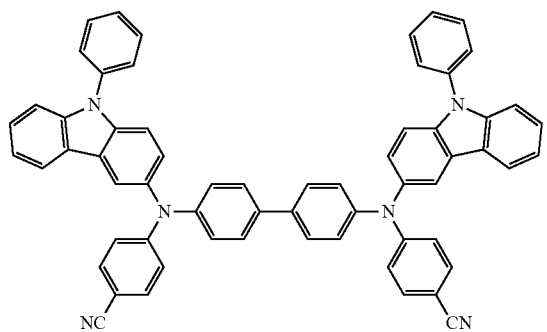
HT32
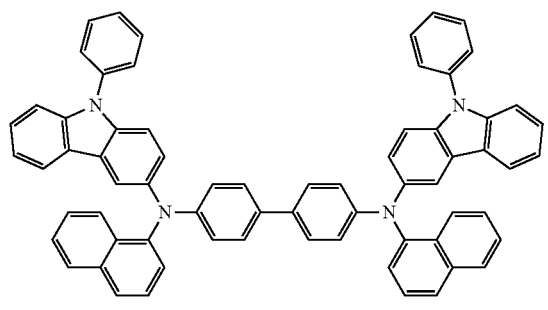
HT33
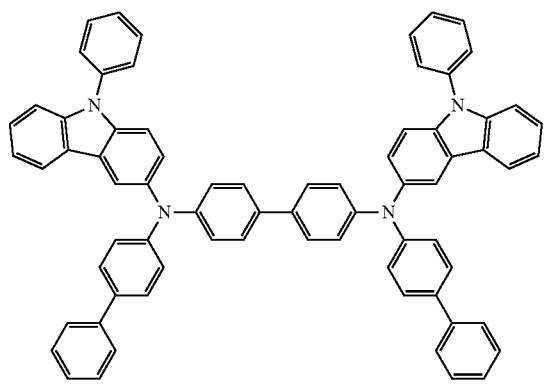
HT34
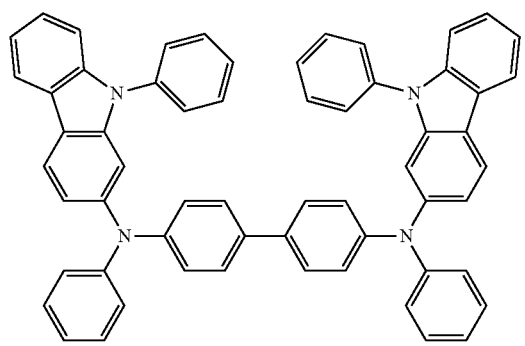
HT35
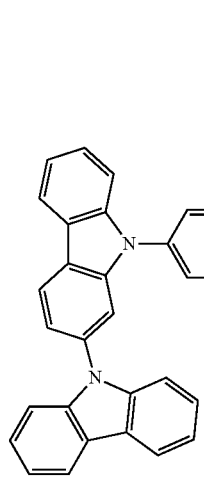

-continued
HT36
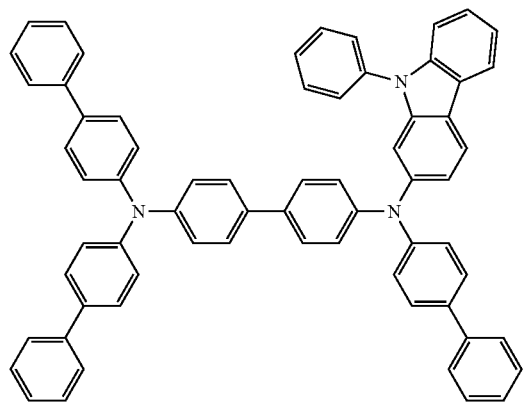
HT37
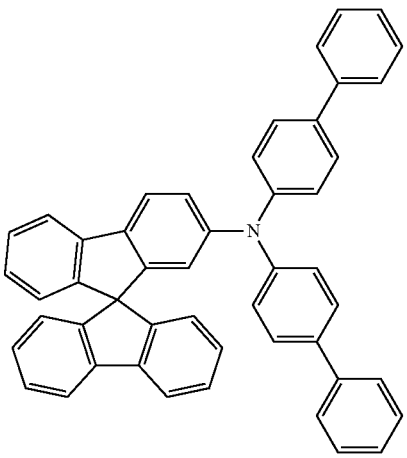
HT38
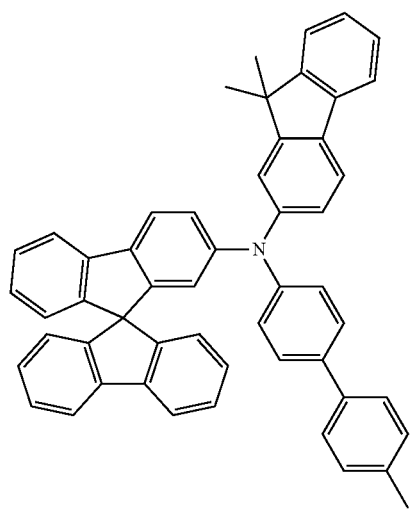
HT39
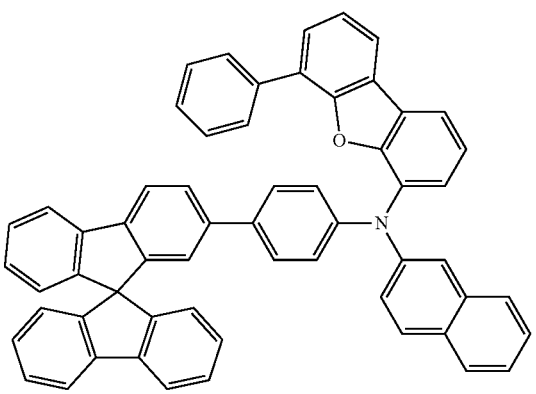
HT40
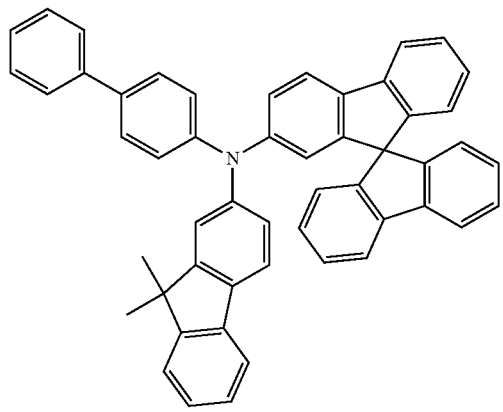
HT41
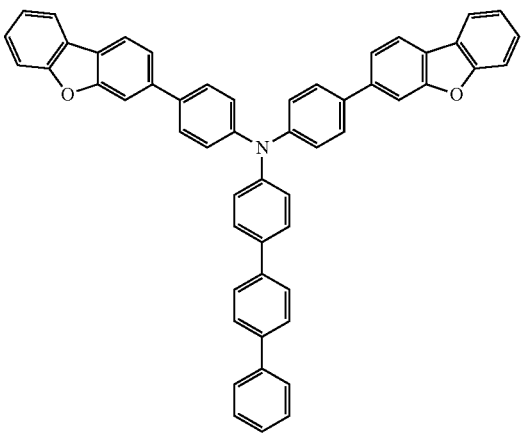

-continued
HT42
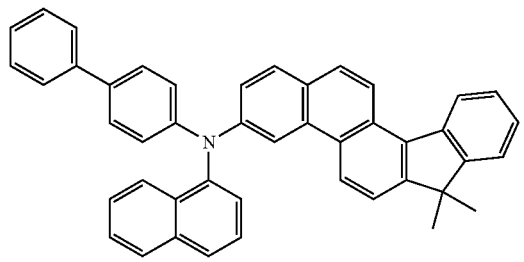
HT43
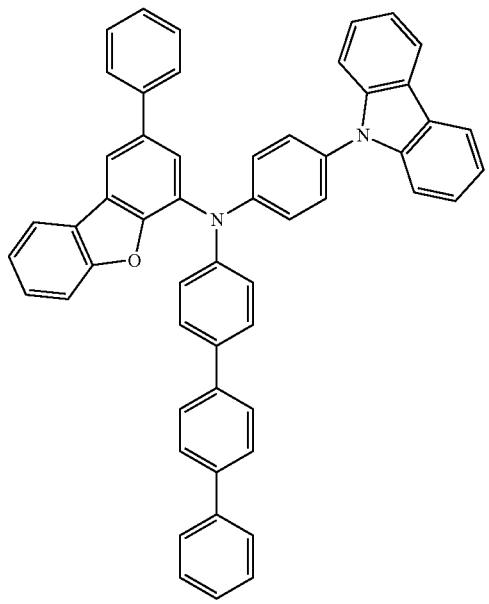
HT44
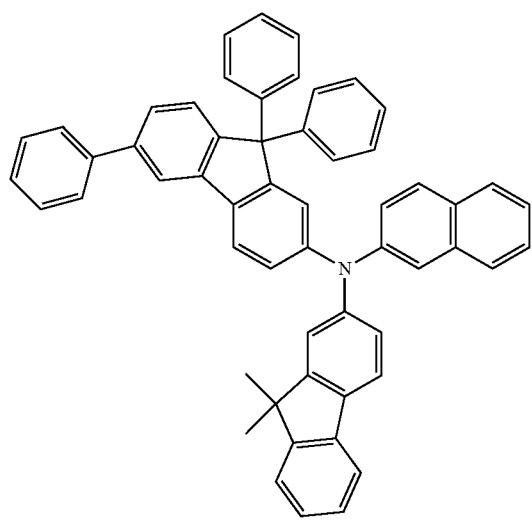

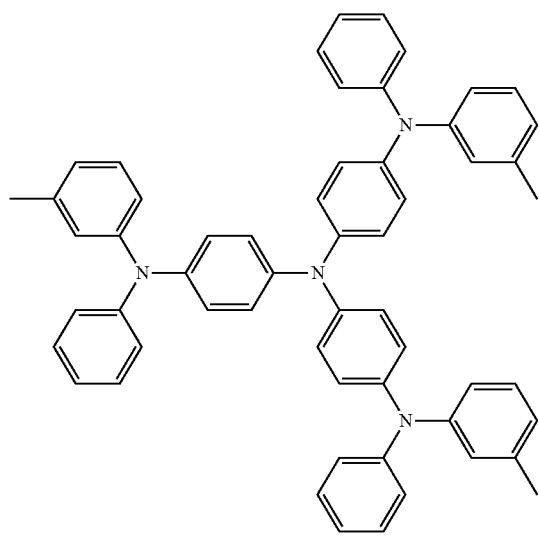
m-MTDATA
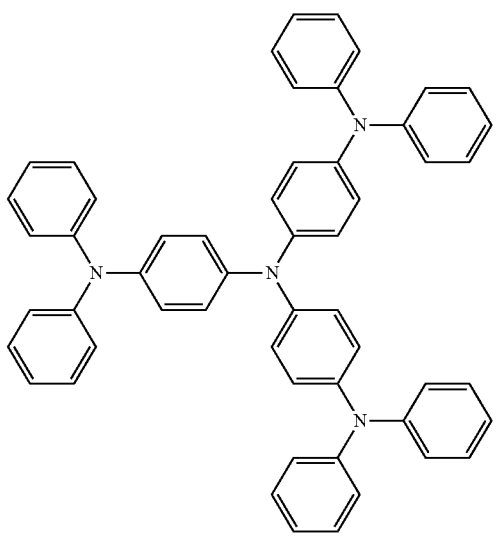
TDATA
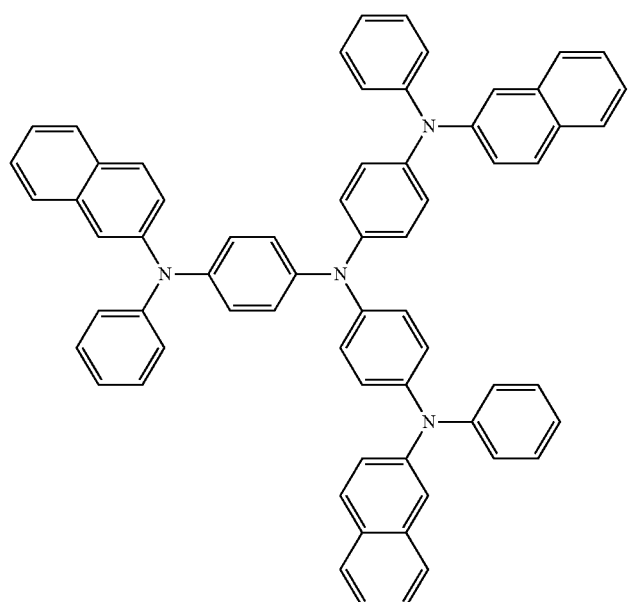
2-TNATA
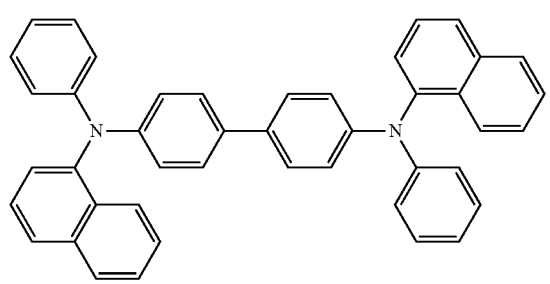
NPB

-continued
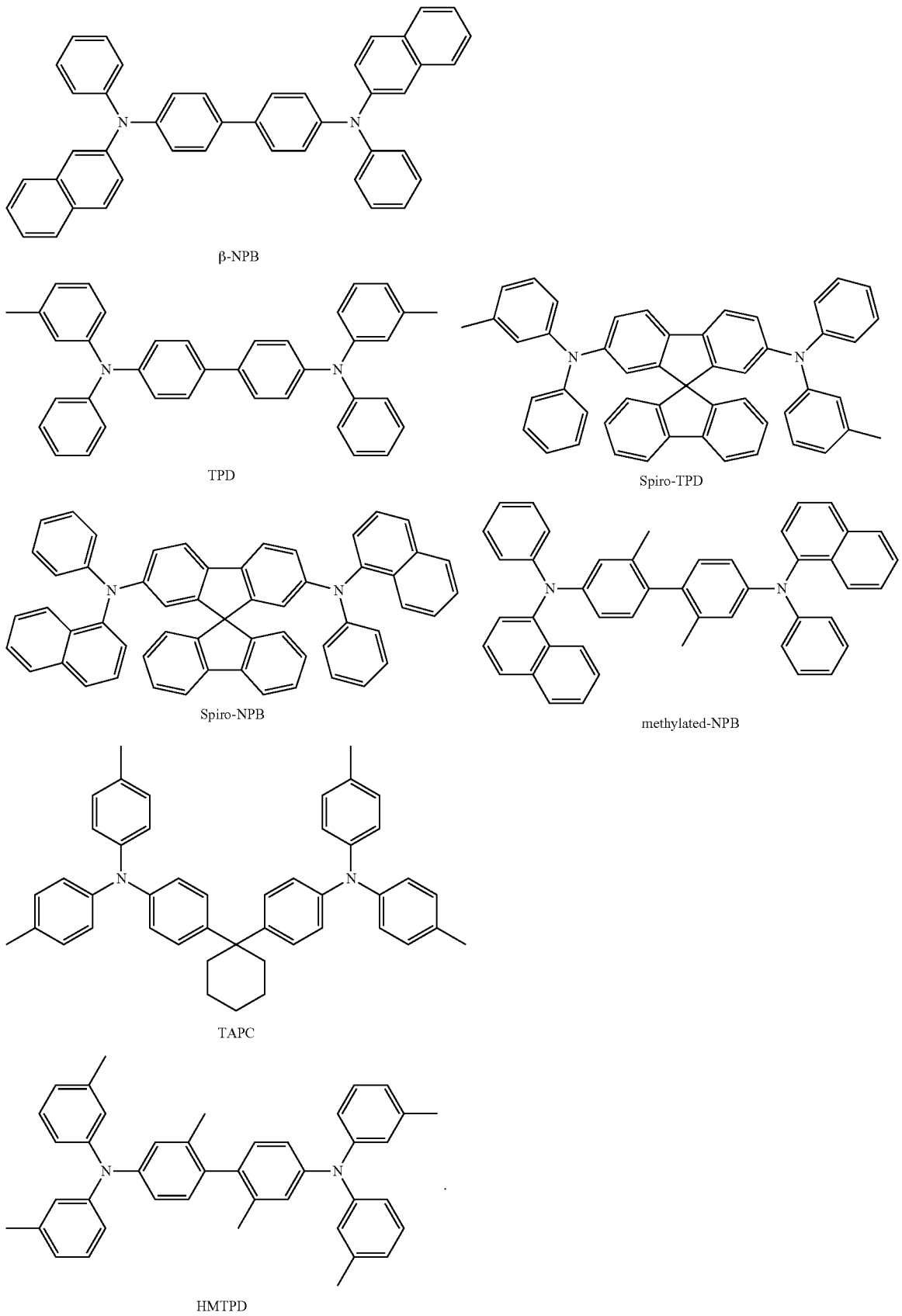

A thickness of the hole transport region may be in a range of about 50 Å to about 10,000 Å. For example, the thickness of the hole transport region may be in a range of about 100 Å to about 4,000 Å. When the hole transport region includes a hole injection layer, a hole transport layer, or any combination thereof, a thickness of the hole injection layer may be in a range of about 100 Å to about 9,000 Å, and a thickness of the hole transport layer may be in a range of about 50 Å to about 2,000 Å. For example, the thickness of the hole injection layer may be in a range of about 100 Å to about 1,000 Å. For example, the thickness of the hole transport layer may be in a range of about 100 Å to about 1,500 Å. When the thicknesses of the hole transport region, the hole injection layer, and the hole transport layer are within these ranges, satisfactory hole transporting characteristics may be obtained without a substantial increase in driving voltage.

The emission auxiliary layer may increase light-emission efficiency by compensating for an optical resonance distance according to the wavelength of light emitted by an emission layer, and the electron blocking layer may block the flow of electrons from an electron transport region. The emission auxiliary layer and the electron blocking layer may include the materials as described above.

[p-Dopant]

The hole transport region may further include, in addition to these materials, a charge-generating material for the improvement of conductive properties. The charge-generating material may be uniformly or non-uniformly dispersed in the hole transport region (for example, in the form of a single layer of a charge-generating material).

The charge-generating material may be, for example, a p-dopant.

In an embodiment, a lowest unoccupied molecular orbital (LUMO) energy level of the p-dopant may be equal to or less than about −3.5 eV.

In an embodiment, the p-dopant may include a quinone derivative, a cyano group-containing compound, a compound containing element EL1 and element EL2, or any combination thereof.

Examples of the quinone derivative may include TCNQ and F4-TCNQ.

Examples of the cyano group-containing compound may include HAT-CN and a compound represented by Formula 221 below.

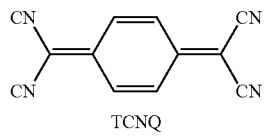

TCNQ

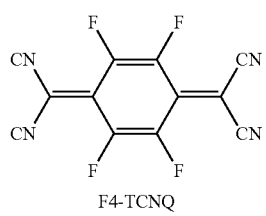

F4-TCNQ

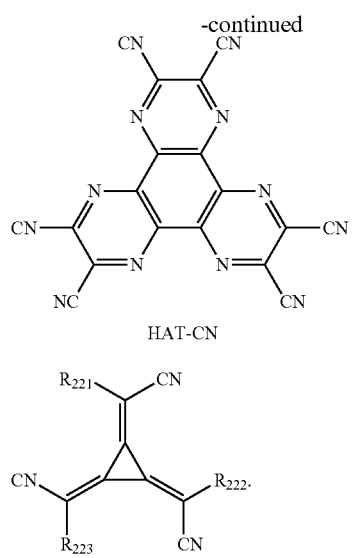

HAT-CN

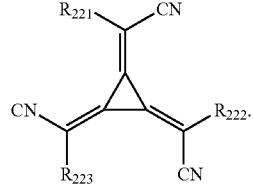

[Formula 221]

In Formula 221, $R_{221}$ to $R_{223}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, at least one of $R_{221}$ to $R_{223}$ may each independently be a $C_3$-$C_{60}$ carbocyclic group or a $C_1$-$C_{60}$ heterocyclic group, each substituted with: a cyano group; —F; —Cl; —Br; —I; a $C_1$-$C_{20}$ alkyl group substituted with a cyano group, —F, —Cl, —Br, —I, or any combination thereof; or any combination thereof.

Regarding the compound containing element EL1 and element EL2, element EL1 may be metal, metalloid, or a combination thereof, and element EL2 may be a non-metal, metalloid, or a combination thereof.

Examples of the metal may include: an alkali metal (for example, lithium (Li), sodium (Na), potassium (K), rubidium (Rb), cesium (Cs), or the like); an alkaline earth metal (for example, beryllium (Be), magnesium (Mg), calcium (Ca), strontium (Sr), barium (Ba), or the like); a transition metal (for example, titanium (Ti), zirconium (Zr), hafnium (Hf), vanadium (V), niobium (Nb), tantalum (Ta), chromium (Cr), molybdenum (Mo), tungsten (W), manganese (Mn), technetium (Tc), rhenium (Re), iron (Fe), ruthenium (Ru), osmium (Os), cobalt (Co), rhodium (Rh), iridium (Ir), nickel (Ni), palladium (Pd), platinum (Pt), copper (Cu), silver (Ag), gold (Au), or the like); a post-transition metal (for example, zinc (Zn), indium (In), tin (Sn), or the like); and a lanthanide metal (for example, lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), lutetium (Lu), or the like).

Examples of the metalloid may include silicon (Si), antimony (Sb), and tellurium (Te).

Examples of the non-metal may include oxygen (O) and halogen (for example, F, Cl, Br, I, etc.).

In an embodiment, examples of the compound containing element EL1 and element EL2 may include metal oxide, metal halide (for example, metal fluoride, metal chloride, metal bromide, or metal iodide), metalloid halide (for example, metalloid fluoride, metalloid chloride, metalloid bromide, or metalloid iodide), metal telluride, or any combination thereof.

Examples of the metal oxide may include tungsten oxide (for example, WO, $W_2O_3$, $WO_2$, $WO_3$, or $W_2O_5$), vanadium oxide (for example, VO, $V_2O_3$, $VO_2$, or $V_2O_5$), molybdenum oxide (for example, MoO, $Mo_2O_3$, $MoO_2$, $MoO_3$, or $Mo_2O_5$), and rhenium oxide (for example, $ReO_3$).

Examples of the metal halide may include alkali metal halide, alkaline earth metal halide, transition metal halide, post-transition metal halide, and lanthanide metal halide.

Examples of the alkali metal halide may include LiF, NaF, KF, RbF, CsF, LiCl, NaCl, KCl, RbCl, CsCl, LiBr, NaBr, KBr, RbBr, CsBr, LiI, NaI, KI, RbI, and CsI.

Examples of the alkaline earth metal halide may include $BeF_2$, $MgF_2$, $CaF_2$, $SrF_2$, $BaF_2$, $BeCl_2$, $MgCl_2$, $CaCl_2$, $SrCl_2$, $BaCl_2$, $BeBr_2$, $MgBr_2$, $CaBr_2$, $SrBr_2$, $BaBr_2$, $BeI_2$, $MgI_2$, $CaI_2$, $SrI_2$, and $BaI_2$.

Examples of the transition metal halide may include titanium halide (for example, $TiF_4$, $TiCl_3$, $TiBr_4$, or $TiI_4$), zirconium halide (for example, $ZrF_4$, $ZrCl_4$, $ZrBr_4$, or $ZrI_4$), hafnium halide (for example, $HfF_4$, $HfCl_4$, $HfBr_4$, or $HfI_4$), vanadium halide (for example, $VF_3$, $VCl_3$, $VBr_3$, or $VI_3$), niobium halide (for example, $NbF_3$, $NbCl_3$, $NbBr_3$, or $NbI_3$), tantalum halide (for example, $TaF_3$, $TaCl_3$, $TaBr_3$, or $TaI_3$), chromium halide (for example, $CrF_3$, $CrCl_3$, $CrBr_3$, or $CrI_3$), molybdenum halide (for example, $MoF_3$, $MoCl_3$, $MoBr_3$, or $MoI_3$), tungsten halide (for example, $WF_3$, $WCl_3$, $WBr_3$, or $WI_3$), manganese halide (for example, $MnF_2$, $MnCl_2$, $MnBr_2$, or $MnI_2$), technetium halide (for example, $TcF_2$, $TcCl_2$, $TcBr_2$, or $TcI_2$), rhenium halide (for example, $ReF_2$, $ReCl_2$, $ReBr_2$, or $ReI_2$), iron halide (for example, $FeF_2$, $FeCl_2$, $FeBr_2$, or $FeI_2$), ruthenium halide (for example, $RuF_2$, $RuCl_2$, $RuBr_2$, or $RuI_2$), osmium halide (for example, $OsF_2$, $OsCl_2$, $OsBr_2$, or $OsI_2$), cobalt halide (for example, $CoF_2$, $CoCl_2$, $CoBr_2$, or $CoI_2$), rhodium halide (for example, $RhF_2$, $RhCl_2$, $RhBr_2$, or $RhI_2$), iridium halide (for example, $IrF_2$, $IrCl_2$, $IrBr_2$, or $IrI_2$), nickel halide (for example, $NiF_2$, $NiCl_2$, $NiBr_2$, or $NiI_2$), palladium halide (for example, $PdF_2$, $PdCl_2$, $PdBr_2$, or $PdI_2$), platinum halide (for example, $PtF_2$, $PtCl_2$, $PtBr_2$, or $PtI_2$), copper halide (for example, CuF, CuCl, CuBr, or CuI), silver halide (for example, AgF, AgCl, AgBr, or AgI), and gold halide (for example, AuF, AuCl, AuBr, or AuI).

Examples of the post-transition metal halide may include zinc halide (for example, $ZnF_2$, $ZnCl_2$, $ZnBr_2$, or $ZnI_2$), indium halide (for example, $InI_3$), and tin halide (for example, $SnI_2$).

Examples of the lanthanide metal halide may include YbF, $YbF_2$, $YbF_3$, $SmF_3$, YbCl, $YbCl_2$, $YbCl_3$, $SmCl_3$, YbBr, $YbBr_2$, $YbBr_3$, $SmBr_3$, YbI, $YbI_2$, $YbI_3$, and $SmI_3$.

Examples of the metalloid halide may include antimony halide (for example, $SbCl_5$).

Examples of the metal telluride may include an alkali metal telluride (for example, $Li_2Te$, $Na_2Te$, $K_2Te$, $Rb_2Te$, or $Cs_2Te$), alkaline earth metal telluride (for example, BeTe, MgTe, CaTe, SrTe, or BaTe), transition metal telluride (for example, $TiTe_2$, $ZrTe_2$, $HfTe_2$, $V_2Te_3$, $Nb_2Te_3$, $Ta_2Te_3$, $Cr_2Te_3$, $Mo_2Te_3$, $W_2Te_3$, MnTe, TcTe, ReTe, FeTe, RuTe, OsTe, CoTe, RhTe, IrTe, NiTe, PdTe, PtTe, $Cu_2Te$, CuTe, $Ag_2Te$, AgTe, or $Au_2Te$), post-transition metal telluride (for example, ZnTe), and lanthanide metal telluride (for example, LaTe, CeTe, PrTe, NdTe, PmTe, EuTe, GdTe, TbTe, DyTe, HoTe, ErTe, TmTe, YbTe, or LuTe).

[Emission Layer in Interlayer 130]

When the light-emitting device 10 is a full-color light-emitting device, the emission layer may be patterned into a red emission layer, a green emission layer, and/or a blue emission layer, according to a sub-pixel. In embodiments, the emission layer may have a stacked structure of two or more layers of a red emission layer, a green emission layer, and a blue emission layer, in which the two or more layers contact each other or are separated from each other to emit white light. In embodiments, the emission layer may include two or more materials of a red light-emitting material, a green light-emitting material, and a blue light-emitting material, in which the two or more materials are mixed with each other in a single layer to emit white light.

The emission layer may include a host and a dopant. The dopant may include a phosphorescent dopant, a fluorescent dopant, or any combination thereof.

An amount of the dopant in the emission layer may be in a range of about 0.01 to about 15 parts by weight based on 100 parts by weight of the host.

In embodiments, the emission layer may include a quantum dot.

In an embodiment, the emission layer may include a delayed fluorescence material. The delayed fluorescence material may act as a host or a dopant in the emission layer.

A thickness of the emission layer may be in a range of about 100 Å to about 1,000 Å. For example, the thickness of the emission layer may be in a range of about 200 Å to about 600 Å. When the thickness of the emission layer is within this range, excellent luminescence characteristics may be obtained without a substantial increase in driving voltage.

[Host]

The host may include a compound represented by Formula 301 below:

$$[Ar_{301}]_{xb11}-[(L_{301})_{xb1}-R_{301}]_{xb21} \qquad [\text{Formula 301}]$$

In Formula 301, $Ar_{301}$ and $L_{301}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, xb11 may be 1, 2, or 3, xb1 may be an integer from 0 to 5, $R_{301}$ may be hydrogen, deuterium, —F, —Cl, —Br, —I, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, —Si($Q_{301}$)($Q_{302}$)($Q_{303}$), —N($Q_{301}$)($Q_{302}$), —B($Q_{301}$)($Q_{302}$), —C(=O)($Q_{301}$), —S(=O)$_2$($Q_{301}$), or —P(=O)($Q_{301}$)($Q_{302}$), xb21 may be an integer from 1 to 5, and $Q_{301}$ to $Q_{303}$ are the same as described in connection with $Q_1$.

In an embodiment, when xb11 in Formula 301 is 2 or more, two or more of $Ar_{301}$(s) may be linked to each other via a single bond.

In an embodiment, the host may include a compound represented by Formula 301-1, a compound represented by Formula 301-2, or any combination thereof:

[Formula 301-1]

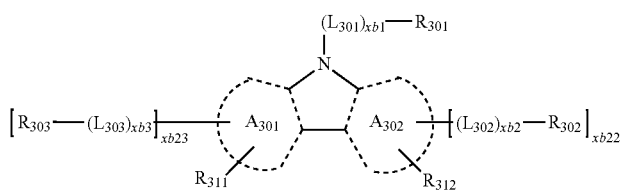

[Formula 301-2]

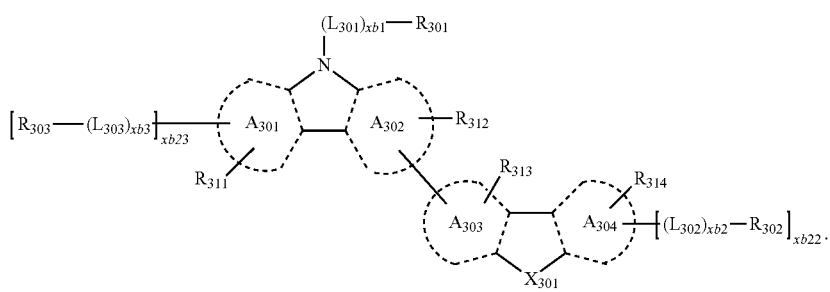

In Formulae 301-1 and 301-2,
ring $A_{301}$ to ring $A_{304}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$,
$X_{301}$ may be O, S, N-[$(L_{304})_{xb4}$-$R_{304}$], $C(R_{304})(R_{305})$, or $Si(R_{304})(R_{305})$,
xb22 and xb23 may each independently be 0, 1, or 2,
$L_{301}$, xb1, and $R_{301}$ are the same as described in the specification,
$L_{302}$ to $L_{304}$ are each independently the same as described in connection with $L_{301}$,
xb2 to xb4 are each independently the same as described in connection with xb1, and
$R_{302}$ to $R_{305}$ and $R_{311}$ to $R_{314}$ are the same as described in connection with $R_{301}$.

In an embodiment, the host may include an alkaline earth-metal complex. In an embodiment, the host may include a Be complex (for example, Compound H55), a Mg complex, a Zn complex, or any combination thereof.

In an embodiment, the host may include one of Compounds H1 to H124, 9,10-di(2-naphthyl)anthracene (ADN), 2-methyl-9,10-bis(naphthalen-2-yl)anthracene (MADN), 9,10-di-(2-naphthyl)-2-t-butyl-anthracene (TBADN), 4,4'-bis(N-carbazolyl)-1,1'-biphenyl (CBP), 1,3-di(carbazol-9-yl)benzene (mCP), 1,3,5-tri(carbazol-9-yl)benzene (TCP), or any combination thereof:

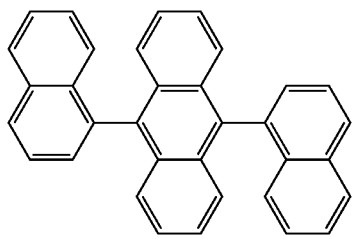

H1

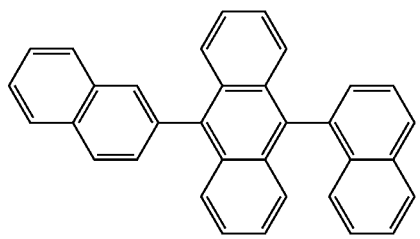

H2

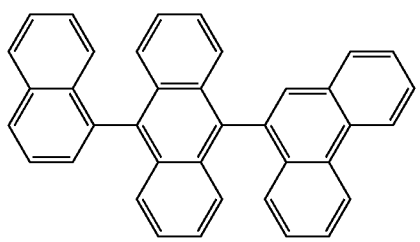

H3

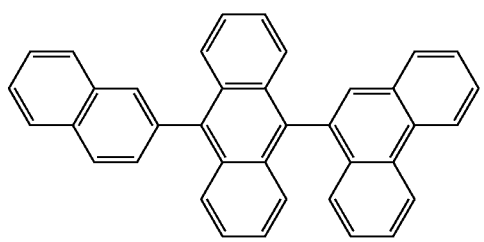

H4

-continued
H5
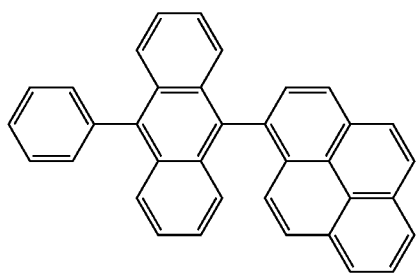
H6
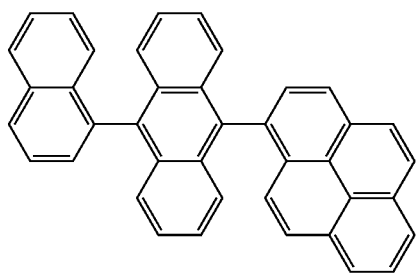
H7
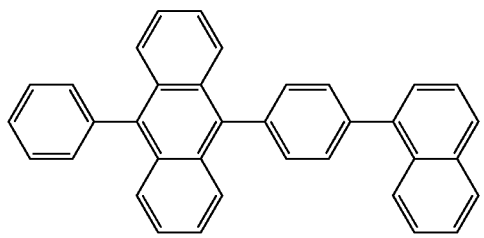
H8
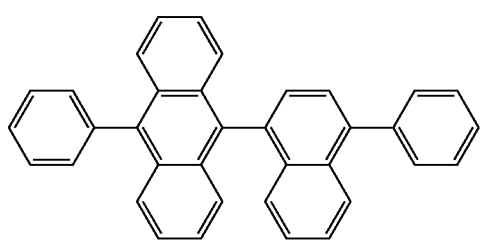
H9
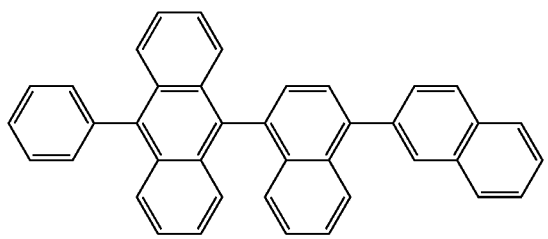
H10
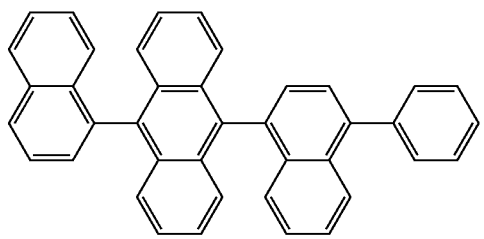
H11
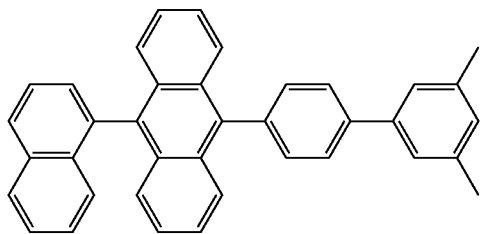
H12
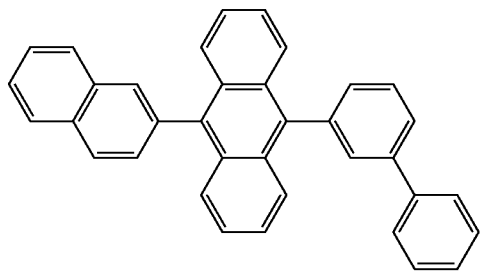
H13
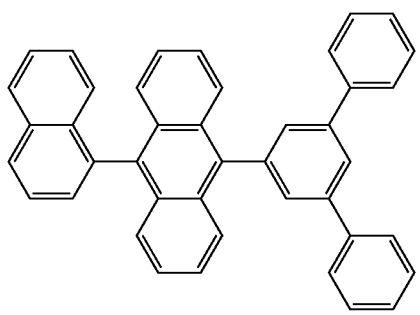
H14
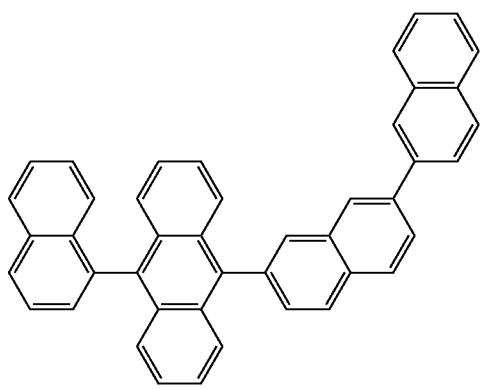

-continued
H15
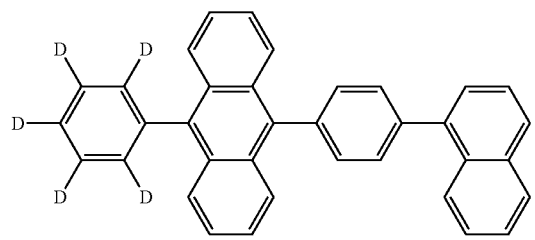
H16
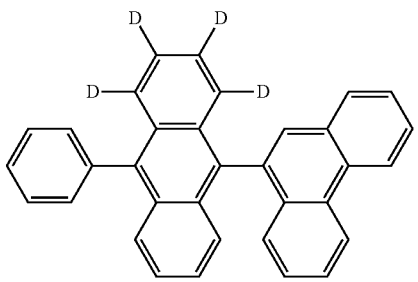
H17
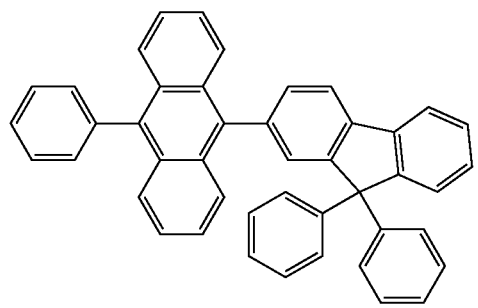
H18
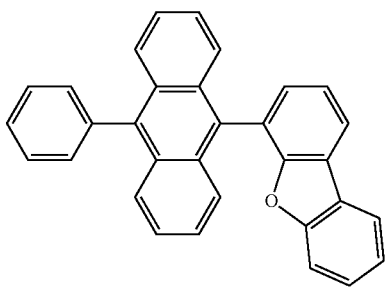
H19
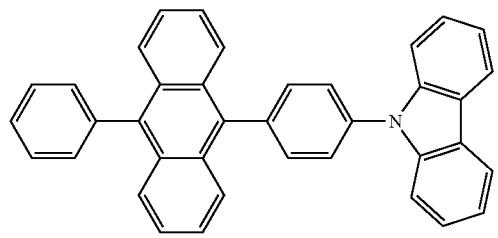
H20
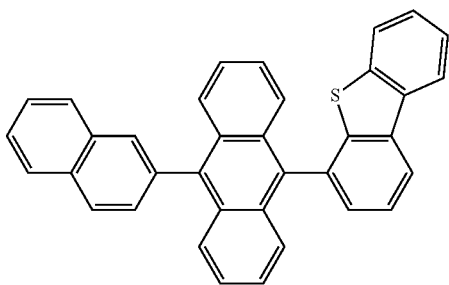
H21
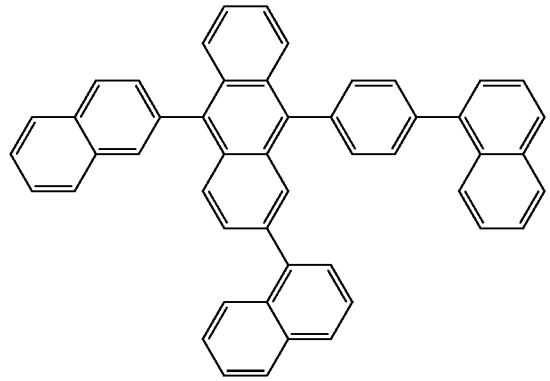
H22
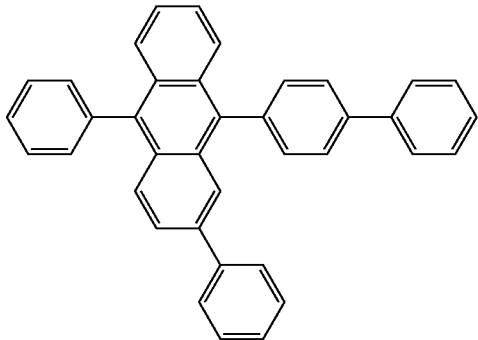

-continued
H23
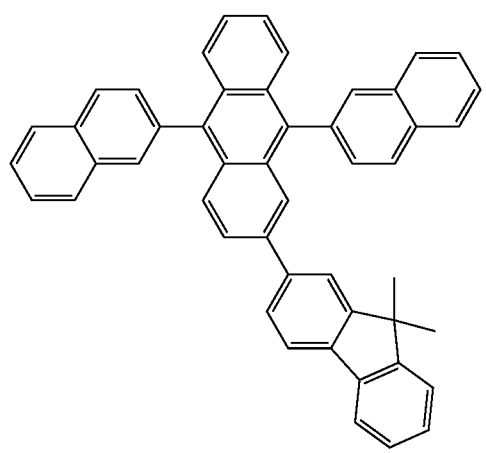
H24
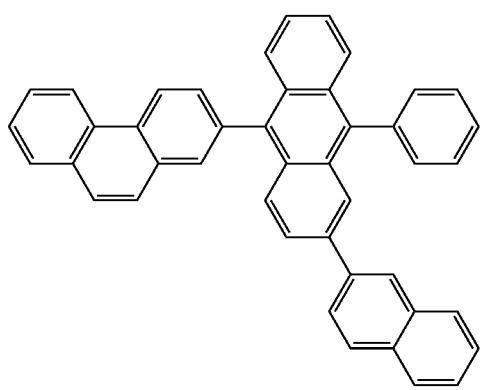
H25
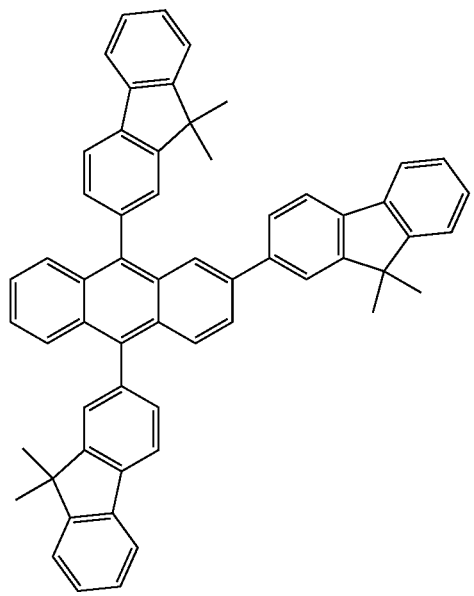
H26
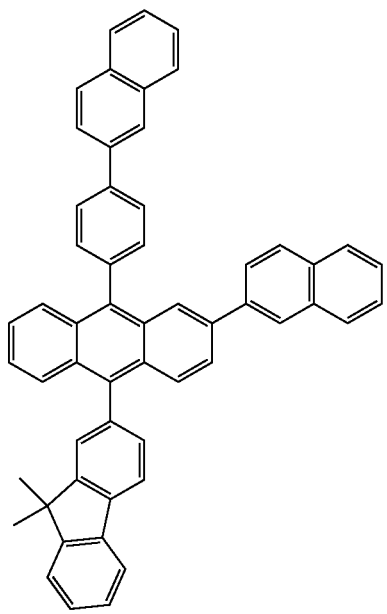
H27
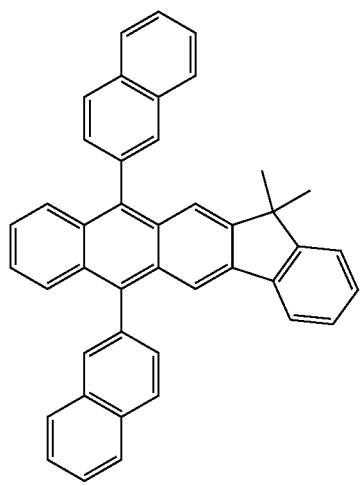
H28
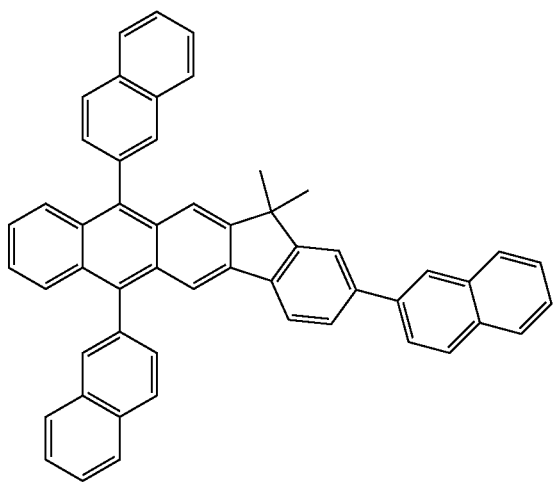

-continued
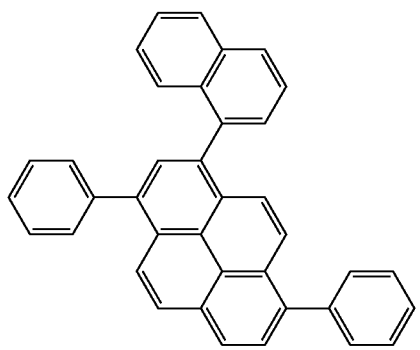
H29
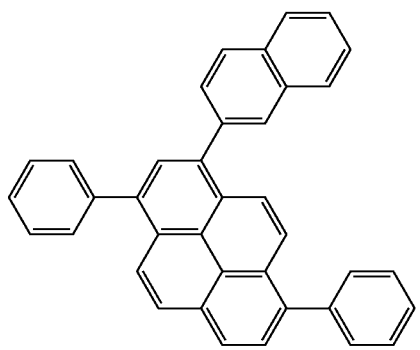
H30
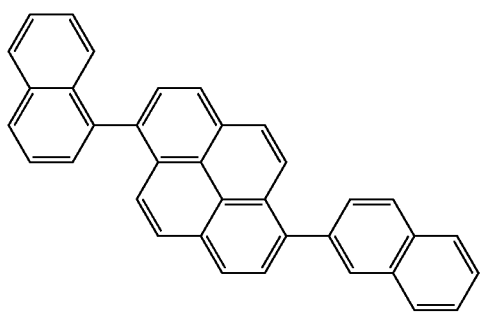
H31
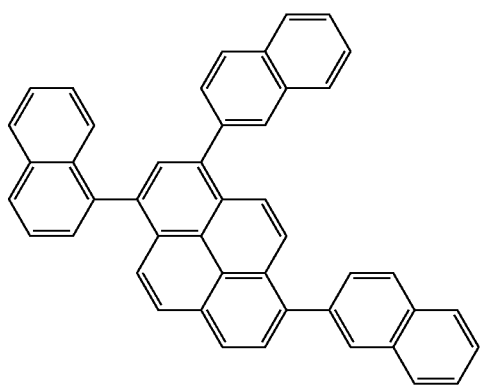
H32
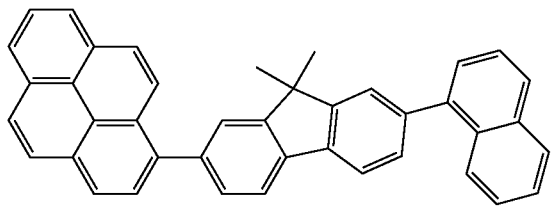
H33
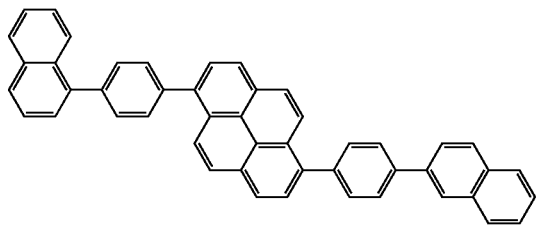
H34
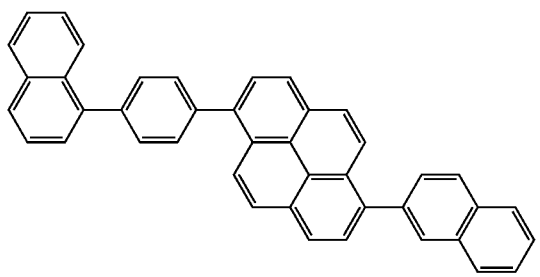
H35
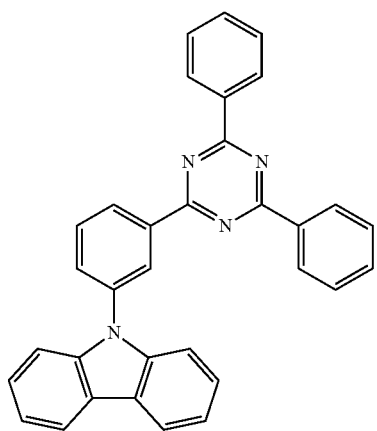
H36

-continued
H37
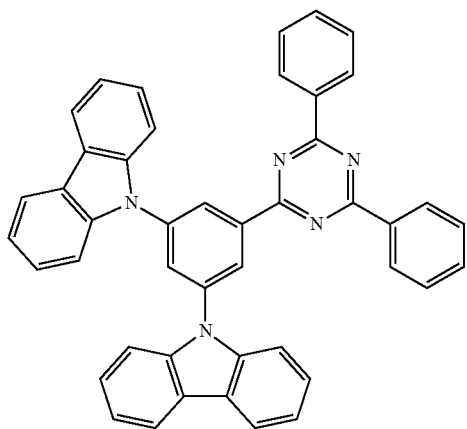
H38
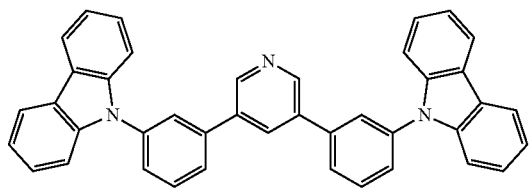
H39
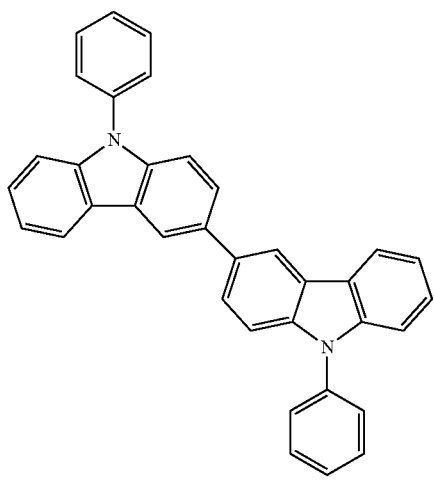
H40
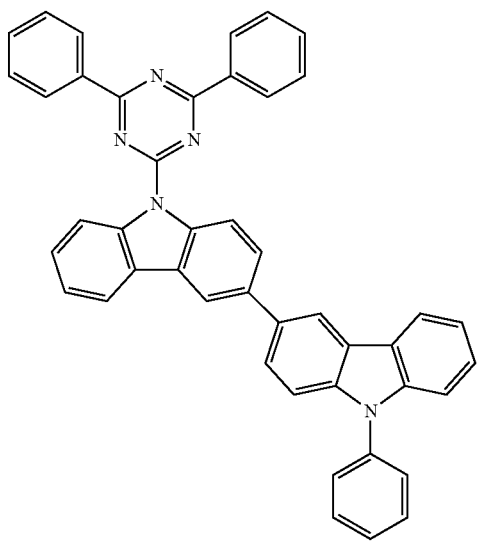
H41
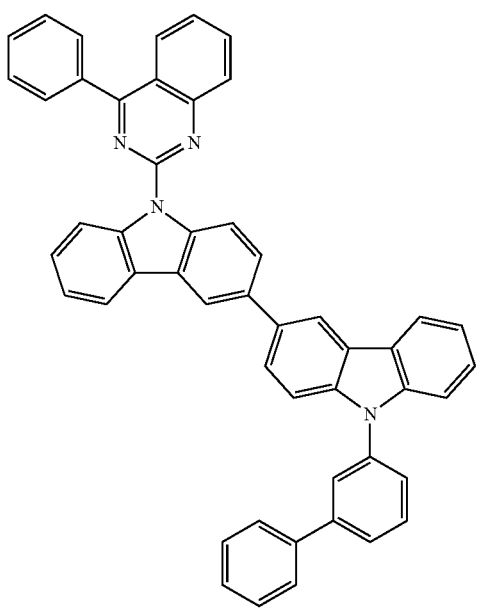
H42
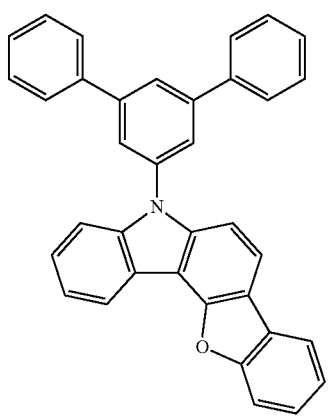

-continued
H43
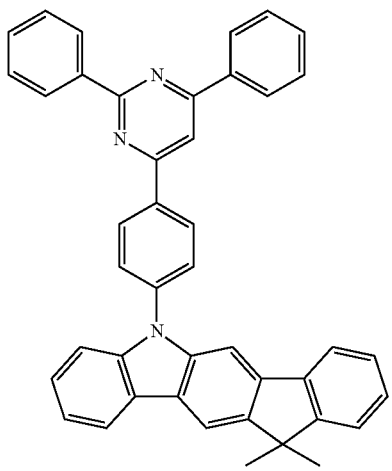
H44
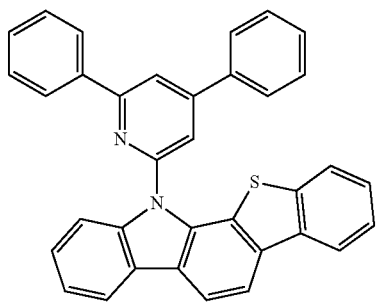
H45
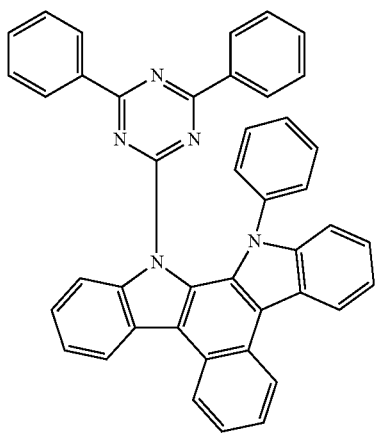
H46
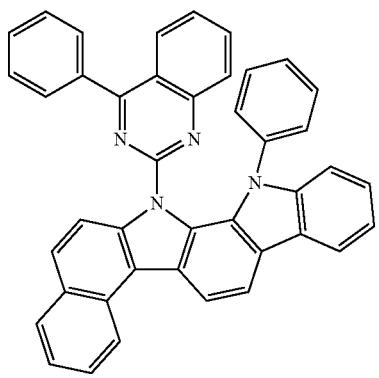
H47
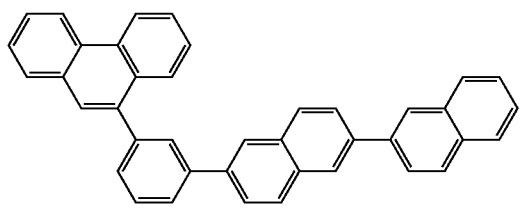
H48
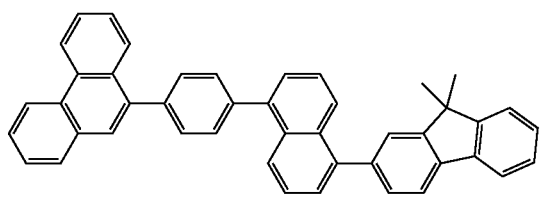
H49
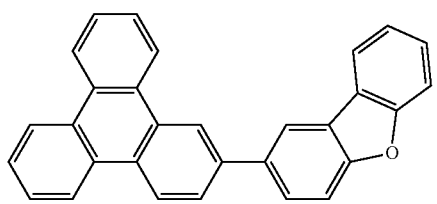
H50
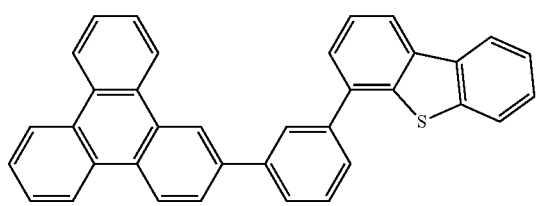

-continued
H51
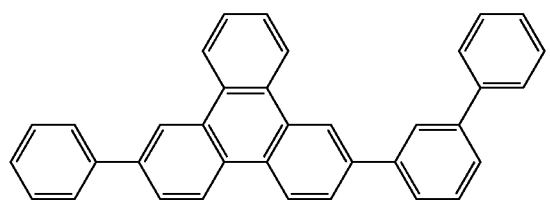
H52
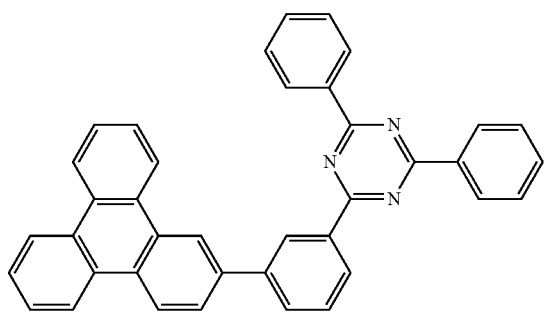
H53
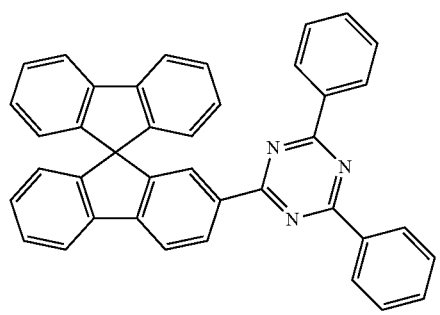
H54
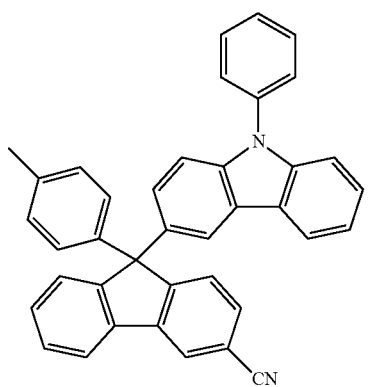
H55
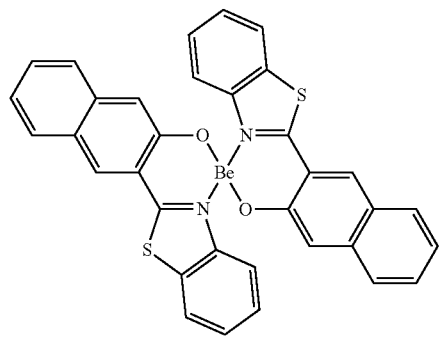
H56
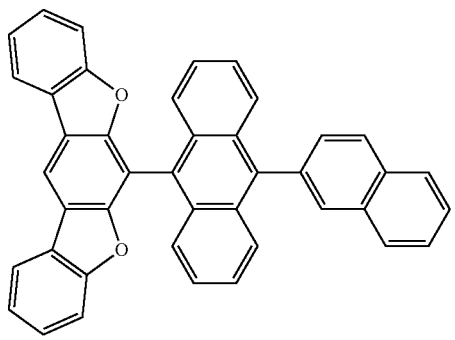
H57
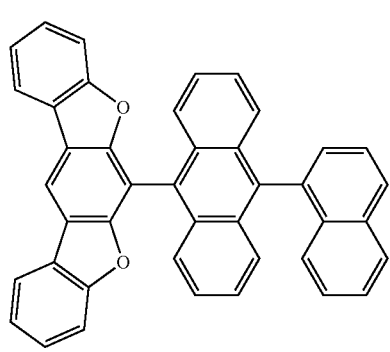
H58
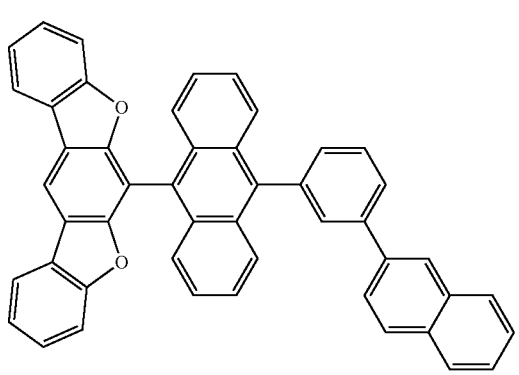

-continued
H59
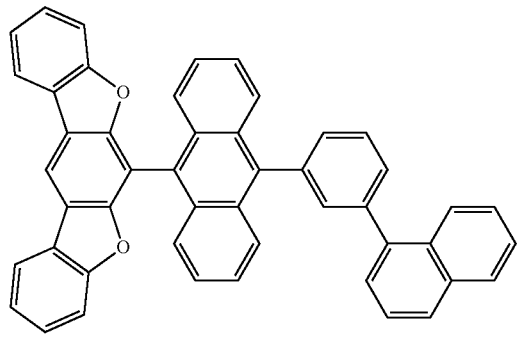
H60
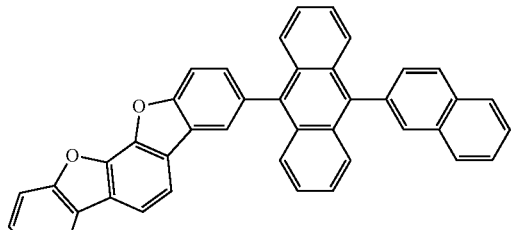
H61
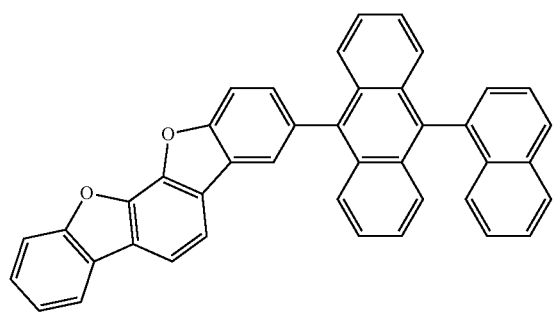
H62
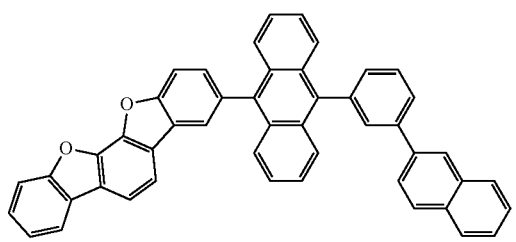
H63
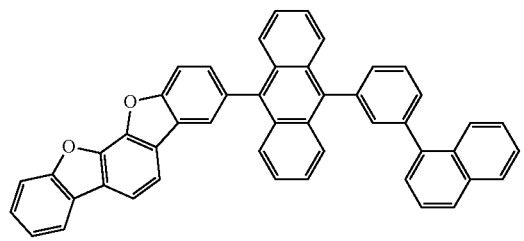
H64
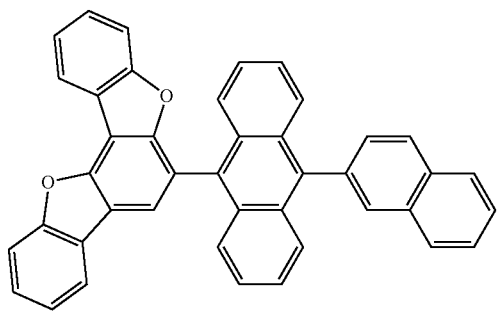
H65
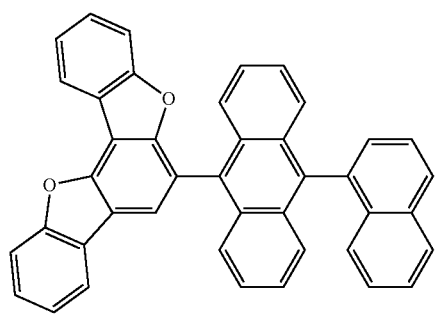
H66
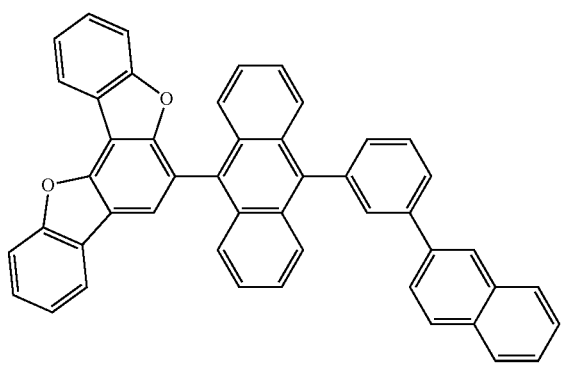

-continued
H67
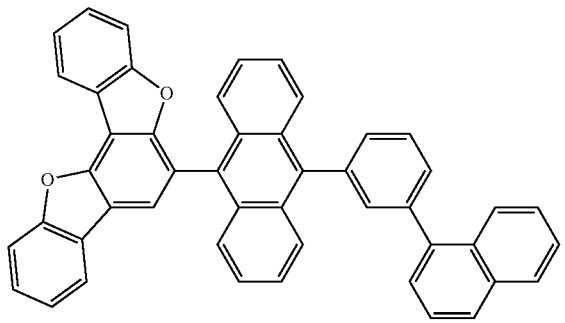
H68
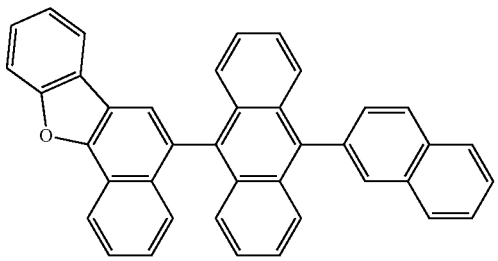
H69
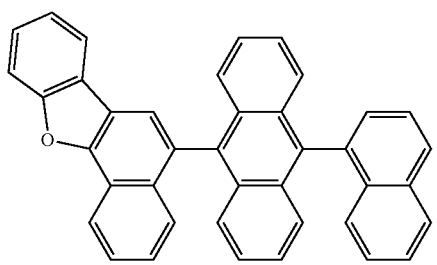
H70
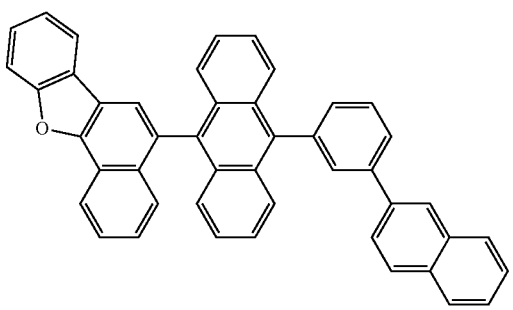
H71
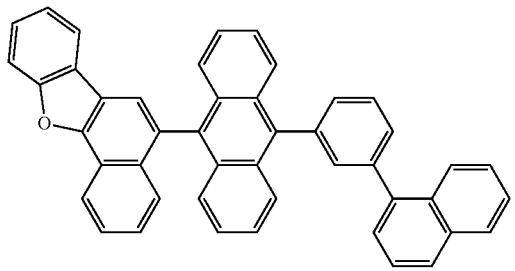
H72
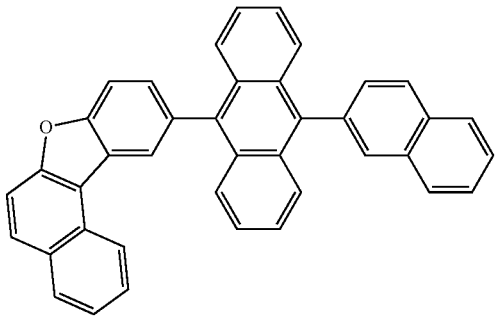
H73
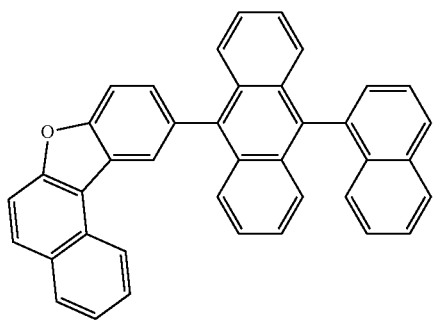
H74
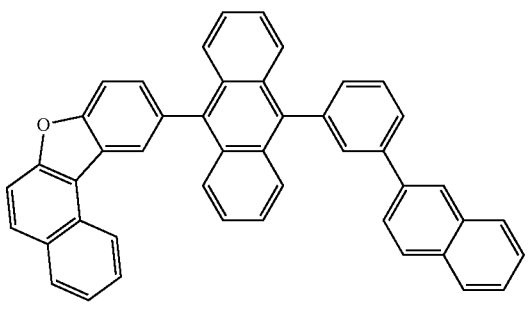
H75
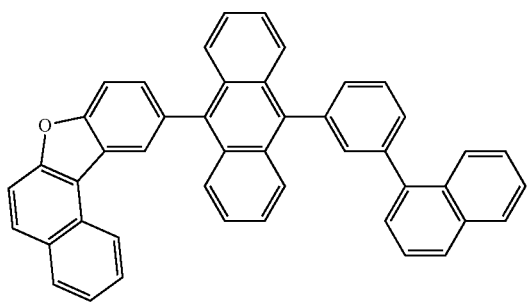
H76
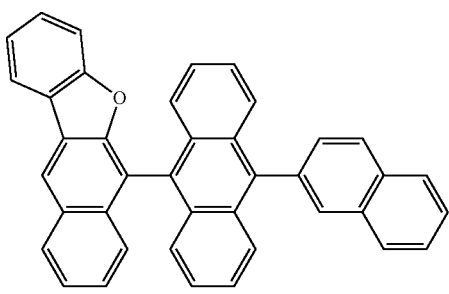

-continued
H77
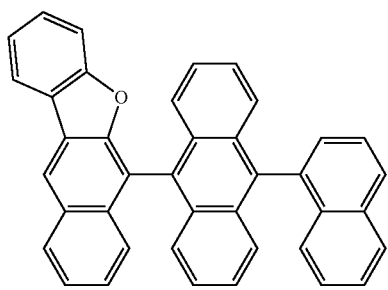
H78
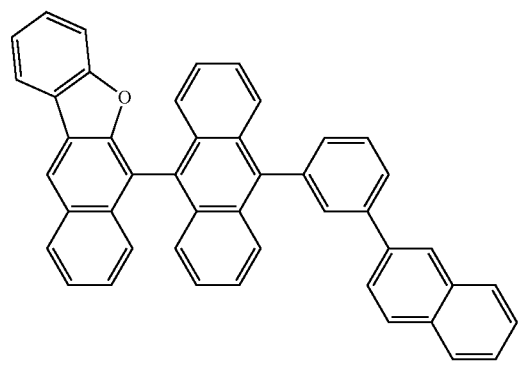
H79
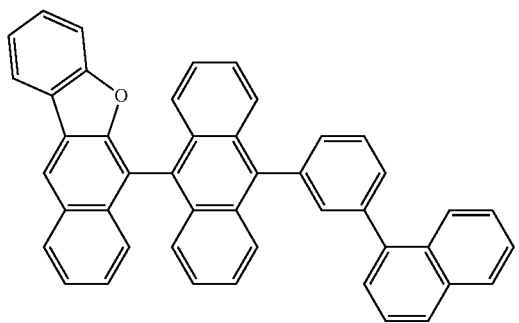
H80
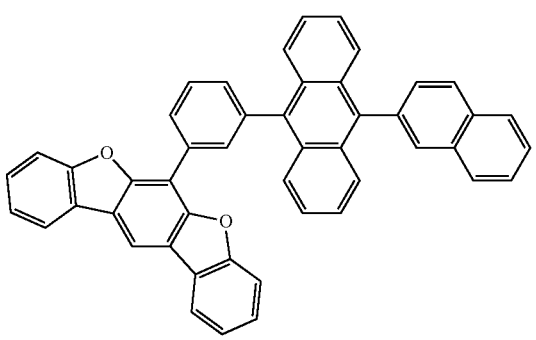
H81
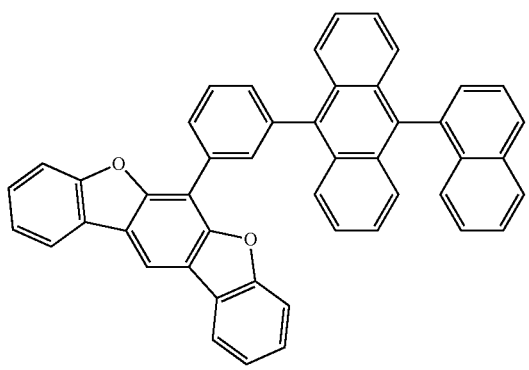
H82
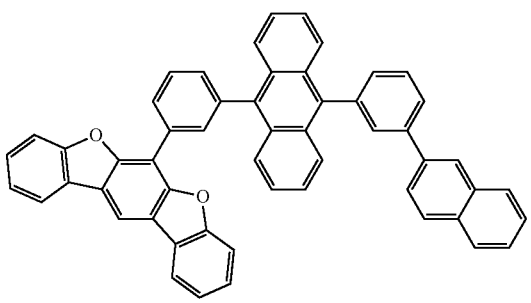
H83
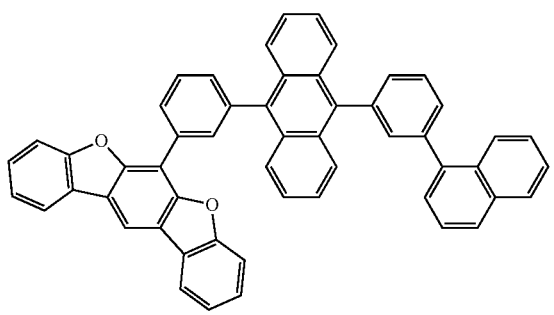
H84
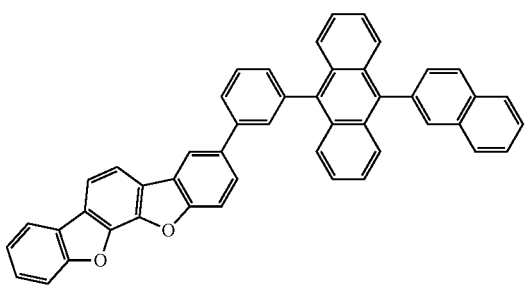

-continued
H85
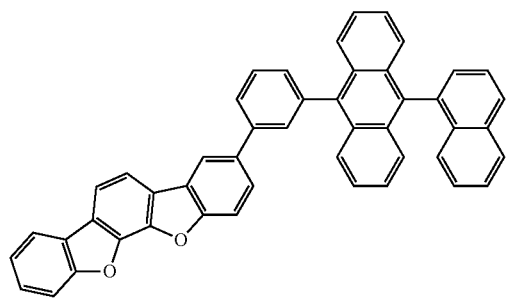
H86
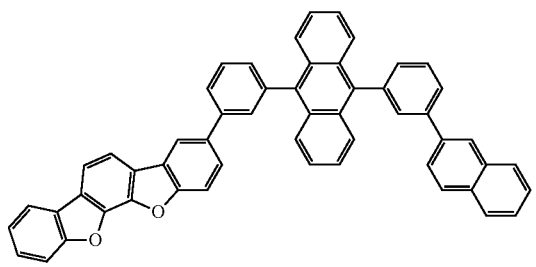
H87
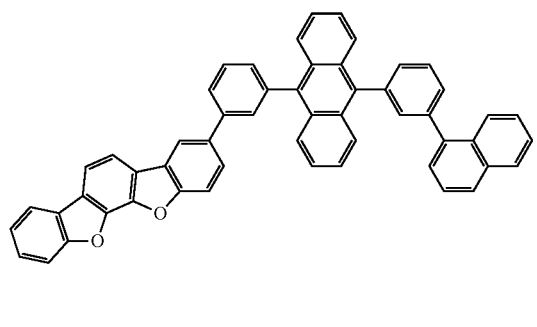
H88
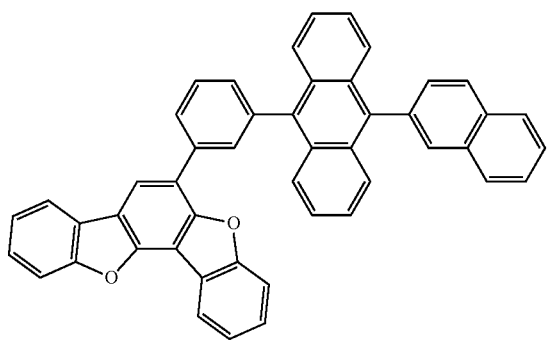
H89
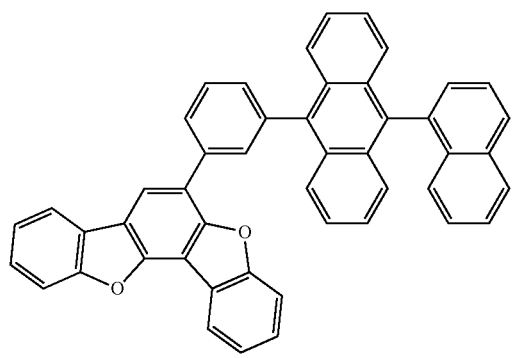
H90
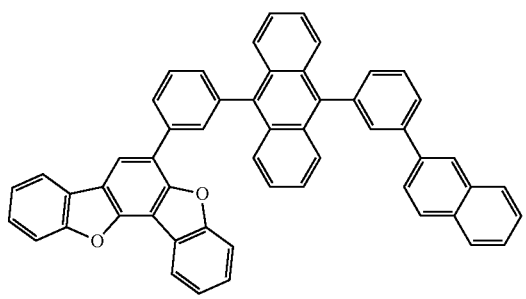
H91
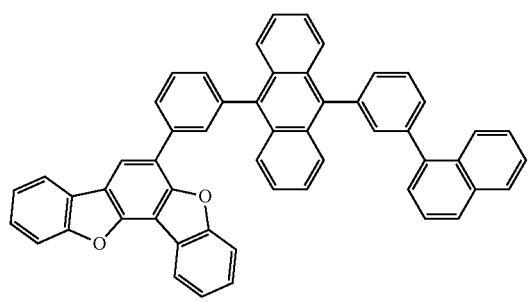
H92
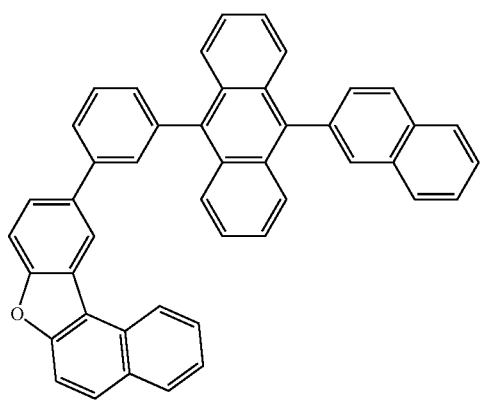

-continued

H93

H94

H95

H96

H97

H98

H99

H100

-continued
H101
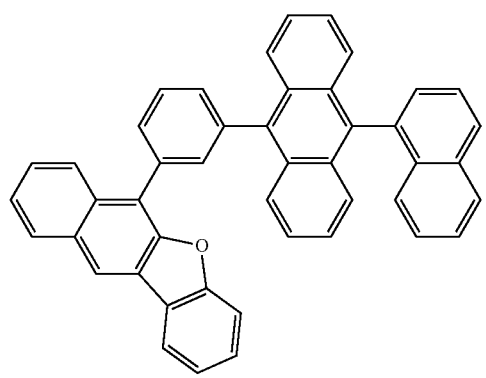
H102
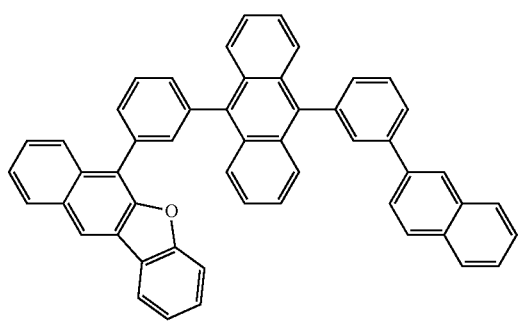
H103
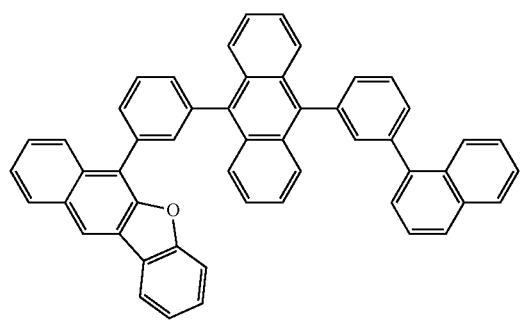
H104
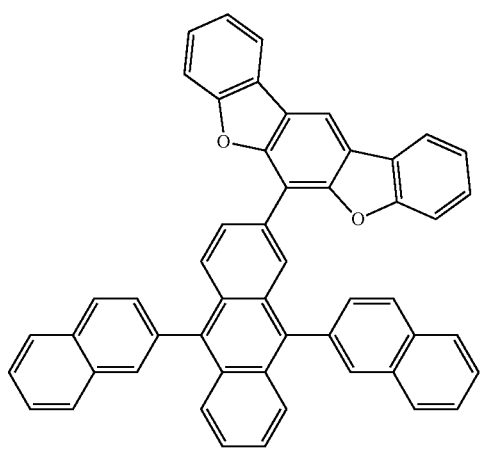
H105
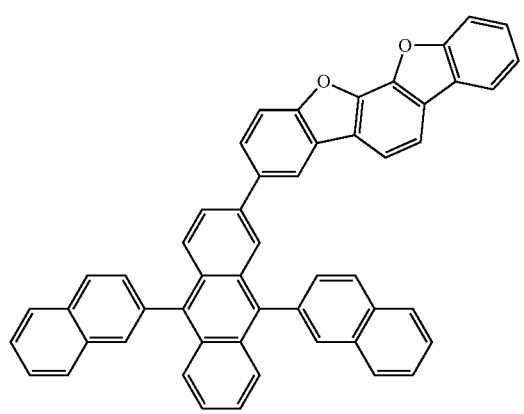
H106
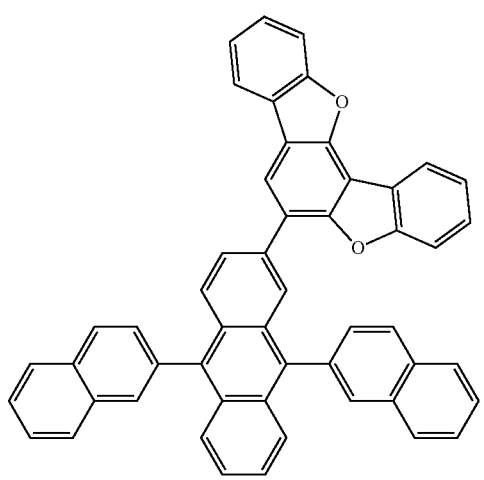

-continued
H107
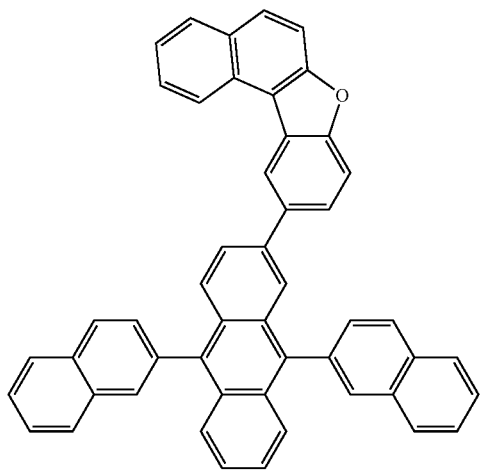
H108
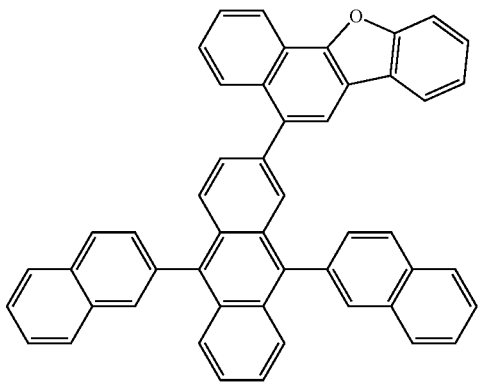
H109
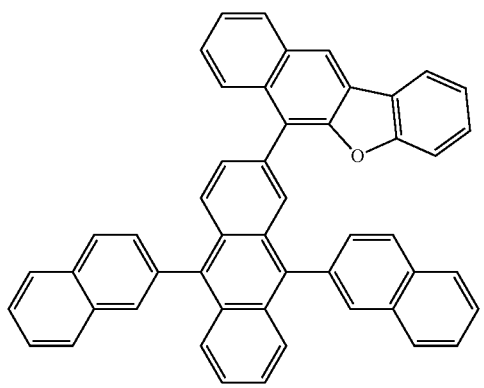
H110
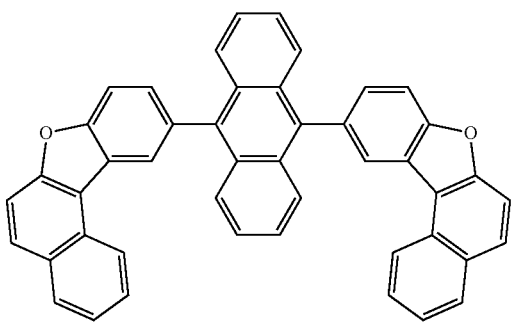
H111
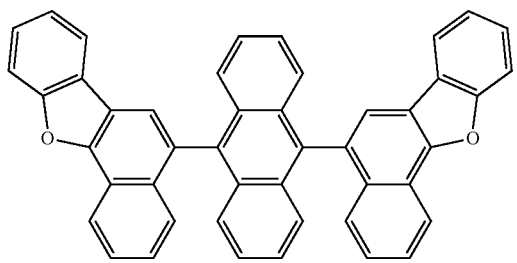
H112
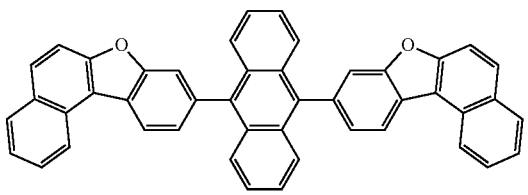
H113
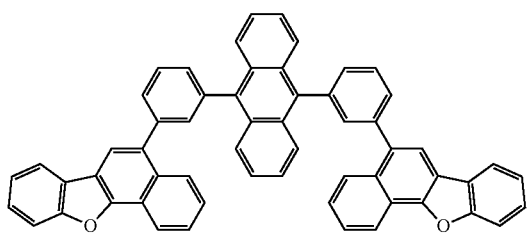

H114
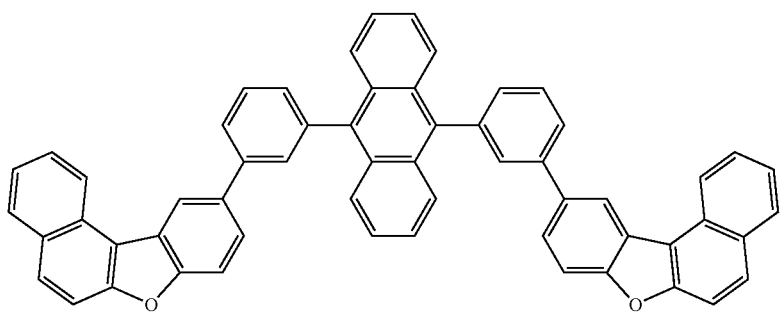
H115
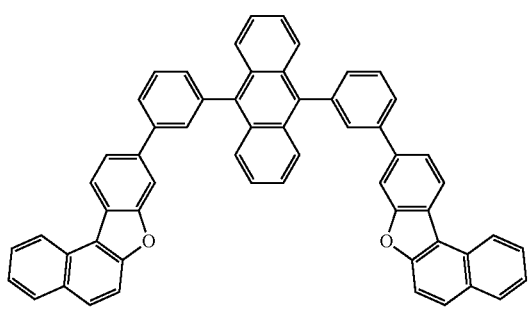
H116
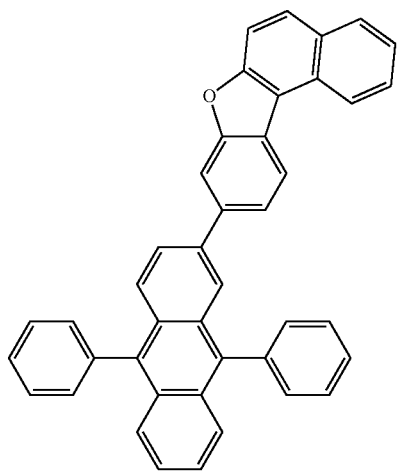
H117
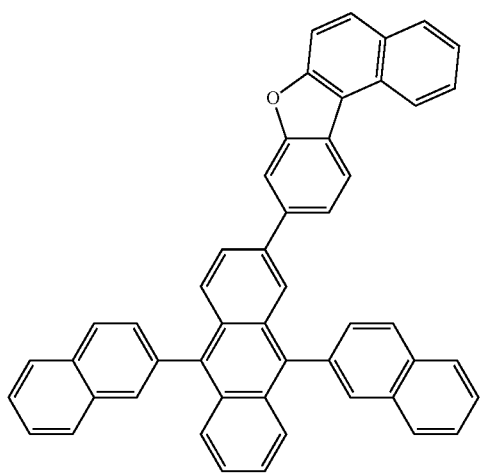
H118
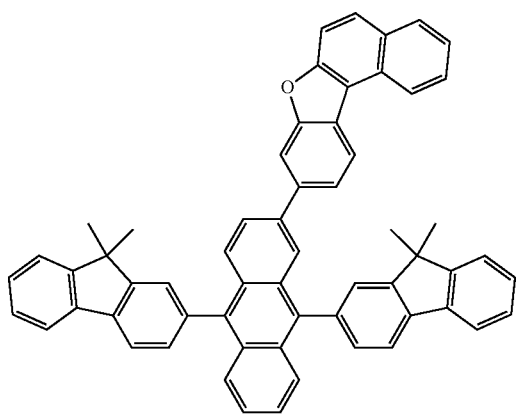

-continued
H119
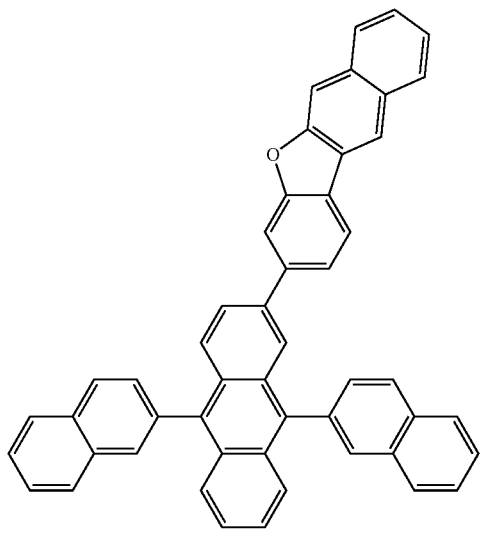
H120
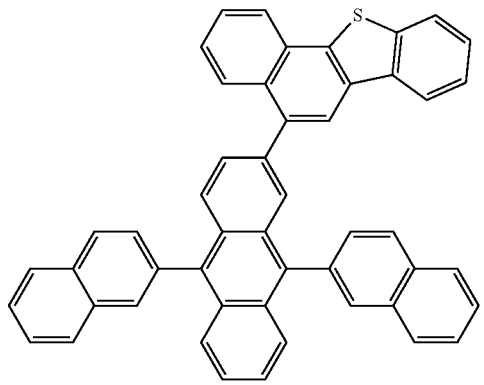
H121
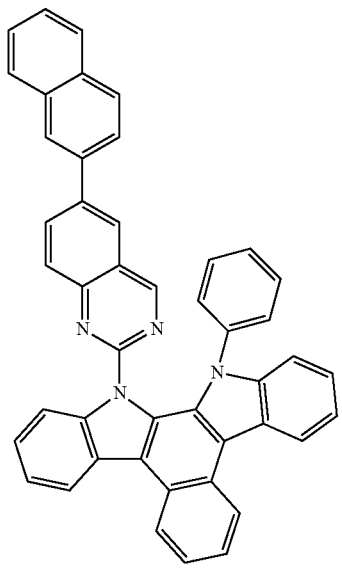
H122
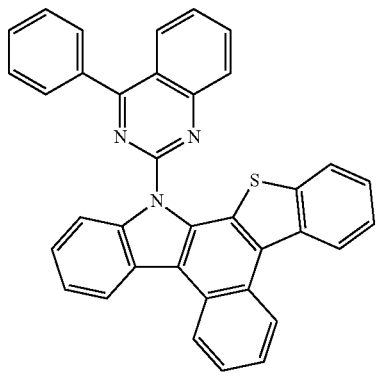
H123
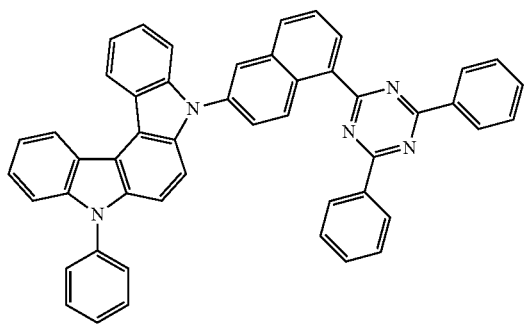
H124
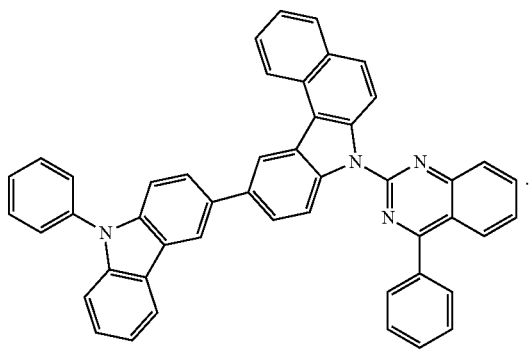

[Phosphorescent Dopant]

The phosphorescent dopant may include at least one transition metal as a central metal.

The phosphorescent dopant may include a monodentate ligand, a bidentate ligand, a tridentate ligand, a tetradentate ligand, a pentadentate ligand, a hexadentate ligand, or any combination thereof.

The phosphorescent dopant may be electrically neutral.

In an embodiment, the phosphorescent dopant may include an organometallic compound represented by Formula 401:

$$M(L_{401})_{xc1}(L_{402})_{xc2}$$ [Formula 401]

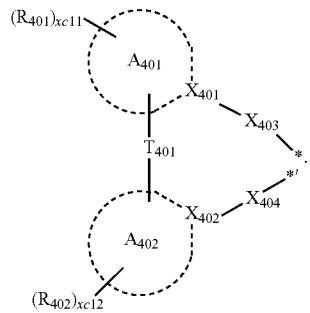

[Formula 402]

In Formulae 401 and 402,

M may be a transition metal (for example, iridium (Ir), platinum (Pt), palladium (Pd), osmium (Os), titanium (Ti), gold (Au), hafnium (Hf), europium (Eu), terbium (Tb), rhodium (Rh), rhenium (Re), or thulium (Tm)), $L_{401}$ may be a ligand represented by Formula 402, and xc1 may be 1, 2, or 3, wherein, when xc1 is 2 or more, two or more of $L_{401}$(s) may be identical to or different from each other, $L_{402}$ may be an organic ligand, and xc2 may be 0, 1, 2, 3, or 4, wherein, when xc2 is 2 or more, two or more of $L_{402}$(s) may be identical to or different from each other, $X_{401}$ and $X_{402}$ may each independently be nitrogen or carbon, ring $A_{401}$ and ring $A_{402}$ may each independently be a $C_3$-$C_{60}$ carbocyclic group or a $C_1$-$C_{60}$ heterocyclic group, $T_{401}$ may be a single bond, *—C(=O)—*', *—N($Q_{411}$)-*', *—C($Q_{411}$)($Q_{412}$)-*', *—C($Q_{411}$)=C($Q_{412}$)-*', *—C($Q_{411}$)=*', or *=C=*', $X_{403}$ and $X_{404}$ may each independently be a chemical bond (for example, a covalent bond or a coordinate bond), O, S, N($Q_{413}$), B($Q_{413}$), P($Q_{413}$), C($Q_{413}$)($Q_{414}$), or Si($Q_{413}$)($Q_{414}$), $Q_{411}$ to $Q_{414}$ are the same as described in connection with $Q_1$ in the specification, $R_{401}$ and $R_{402}$ may each independently be hydrogen, deuterium, —F, —Cl, —Br, —I, a hydroxyl group, a cyano group, a nitro group, a $C_1$-$C_{20}$ alkyl group unsubstituted or substituted with at least one $R_{10a}$, a $C_1$-$C_{20}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, —Si($Q_{401}$)($Q_{402}$)($Q_{403}$), —N($Q_{401}$)($Q_{402}$), —B($Q_{401}$)($Q_{402}$), —C(=O)($Q_{401}$), —S(=O)$_2$($Q_{401}$), or —P(=O)($Q_{401}$)($Q_{402}$), $Q_{401}$ to $Q_{403}$ are the same as described in connection with $Q_1$ in the specification, xc11 and xc12 may each independently be an integer from 0 to 10, and and *' in Formula 402 may each indicate a binding site to M in Formula 401.

In an embodiment, in Formula 402, i) $X_{401}$ may be nitrogen, and $X_{402}$ may be carbon, or ii) both $X_{401}$ and $X_{402}$ may be nitrogen.

In an embodiment, when xc1 in Formula 401 is 2 or more, two ring $A_{401}$(s) in two or more $L_{401}$(s) may optionally be linked to each other via $T_{402}$, which is a linking group, or two ring $A_{402}$(s) in two or more $L_{401}$(s) may optionally be linked to each other via $T_{403}$, which is a linking group (see Compounds PD1 to PD4 and PD7). $T_{402}$ and $T_{403}$ are the same as described in connection with $T_{401}$ in the specification.

$L_{402}$ in Formula 401 may be an organic ligand. For example, $L_{402}$ may include a halogen group, a diketone group (for example, an acetylacetonate group), a carboxylic acid group (for example, a picolinate group), —C(=O), a isonitrile group, a —CN group, a phosphorus group (for example, a phosphine group and a phosphite group), or any combination thereof.

The phosphorescent dopant may include, for example, one of following Compounds PD1 to PD25 or any combination thereof:

PD1

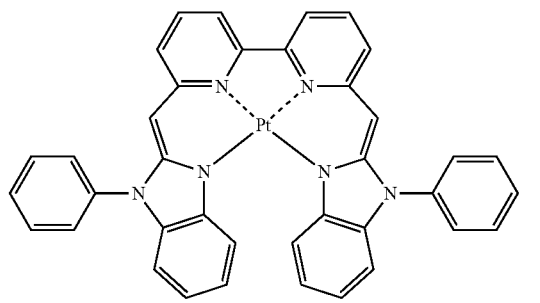

PD2

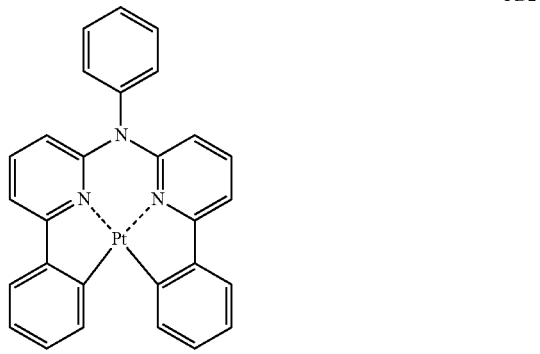

PD3

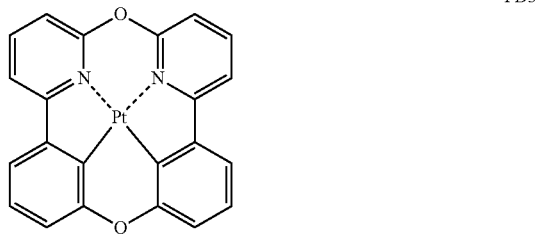

-continued
PD4
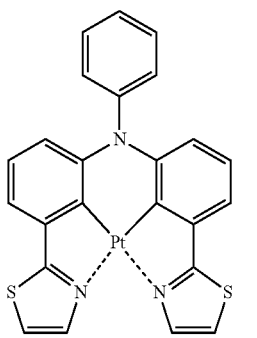
PD5
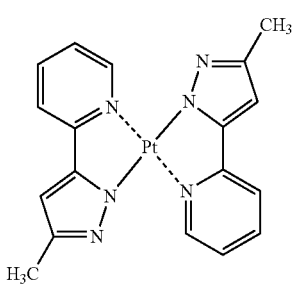
PD6
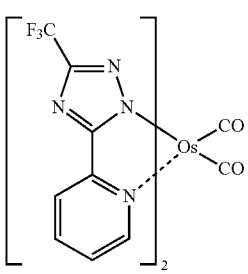
PD7
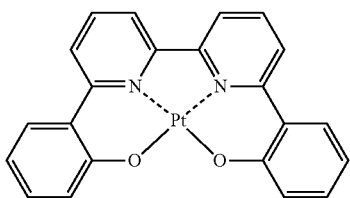
PD8
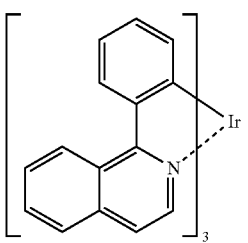
PD9
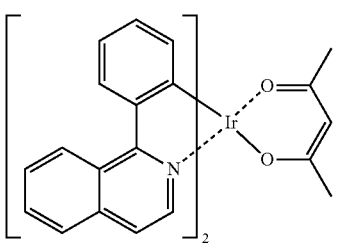
-continued
PD10
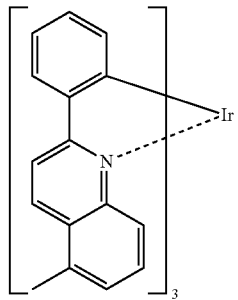
PD11
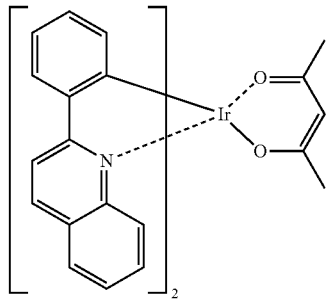
PD12
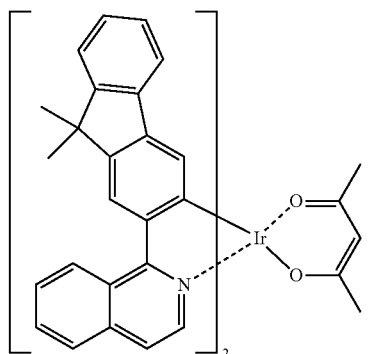
PD13
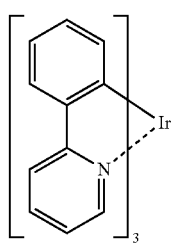
PD14
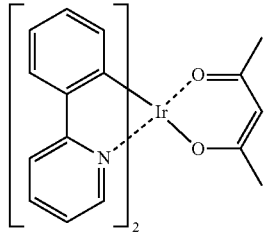

PD15 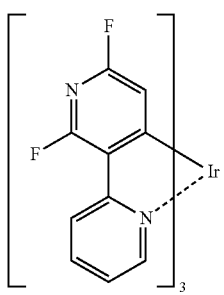
PD16 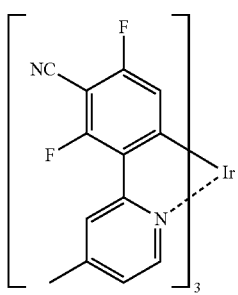
PD17 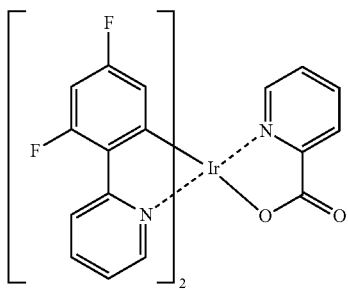
PD18 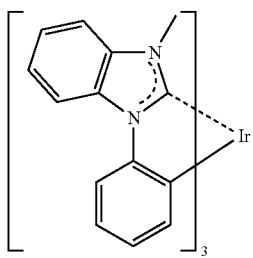
PD19 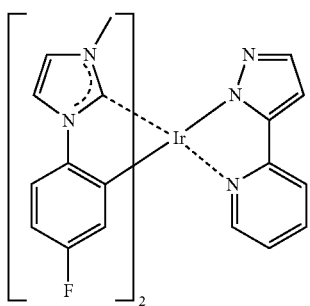
PD20 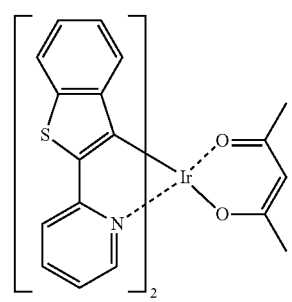
PD21 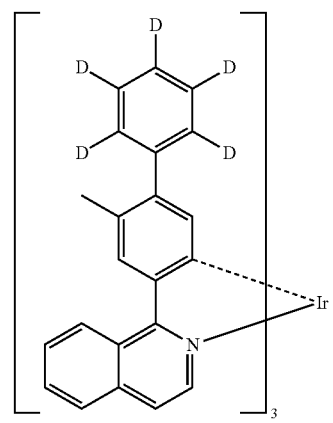
PD22 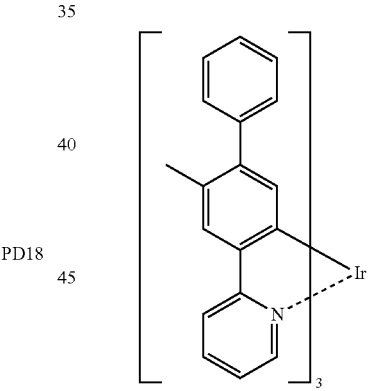
PD23 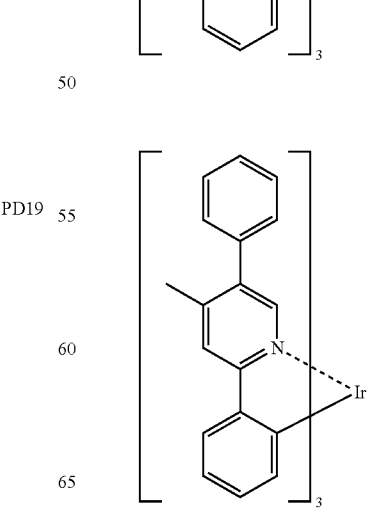

-continued

PD24
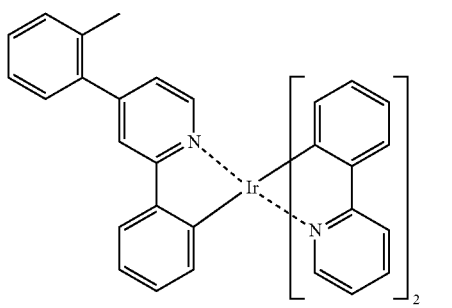

PD25
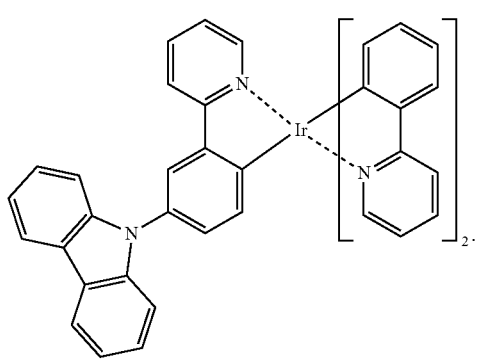

FD1
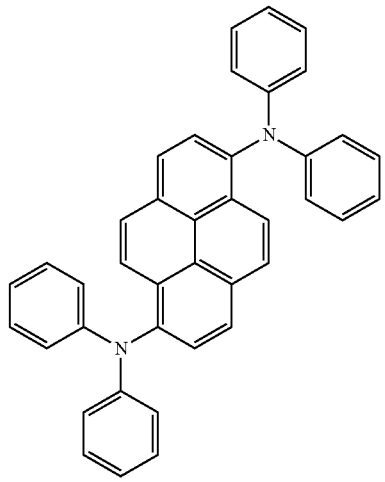

FD2
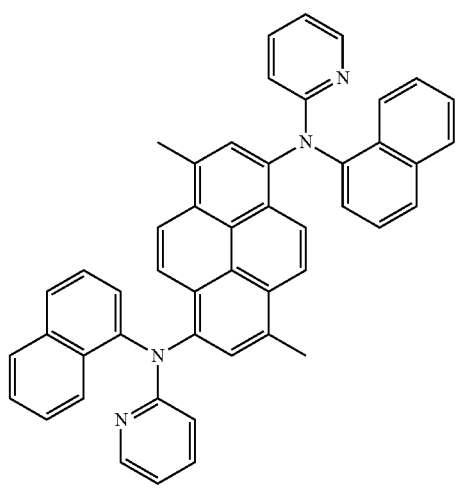

FD3
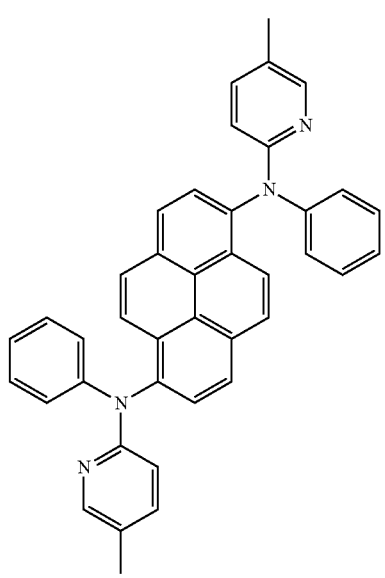

[Fluorescent Dopant]

The fluorescent dopant may include an amine group-containing compound, a styryl group-containing compound, or any combination thereof.

In an embodiment, the fluorescent dopant may include a compound represented by Formula 501:

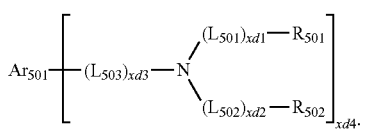

[Formula 501]

In Formula 501, $Ar_{501}$, $L_{501}$ to $L_{503}$, $R_{501}$, and $R_{502}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, xd1 to xd3 may each independently be 0, 1, 2, or 3, and xd4 may be 1, 2, 3, 4, 5, or 6.

In an embodiment, $Ar_{501}$ in Formula 501 may include a condensed cyclic group (for example, an anthracene group, a chrysene group, or a pyrene group) in which three or more monocyclic groups are condensed with each other.

In an embodiment, xd4 in Formula 501 may be 2.

In an embodiment, the fluorescent dopant may include one of following Compounds FD1 to FD36, DPVBi, DPAVBi, or any combination thereof:

FD4
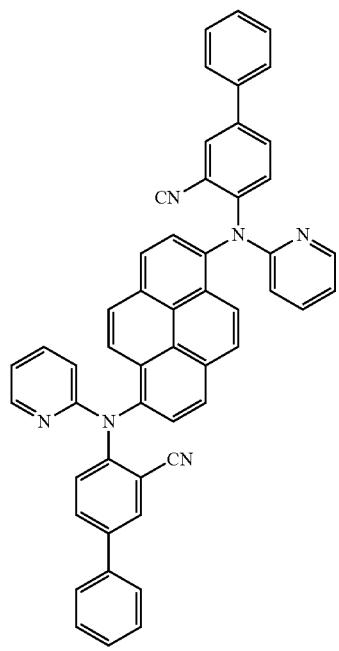
FD5
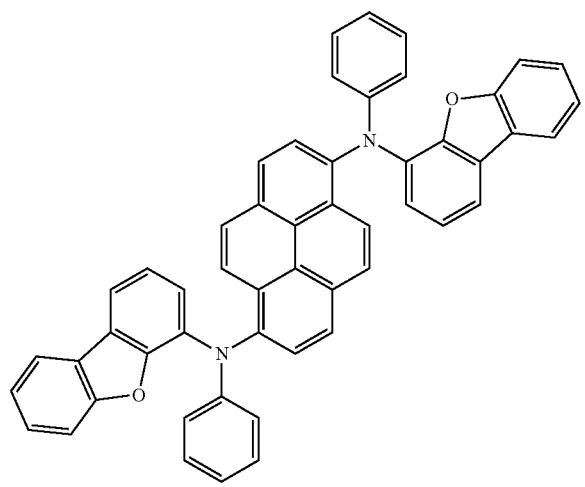
FD6
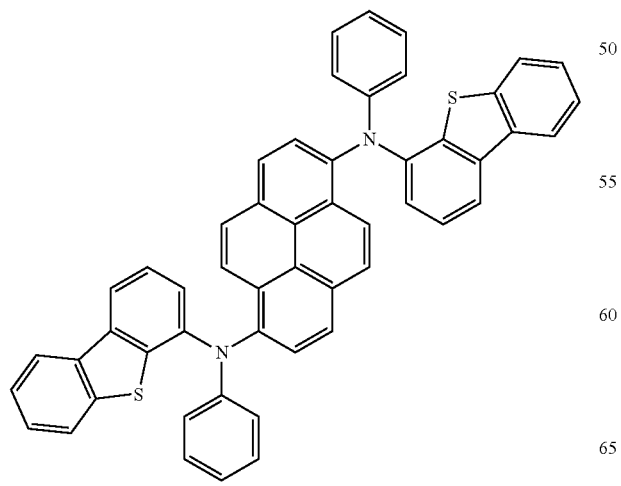
FD7
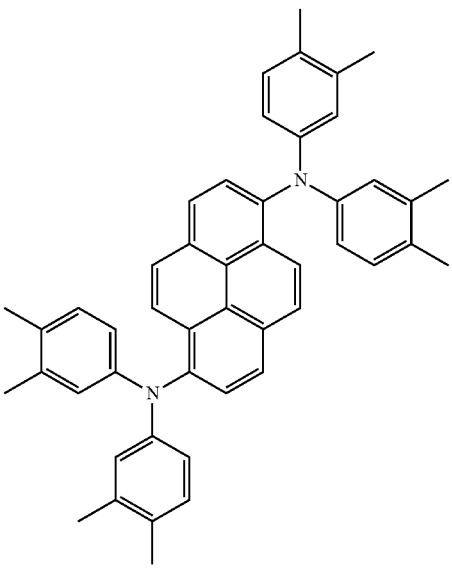
FD8
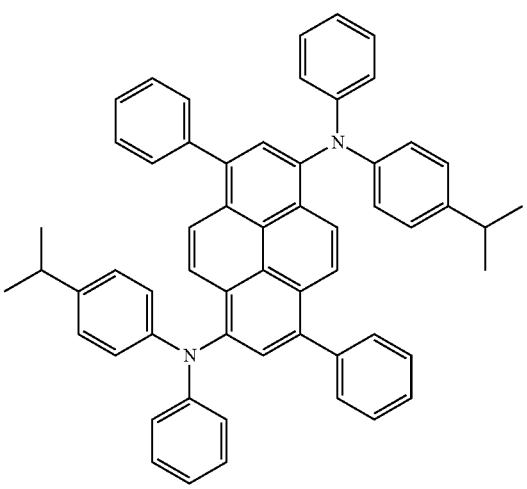
FD9

FD10 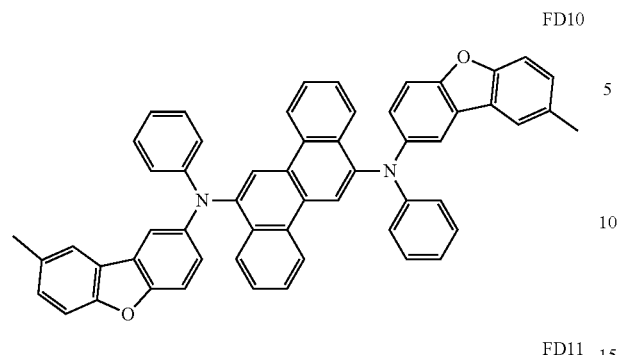
FD11 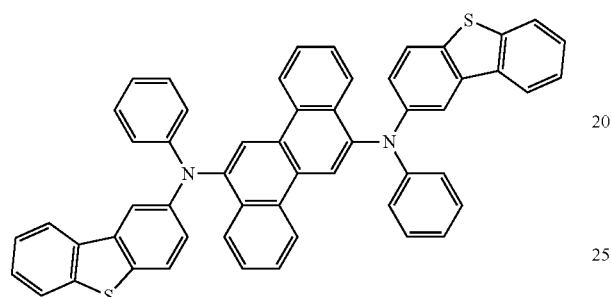
FD12 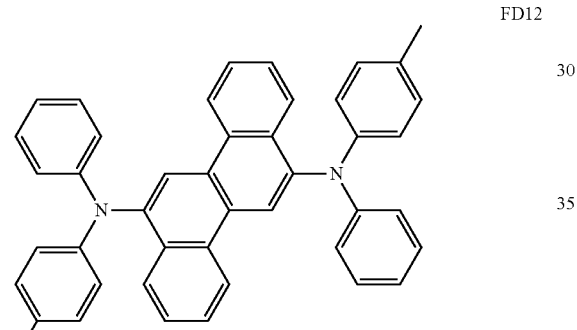
FD13 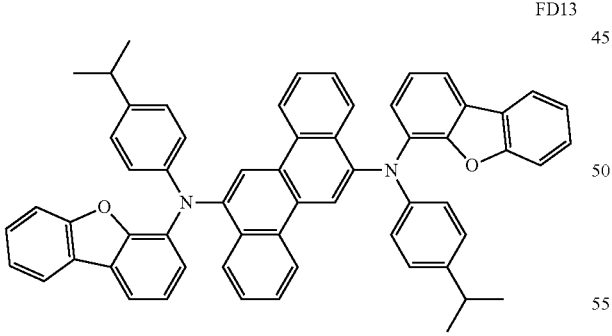
FD14 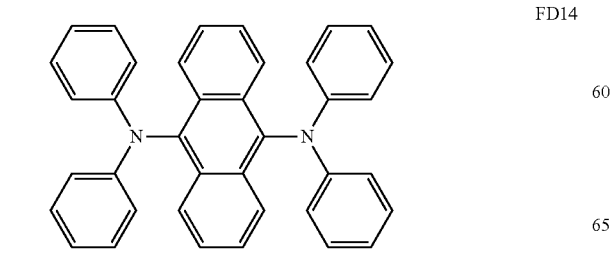
FD15 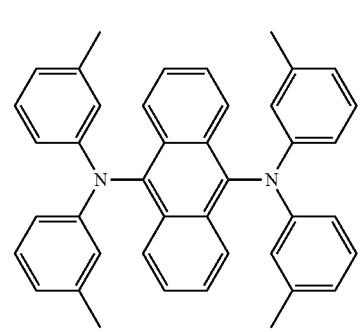
FD16 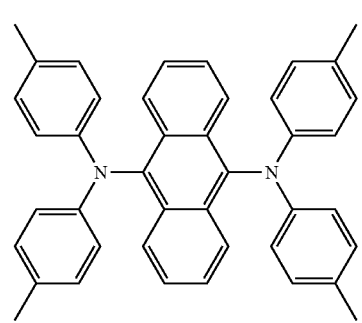
FD17 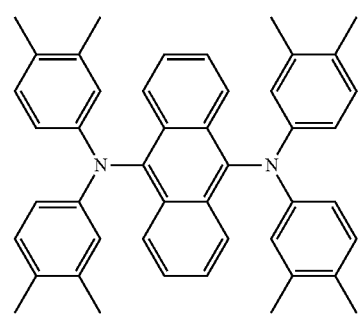
FD18 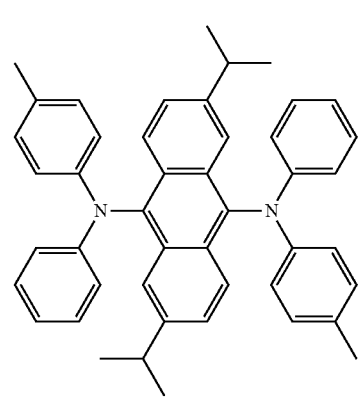

FD19
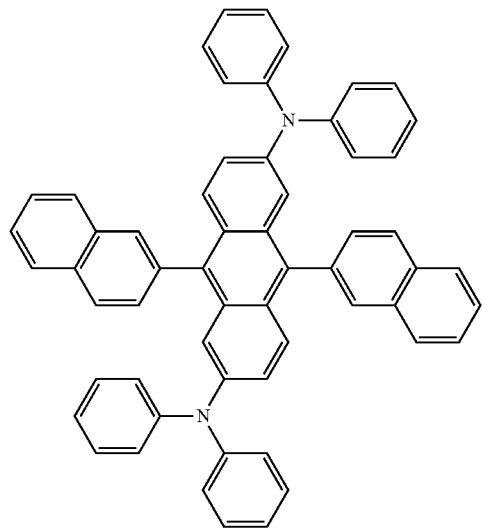
FD20
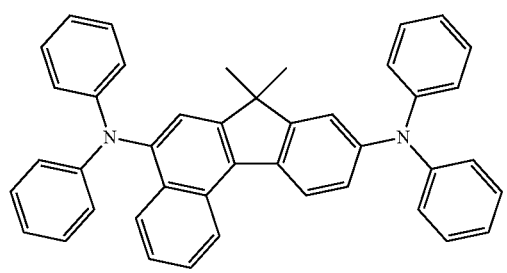
FD21
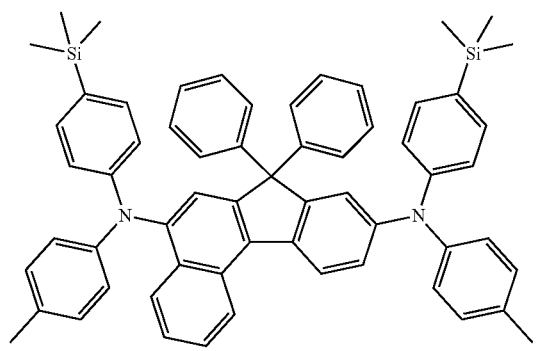
FD22
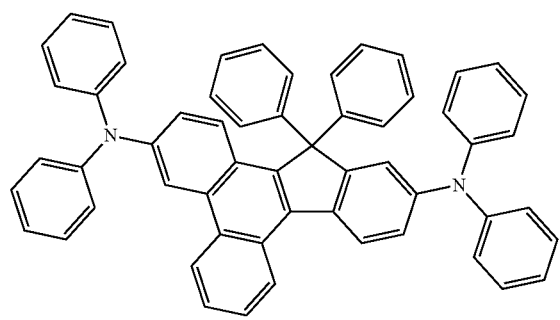
FD23
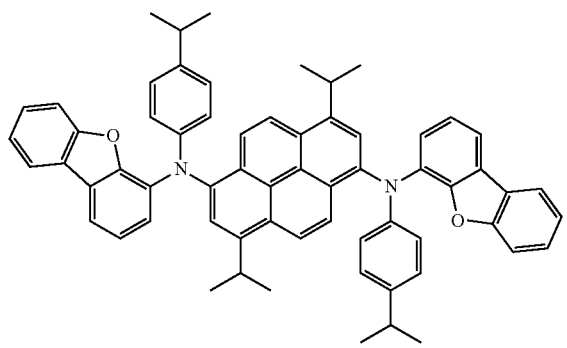
FD24
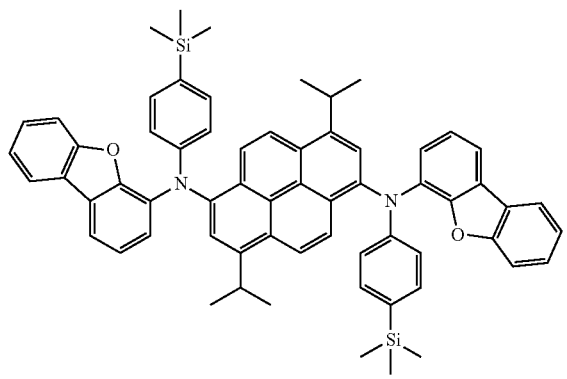
FD25
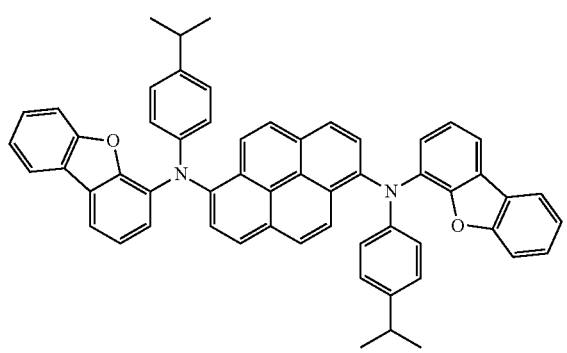
FD26
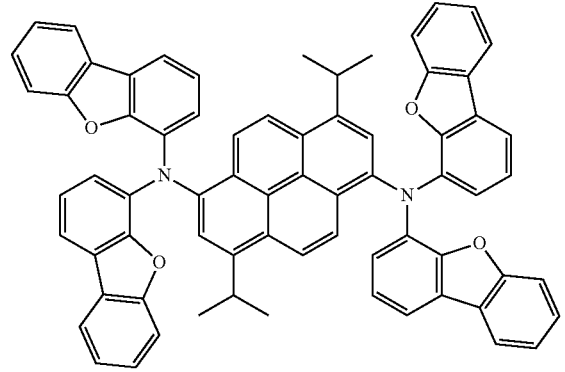

FD27
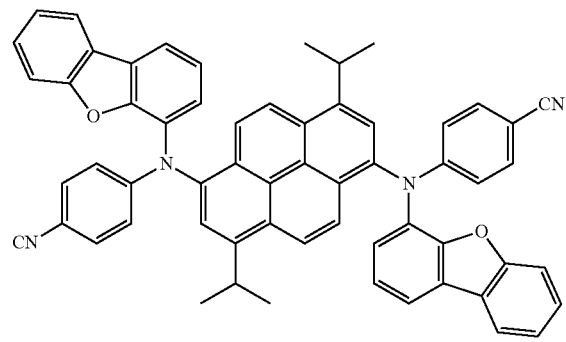
FD31
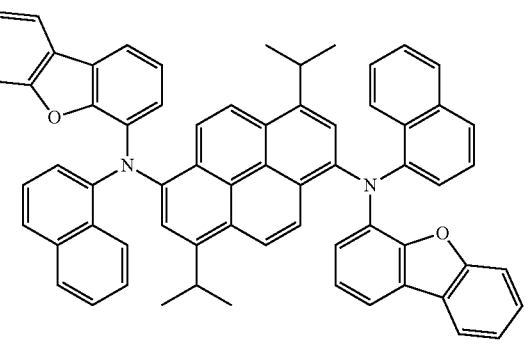
FD28
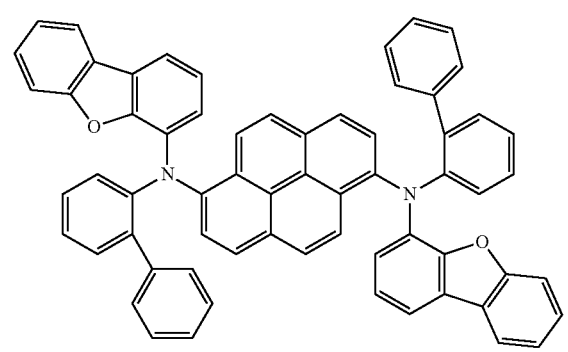
FD32
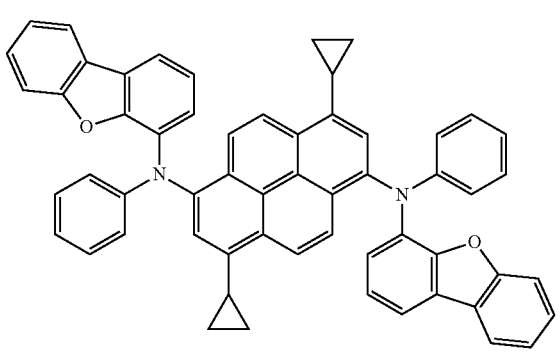
FD29
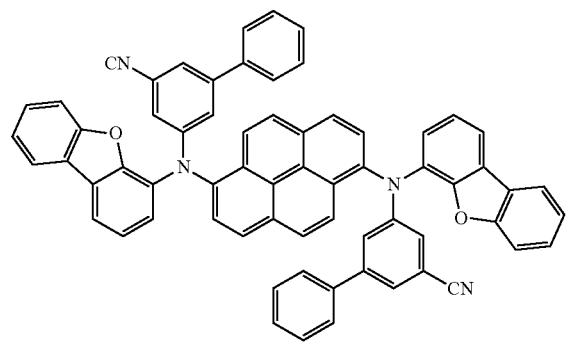
FD33
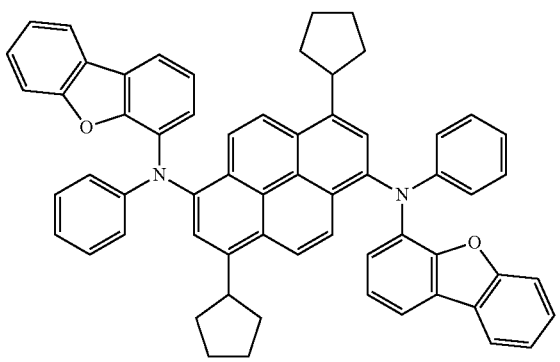
FD30
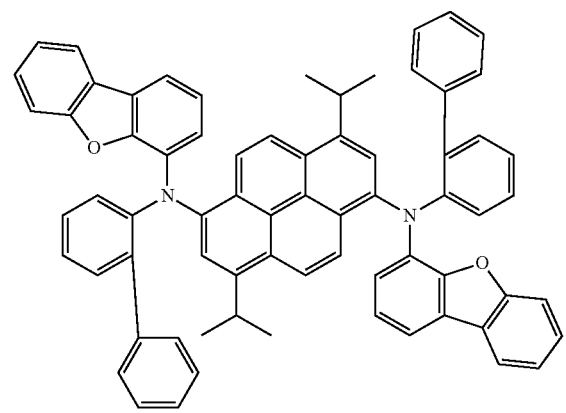
FD34
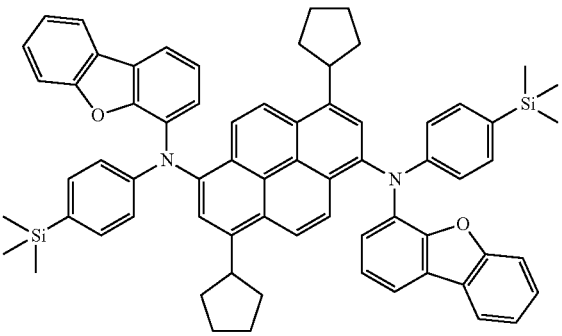

-continued

FD35

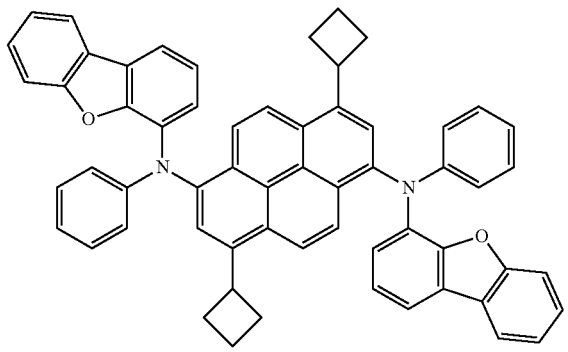

FD36

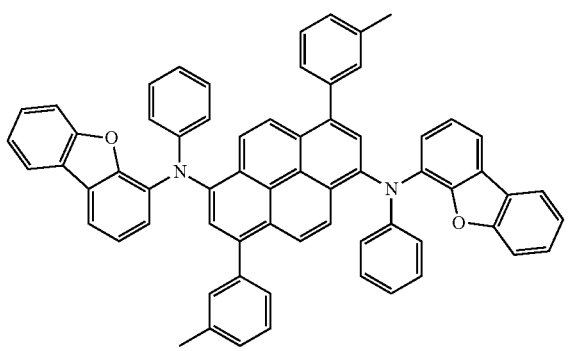

DPVBi

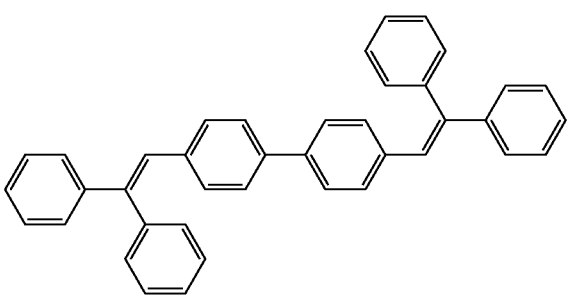

DPAVBi

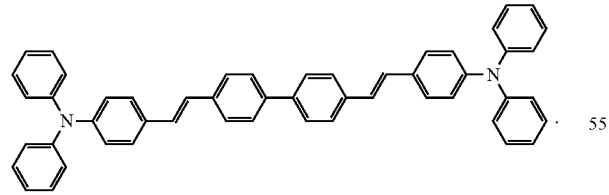

[Delayed Fluorescence Material]

The emission layer may include a delayed fluorescence material.

The delayed fluorescence material used herein may be selected from any compound that is capable of emitting delayed fluorescent light based on a delayed fluorescent emission mechanism.

The delayed fluorescence material included in the emission layer may act as a host or a dopant depending on the type of other materials included in the emission layer.

In an embodiment, the difference between the triplet energy level (eV) of the delayed fluorescence material and the singlet energy level (eV) of the delayed fluorescence material may be in a range of about 0 eV to about 0.5 eV. When the difference between the triplet energy level (eV) of the delayed fluorescence material and the singlet energy level (eV) of the delayed fluorescence material satisfies the above-described range, up-conversion from the triplet state to the singlet state of the delayed fluorescence materials may effectively occur, and thus, the light emission efficiency of the light-emitting device 10 may be improved.

In an embodiment, the delayed fluorescence material may include i) a material that includes at least one electron donor (for example, a π electron-rich $C_3$-$C_{60}$ cyclic group, such as a carbazole group) and at least one electron acceptor (for example, a sulfoxide group, a cyano group, or a π-electron-deficient nitrogen-containing $C_1$-$C_{60}$ cyclic group), ii) a material including a $C_8$-$C_{60}$ polycyclic group in which two or more cyclic groups share boron (B) and are condensed with each other.

The delayed fluorescence material may include at least one of Compounds DF1 to DF9:

DF1(DMAC-DPS)

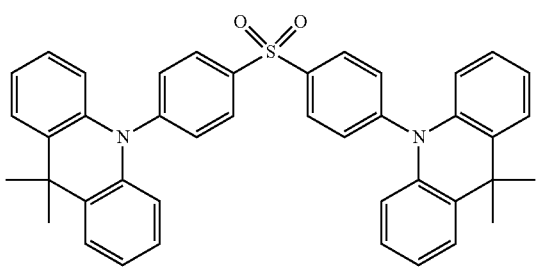

DF2(ACRFLCN)

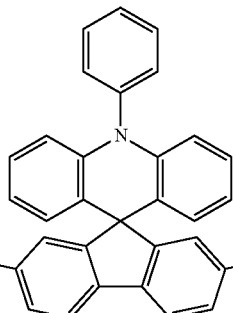
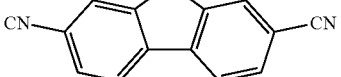

DF3(ACRSA)

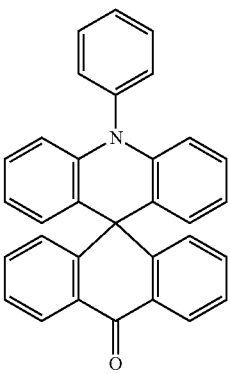

-continued

DF4(CC2TA)

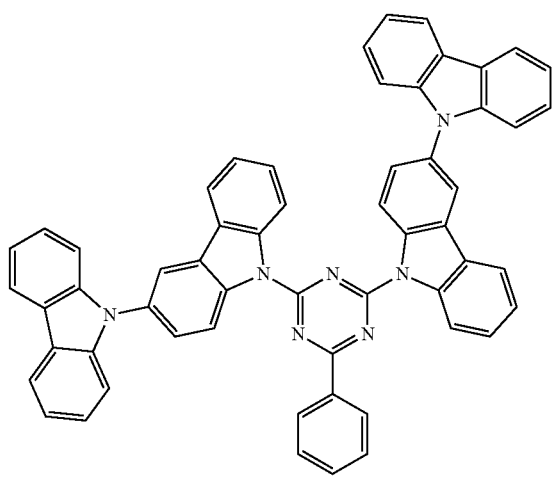

DF5(PIC-TRZ)

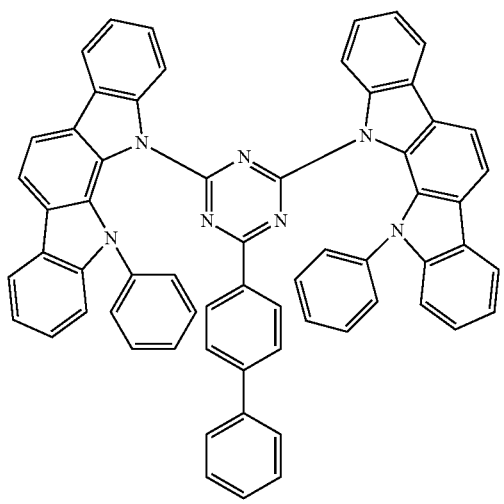

DF6(PIC-TRZ2)

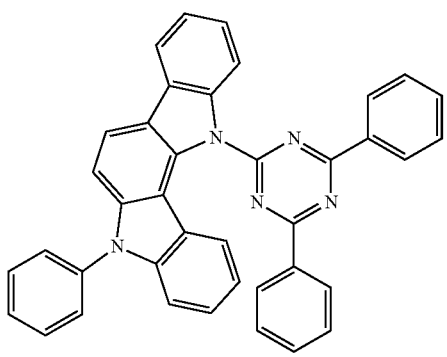

-continued

DF7(PXZ-TRZ)

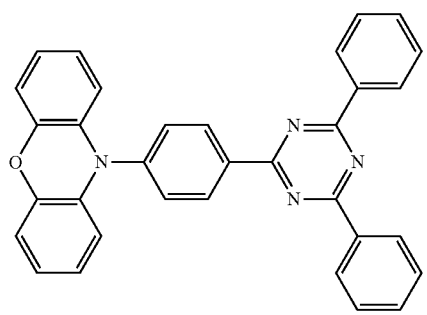

DF8(DABNA-1)

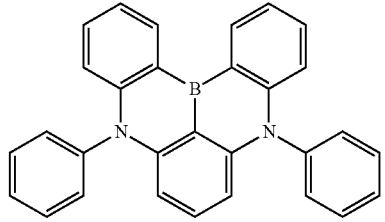

DF9(DABNA-2)

[Quantum Dot]

The emission layer may include a quantum dot.

The quantum dot used herein refers to a crystal of a semiconductor compound, and may include any material that is capable of emitting light of various emission wavelengths depending on a size of the crystal.

A diameter of the quantum dot may be, for example, in a range of about 1 nm to about 10 nm.

The quantum dot may be synthesized by a wet chemical process, a metal organic chemical vapor deposition process, a molecular beam epitaxy process, or a similar process.

The wet chemical process refers to a method in which an organic solvent and a precursor material are mixed, and a quantum dot particle crystal is grown. When the crystal grows, the organic solvent acts as a dispersant naturally coordinated on the surface of the quantum dot crystal and controls the growth of the crystal. Accordingly, by using a process that is easily performed at low costs compared to a vapor deposition process, such as a metal organic chemical vapor deposition (MOCVD) process and a molecular beam epitaxy (MBE) process, the growth of quantum dot particles may be controlled.

The quantum dot may include a Groups III-VI semiconductor compound, a Groups II-VI semiconductor compound, a Groups III-V semiconductor compound, a Group I-III-VI semiconductor compound, a Groups IV-VI semiconductor compound, a Group IV element or compound, or any combination thereof.

Examples of the Groups II-VI semiconductor compound may include: a binary compound, such as CdSe, CdTe, ZnS, ZnSe, ZnTe, ZnO, HgS, HgSe, HgTe, MgSe, or MgS; a ternary compound, such as CdSeS, CdSeTe, CdSTe, ZnSeS, ZnSeTe, ZnSTe, HgSeS, HgSeTe, HgSTe, CdZnS, CdZnSe, CdZnTe, CdHgS, CdHgSe, CdHgTe, HgZnS, HgZnSe, HgZnTe, MgZnSe, or MgZnS; a quaternary compound, such as CdZnSeS, CdZnSeTe, CdZnSTe, CdHgSeS, CdHgSeTe, CdHgSTe, HgZnSeS, HgZnSeTe, or HgZnSTe; or any combination thereof.

Examples of the Groups III-V semiconductor compound may include: a binary compound, such as GaN, GaP, GaAs, GaSb, AlN, AlP, AlAs, AlSb, InN, InP, InAs, or InSb; a ternary compound, such as GaNP, GaNAs, GaNSb, GaPAs, GaPSb, AlNP, AlNAs, AlNSb, AlPAs, AlPSb, InGaP, InNP, InAlP, InNAs, InNSb, InPAs, or InPSb; a quaternary compound, such as GaAlNP, GaAlNAs, GaAlNSb, GaAlPAs, GaAlPSb, GaInNP, GaInNAs, GaInNSb, GaInPAs, GaInPSb, InAlNP, InAlNAs, InAlNSb, InAlPAs, or InAlPSb; or any combination thereof. In an embodiment, the Groups III-V semiconductor compound may further include a Group II element. Examples of the Groups III-V semiconductor compound further including a Group II element may include InZnP, InGaZnP, or InAlZnP.

Examples of the Groups III-VI semiconductor compound may include: a binary compound, such as GaS, GaSe, $Ga_2Se_3$, GaTe, InS, $In_2S_3$, InSe, $In_2Se_3$, or InTe; a ternary compound, such as $InGaS_3$ or $InGaSe_3$; or any combination thereof.

Examples of the Groups I-III-VI semiconductor compound may include: a ternary compound such as AgInS, $AgInS_2$, CuInS, $CuInS_2$, $CuGaO_2$, $AgGaO_2$, or $AgAlO_2$; or any combination thereof.

Examples of the Group IV-VI semiconductor compound may include: a binary compound, such as SnS, SnSe, SnTe, PbS, PbSe, or PbTe; a ternary compound, such as SnSeS, SnSeTe, SnSTe, PbSeS, PbSeTe, PbSTe, SnPbS, SnPbSe, or SnPbTe; a quaternary compound, such as SnPbSSe, SnPbSeTe, or SnPbSTe; or any combination thereof.

The Group IV element or compound may include a single element, such as Si or Ge; a binary compound, such as SiC or SiGe; or any combination thereof.

Each element included in the multi-element compound such as the binary compound, the ternary compound, and the quaternary compound may be present in a particle at a uniform concentration or a non-uniform concentration.

The quantum dot may have a single structure having a uniform concentration of each element included in the corresponding quantum dot or a dual structure of a core-shell. In an embodiment, a material included in the core may be different from a material included in the shell.

The shell of the quantum dot may function as a protective layer for maintaining semiconductor characteristics by preventing chemical degeneration of the core and/or may function as a charging layer for imparting electrophoretic characteristics to the quantum dot. The shell may be a single layer or a multilayer. An interface between the core and the shell may have a concentration gradient in which the concentration of elements existing in the shell decreases toward the center.

Examples of the shell of the quantum dot are an oxide of a metal or a non-metal, a semiconductor compound, or any combination thereof. Examples of the oxide of metal or non-metal may include a binary compound, such as $SiO_2$, $Al_2O_3$, $TiO_2$, ZnO, MnO, $Mn_2O_3$, $Mn_3O_4$, CuO, FeO, $Fe_2O_3$, $Fe_3O_4$, CoO, $Co_3O_4$, or NiO; a ternary compound, such as $MgAl_2O_4$, $CoFe_2O_4$, $NiFe_2O_4$, or $CoMn_2O_4$; or any combination thereof. Examples of the semiconductor compound are, as described herein, a Groups III-VI semiconductor compound, a Groups II-VI semiconductor compound, a Groups III-V semiconductor compound, a Groups I-III-VI semiconductor compound, a Groups IV-VI semiconductor compound, or any combination thereof. In an embodiment, the semiconductor compound may include CdS, CdSe, CdTe, ZnS, ZnSe, ZnTe, ZnSeS, ZnTeS, GaAs, GaP, GaSb, HgS, HgSe, HgTe, InAs, InP, InGaP, InSb, AlAs, AlP, AlSb, or any combination thereof.

A full width at half maximum (FWHM) of an emission wavelength spectrum of the quantum dot may be equal to or less than about 45 nm. For example, the FWHM of an emission wavelength spectrum of the quantum dot may be equal to or less than about 40 nm. For example, the FWHM of an emission wavelength spectrum of the quantum dot may be equal to or less than about 30 nm. When the FWHM of the emission wavelength spectrum of the quantum dot is within this range, color purity or color reproduction may be improved. Light emitted through such a quantum dot may be irradiated omnidirectionally. Accordingly, a wide viewing angle may be increased.

The quantum dot may be a spherical, a pyramidal, a multi-arm, or a cubic nanoparticle, a nanotube, a nanowire, a nanofiber, or a nanoplate particle.

By adjusting a size of the quantum dot, the energy band gap may also be adjusted, and thus the quantum dot emission layer may obtain light of various wavelengths. Therefore, by using quantum dots of different sizes, a light-emitting device that emits light of various wavelengths may be implemented. In an embodiment, the size of the quantum dot may be selected to emit red, green and/or blue light. The size of the quantum dot may be adjusted such that light of various colors are combined to emit white light.

[Electron Transport Region in Interlayer 130]

The electron transport region may have: i) a single-layered structure consisting of a single layer consisting of a single material, ii) a single-layered structure consisting of a single layer including different materials, or iii) a multi-layered structure including layers including different materials.

The electron transport region may include a buffer layer, a hole blocking layer, an electron control layer, an electron transport layer, an electron injection layer, or any combination thereof.

For example, the electron transport region may have an electron transport layer/electron injection layer structure, a hole blocking layer/electron transport layer/electron injection layer structure, an electron control layer/electron transport layer/electron injection layer structure, or a buffer layer/electron transport layer/electron injection layer structure, wherein, for each structure, constituting layers are sequentially stacked from an emission layer.

The electron transport region (for example, the buffer layer, the hole blocking layer, the electron control layer, or the electron transport layer in the electron transport region) may include a metal-free compound including at least one π-electron-deficient nitrogen-containing $C_1$-$C_{60}$ cyclic group.

In an embodiment, the electron transport region may include a compound represented by Formula 601.

$$[Ar_{601}]_{xe11}-[(L_{601})_{xe1}-R_{601}]_{xe21} \qquad \text{[Formula 601]}$$

In Formula 601, $Ar_{601}$ and $L_{601}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, xe11 may be 1, 2, or 3, xe1 may be 0, 1, 2, 3, 4, or 5, $R_{601}$ may be a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, —Si($Q_{601}$)($Q_{602}$)($Q_{603}$), —C(=O)($Q_{601}$), —S(=O)$_2$($Q_{601}$), or —P(=O)($Q_{601}$)($Q_{602}$), $Q_{601}$ to $Q_{603}$ are the same as described in connection with $Q_1$ in the specification, xe21 may be 1, 2, 3, 4, or 5, and at least one of $Ar_{601}$, $L_{601}$, and $R_{601}$ may each independently be a π-electron-deficient nitrogen-containing $C_1$-$C_{60}$ cyclic group unsubstituted or substituted with at least one $R_{10a}$.

In an embodiment, when xe11 in Formula 601 is 2 or more, two or more of $Ar_{601}$(s) may be linked to each other via a single bond.

In an embodiment, $Ar_{601}$ in Formula 601 may be a substituted or unsubstituted anthracene group.

In an embodiment, the electron transport region may include a compound represented by Formula 601-1:

[Formula 601-1]

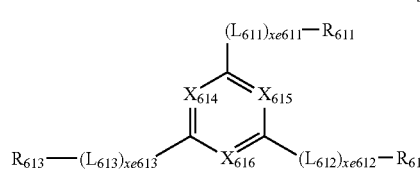

In Formula 601-1, $X_{614}$ may be N or C($R_{614}$), $X_{615}$ may be N or C($R_{615}$), $X_{616}$ may be N or C($R_{616}$), at least one of $X_{614}$ to $X_{616}$ may be N, $L_{611}$ to $L_{613}$ are the same as described in connection with $L_{601}$, xe611 to xe613 are the same as described in connection with xe1, $R_{611}$ to $R_{613}$ are the same as described in connection with $R_{601}$, and $R_{614}$ to $R_{616}$ may each independently be hydrogen, deuterium, —F, —Cl, —Br, —I, a hydroxyl group, a cyano group, a nitro group, a $C_1$-$C_{20}$ alkyl group, a $C_1$-$C_{20}$ alkoxy group, a $C_3$-$C_{60}$ carbocyclic group unsubstituted or substituted with at least one $R_{10a}$, or a $C_1$-$C_{60}$ heterocyclic group unsubstituted or substituted with at least one $R_{10a}$.

In an embodiment, xe1 and xe611 to xe613 in Formulae 601 and 601-1 may each independently be 0, 1, or 2.

The electron transport region may include one of Compounds ET1 to ET45, 2,9-dimethyl-4,7-diphenyl-1,10-phenanthroline (BCP), 4,7-diphenyl-1,10-phenanthroline (Bphen), Alq3, BAlq, TAZ, NTAZ, or any combination thereof:

ET1
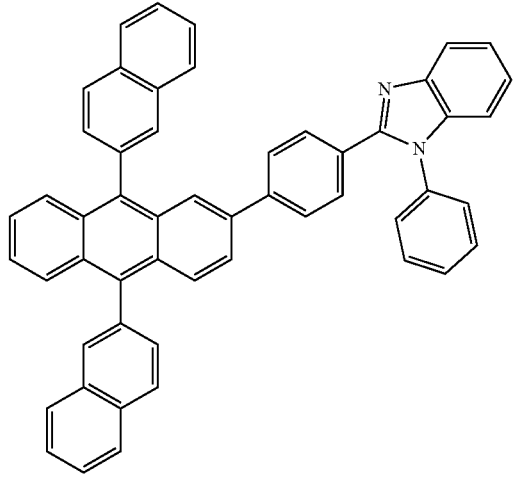

ET2
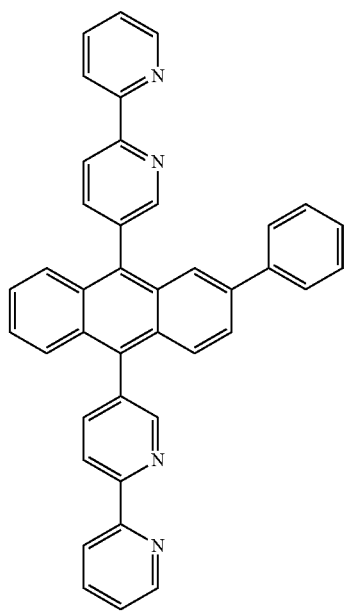

ET3
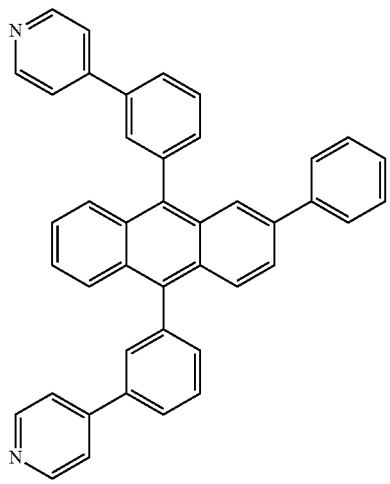

ET4
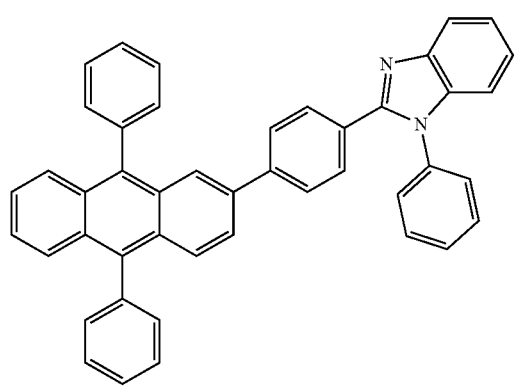
ET5
ET6
ET7
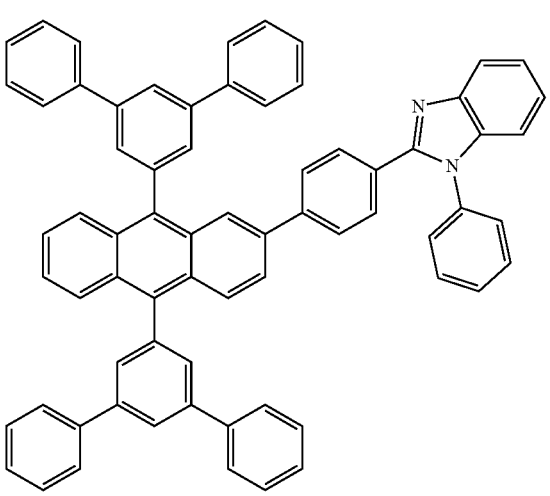
ET8
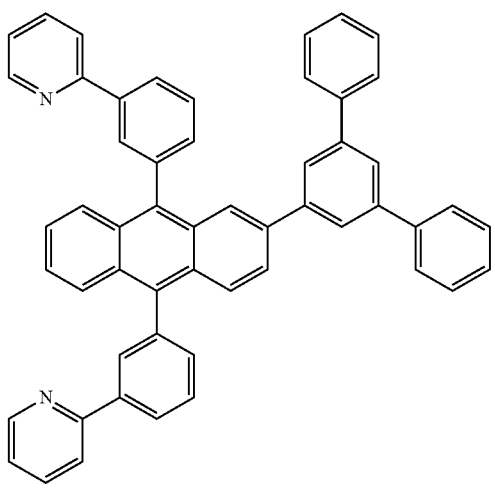
ET9
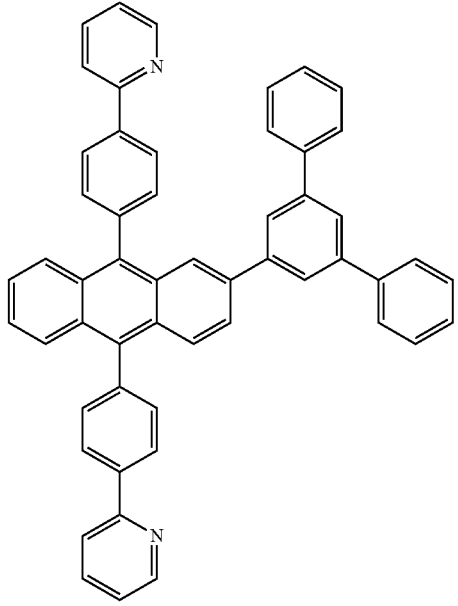

ET10
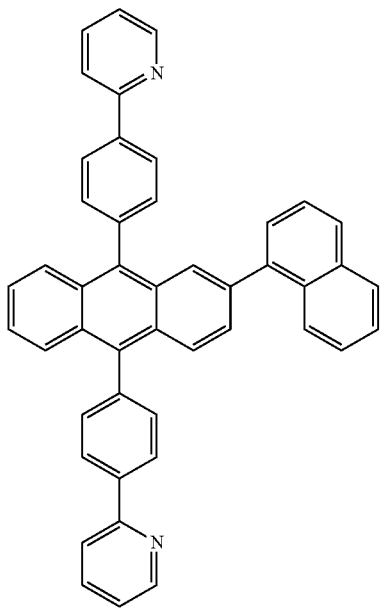
ET11
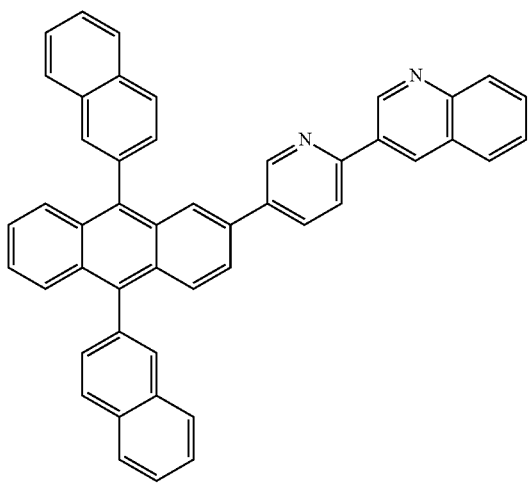
ET12
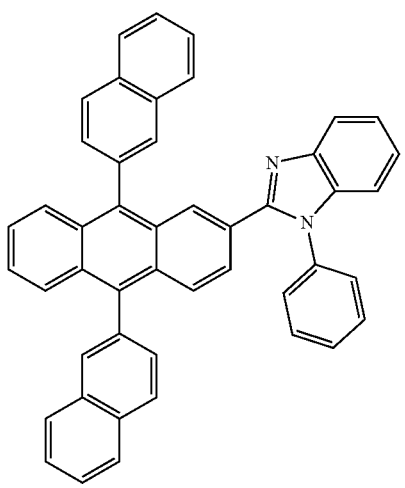
ET13
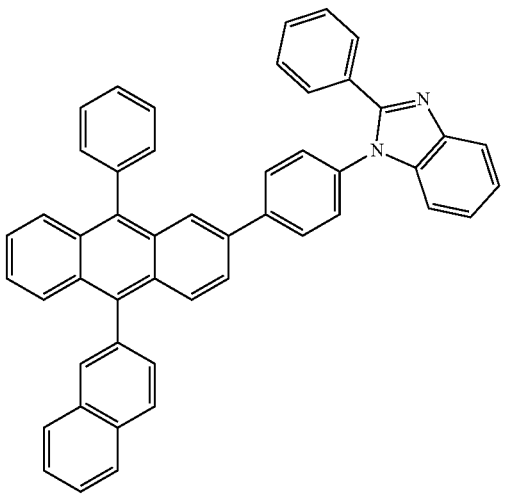
ET14
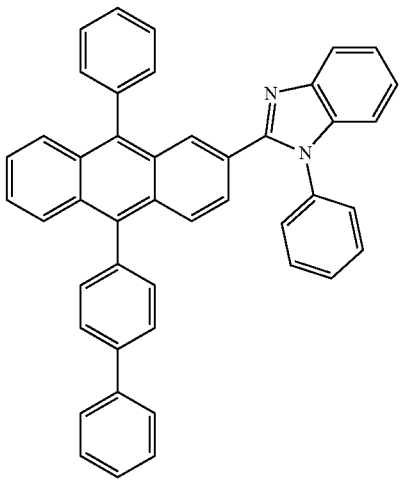
ET15
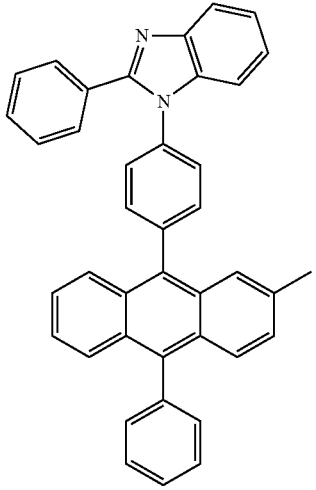

ET16
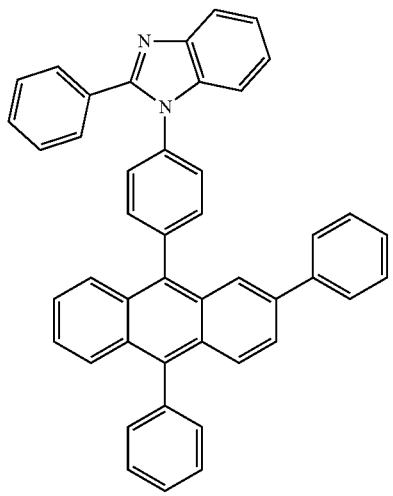
ET17
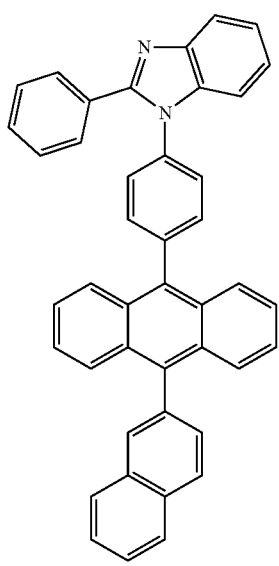
ET18
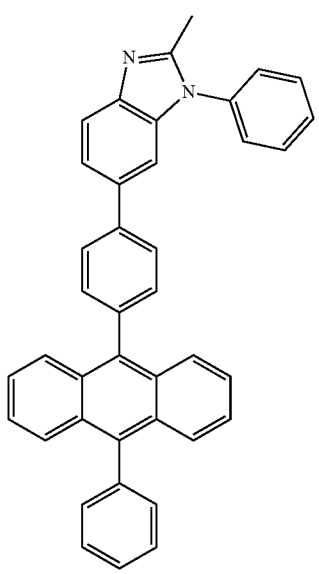
ET19
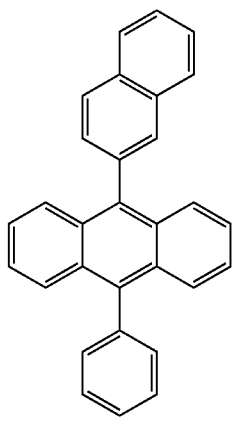
ET20
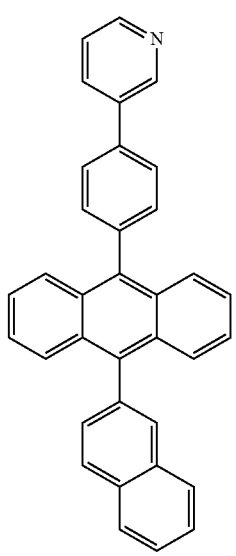
ET21
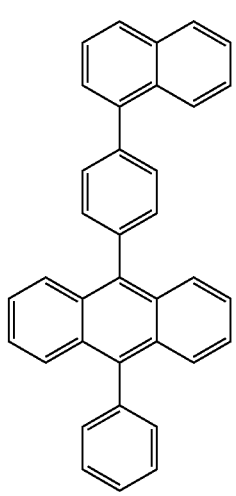

ET22
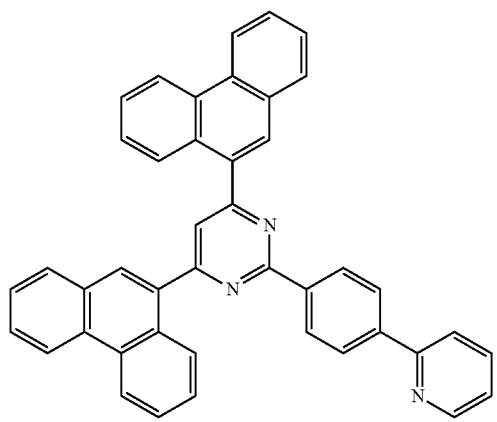
ET23
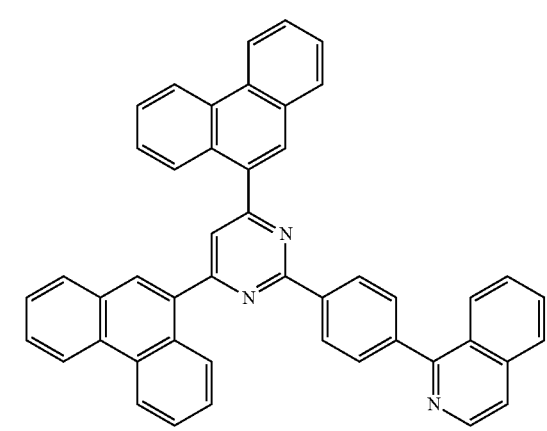
ET24
ET25
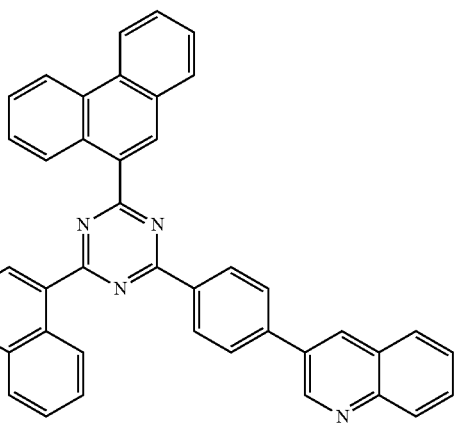
ET26
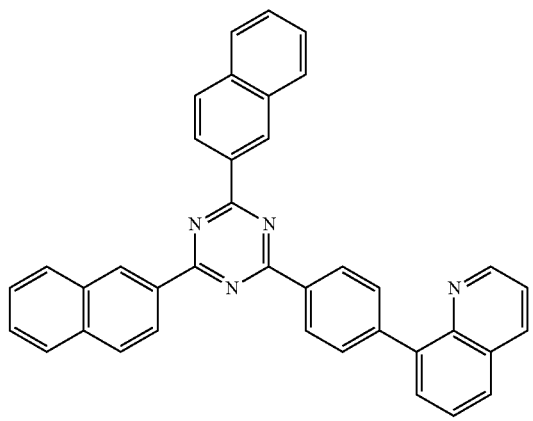
ET27

ET28
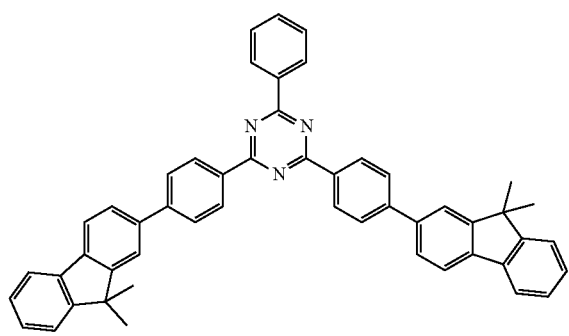
ET29
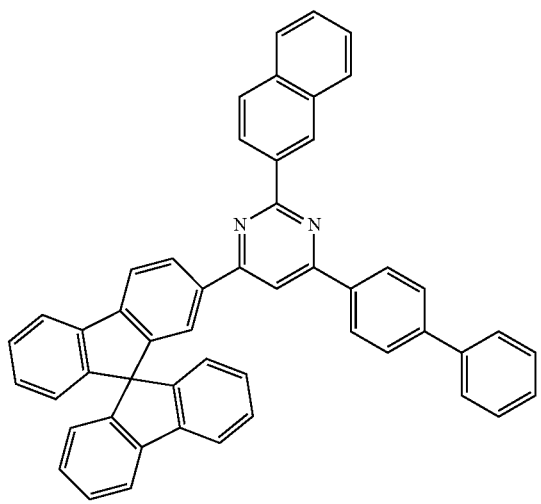
ET30
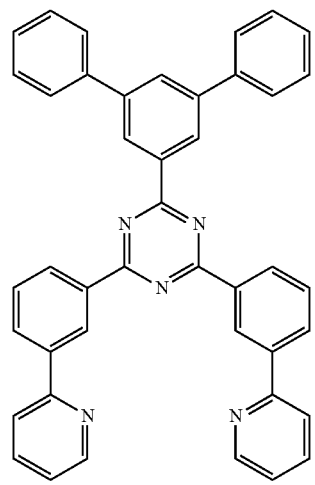
ET31
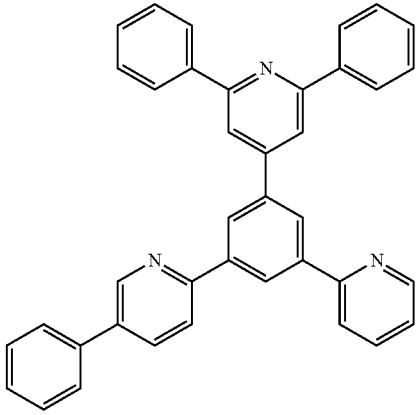
ET32
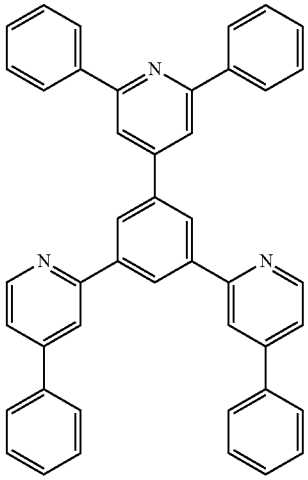
ET33
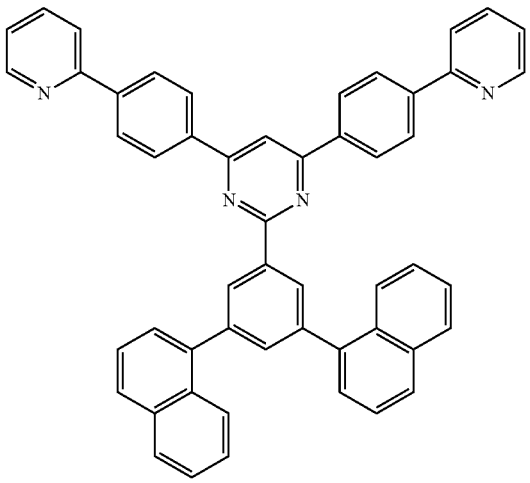

-continued
ET34
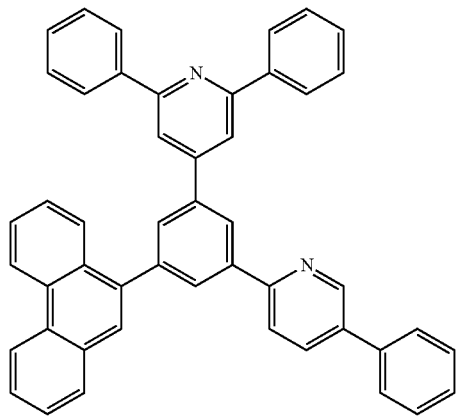
ET35
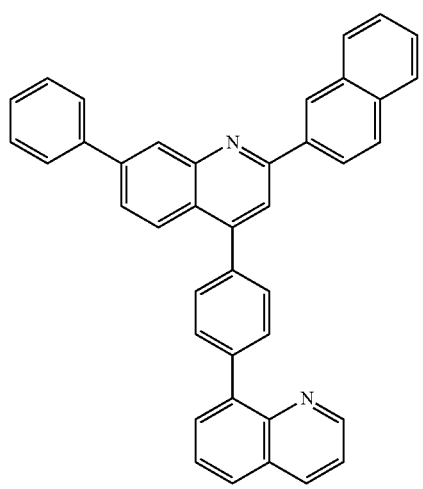
ET36
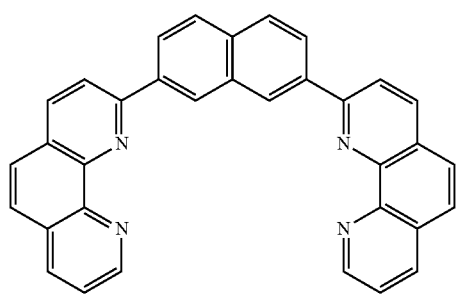
ET37
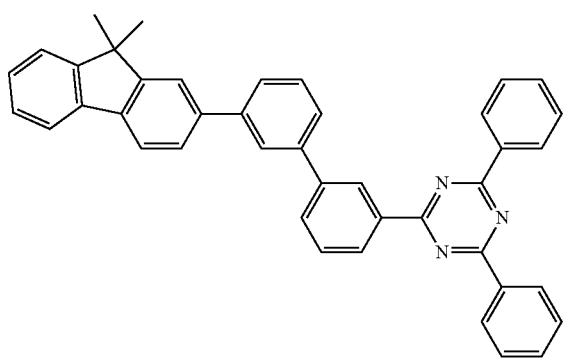
-continued
ET38
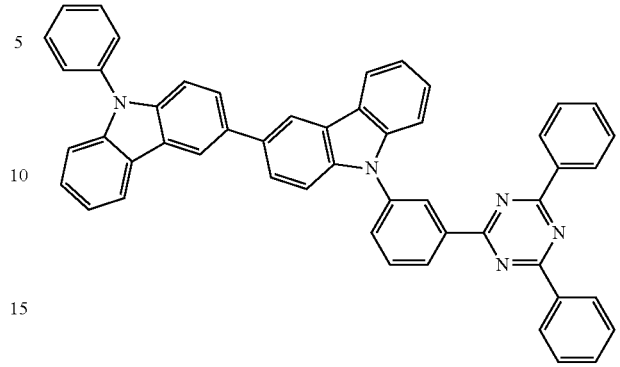
ET39
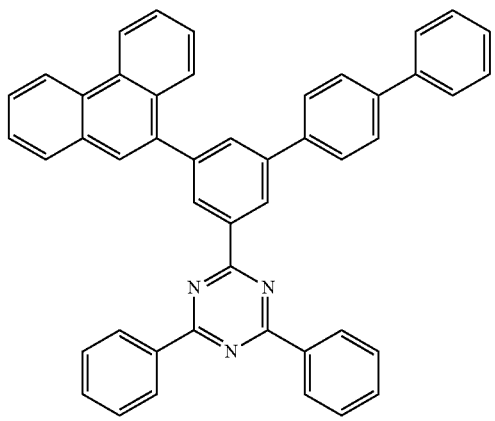
ET40
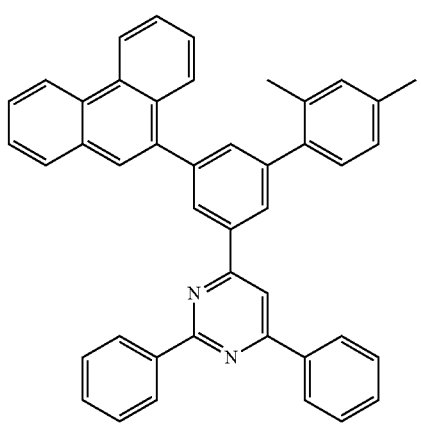

ET41
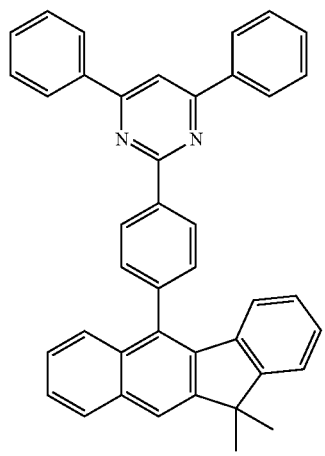
ET42
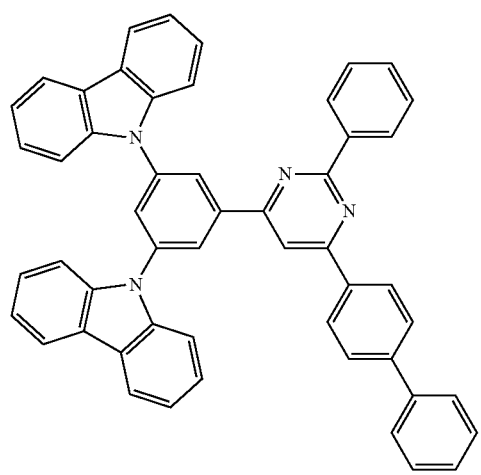
ET43
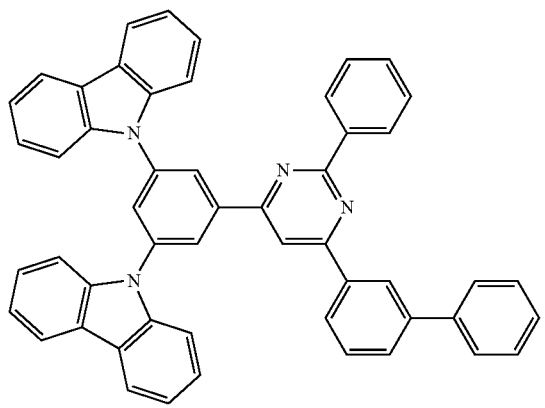
ET44
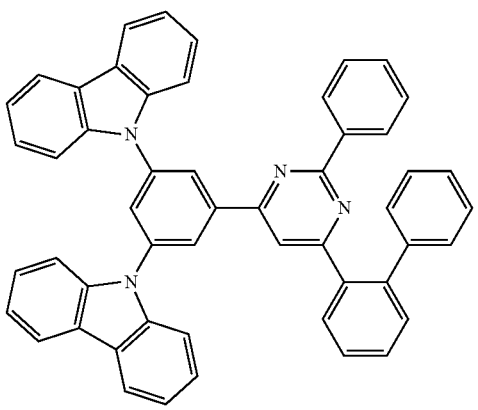
ET45
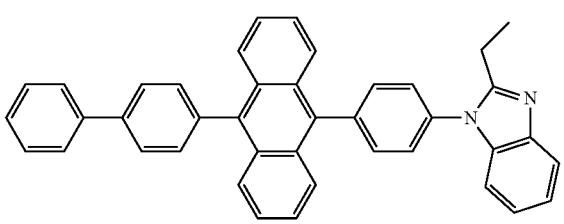
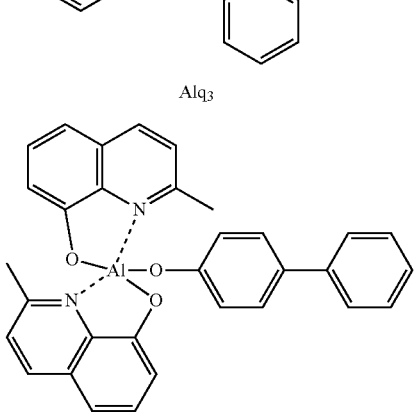
Alq3
BAlq
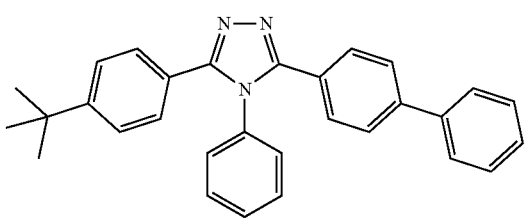
TAZ

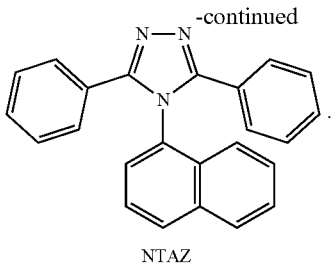

NTAZ

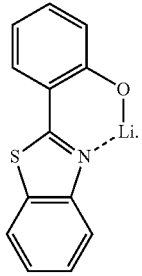

ET-D2

A thickness of the electron transport region may be in a range of about 100 Å to about 5,000 Å. For example, the thickness of the electron transport region may be in a range of about 100 Å to about 4,000 Å. When the electron transport region includes a buffer layer, a hole blocking layer, an electron control layer, an electron transport layer, or any combination thereof, a thickness of the buffer layer, the hole blocking layer, or the electron control layer may each independently be in a range of about 20 Å to about 1,000 Å, and the thickness of the electron transport layer may be in a range of about 100 Å to about 1,000 Å. For example, the thickness of the buffer layer, the hole blocking layer, or the electron control layer may each independently be in a range of about 30 Å to about 300 Å. For example, the thickness of the electron transport layer may be in a range of about 150 Å to about 500 Å. When the thickness of the buffer layer, the hole blocking layer, the electron control layer, the electron transport layer, and/or the electron transport region are within these ranges, satisfactory electron transporting characteristics may be obtained without a substantial increase in driving voltage.

The electron transport region (for example, the electron transport layer in the electron transport region) may further include, in addition to the materials described above, a metal-containing material.

The metal-containing material may include an alkali metal complex, an alkaline earth-metal complex, or any combination thereof. A metal ion of the alkali metal complex may be a Li ion, a Na ion, a K ion, a Rb ion, or a Cs ion, and a metal ion of the alkaline earth-metal complex may be a Be ion, a Mg ion, a Ca ion, a Sr ion, or a Ba ion. A ligand coordinated with the metal ion of the alkali metal complex or the alkaline earth-metal complex may be a hydroxy quinoline, a hydroxy isoquinoline, a hydroxy benzoquinoline, a hydroxy acridine, a hydroxy phenanthridine, a hydroxy phenyloxazole, a hydroxy phenylthiazole, a hydroxy phenyloxadiazole, a hydroxy phenylthiadiazole, a hydroxy phenylpyridine, a hydroxy phenylbenzimidazole, a hydroxy phenylbenzothiazole, a bipyridine, a phenanthroline, a cyclopentadiene, or any combination thereof.

In an embodiment, the metal-containing material may include a Li complex. The Li complex may include, for example, Compound ET-D1 (LiQ) or ET-D2:

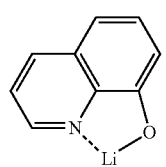

ET-D1

The electron transport region may include an electron injection layer that facilitates the injection of electrons from the second electrode 150. The electron injection layer may directly contact the second electrode 150.

The electron injection layer may have: i) a single-layered structure consisting of a single layer consisting of a single material, ii) a single-layered structure consisting of a single layer including different materials, or iii) a multi-layered structure including layers including different materials.

The electron injection layer may include an alkali metal, an alkaline earth metal, a rare earth metal, an alkali metal-containing compound, an alkaline earth metal-containing compound, a rare earth metal-containing compound, an alkali metal complex, an alkaline earth-metal complex, a rare earth metal complex, or any combination thereof.

The alkali metal may include Li, Na, K, Rb, Cs, or any combination thereof. The alkaline earth metal may include Mg, Ca, Sr, Ba, or any combination thereof. The rare earth metal may include Sc, Y, Ce, Tb, Yb, Gd, or any combination thereof.

The alkali metal-containing compound, the alkaline earth metal-containing compound, and the rare earth metal-containing compound may include oxides and halides (for example, fluorides, chlorides, bromides, or iodides) of the alkali metal, the alkaline earth metal, and the rare earth metal, telluride, or any combination thereof.

The alkali metal-containing compound may include alkali metal oxides, such as $Li_2O$, $Cs_2O$, or $K_2O$, alkali metal halides, such as LiF, NaF, CsF, KF, LiI, NaI, CsI, or KI, or any combination thereof. The alkaline earth metal-containing compound may include an alkaline earth metal compound, such as BaO, SrO, CaO, $Ba_xSr_{1-x}O$ (x is a real number that satisfies the condition of 0<x<1), or $Ba_xCa_{1-x}O$ (x is a real number that satisfies the condition of 0<x<1). The rare earth metal-containing compound may include $YbF_3$, $ScF_3$, $Sc_2O_3$, $Y_2O_3$, $Ce_2O_3$, $GdF_3$, $TbF_3$, $YbI_3$, $ScI_3$, $TbI_3$, or any combination thereof. In an embodiment, the rare earth metal-containing compound may include lanthanide metal telluride. Examples of the lanthanide metal telluride may include LaTe, CeTe, PrTe, NdTe, PmTe, SmTe, EuTe, GdTe, TbTe, DyTe, HoTe, ErTe, TmTe, YbTe, LuTe, $La_2Te_3$, $Ce_2Te_3$, $Pr_2Te_3$, $Nd_2Te_3$, $Pm_2Te_3$, $Sm_2Te_3$, $Eu_2Te_3$, $Gd_2Te_3$, $Tb_2Te_3$, $Dy_2Te_3$, $Ho_2Te_3$, $Er_2Te_3$, $Tm_2Te_3$, $Yb_2Te_3$, and $Lu_2Te_3$.

The alkali metal complex, the alkaline earth-metal complex, and the rare earth metal complex may include i) one of ions of the alkali metal, the alkaline earth metal, and the rare earth metal and ii) a ligand linked to the metal ion, for example, hydroxyquinoline, hydroxy isoquinoline, hydroxybenzoquinoline, hydroxyacridine, hydroxyphenanthridine, hydroxyphenyloxazole, hydroxyphenylthiazole, hydroxyphenyloxadiazole, hydroxyphenylthiadiazole, hydroxyphenylpyridine, hydroxyphenyl benzimidazole, hydroxyphenylbenzothiazole, bipyridine, phenanthroline, cyclopentadiene, or any combination thereof.

The electron injection layer may consist of an alkali metal, an alkaline earth metal, a rare earth metal, an alkali metal-containing compound, an alkaline earth metal-containing compound, a rare earth metal-containing compound, an alkali metal complex, an alkaline earth-metal complex, a rare earth metal complex, or any combination thereof, or may further include an organic material (for example, a compound represented by Formula 601).

In an embodiment, the electron injection layer may consist of i) an alkali metal-containing compound (for example, an alkali metal halide), or ii) a) an alkali metal-containing compound (for example, an alkali metal halide); and b) an alkali metal, an alkaline earth metal, a rare earth metal, or any combination thereof. In an embodiment, the electron injection layer may be a KI:Yb co-deposited layer or a RbI:Yb co-deposited layer.

When the electron injection layer further includes an organic material, an alkali metal, an alkaline earth metal, a rare earth metal, an alkali metal-containing compound, an alkaline earth metal-containing compound, a rare earth metal-containing compound, an alkali metal complex, an alkaline earth-metal complex, a rare earth metal complex, or any combination thereof may be homogeneously or non-homogeneously dispersed in a matrix including the organic material.

A thickness of the electron injection layer may be in a range of about 1 Å to about 100 Å. For example, the thickness of the electron injection layer may be in a range of about 3 Å to about 90 Å. When the thickness of the electron injection layer is within the range described above, the electron injection layer may have satisfactory electron injection characteristics without a substantial increase in driving voltage.

[Second Electrode 150]

The second electrode 150 may be located on the interlayer 130 having such a structure. The second electrode 150 may be a cathode, which is an electron injection electrode, and as the material for forming the second electrode 150, a metal, an alloy, an electrically conductive compound, or any combination thereof, each having a low work function, may be used.

The second electrode 150 may include lithium (Li), silver (Ag), magnesium (Mg), aluminum (Al), aluminum-lithium (Al—Li), calcium (Ca), magnesium-indium (Mg—In), magnesium-silver (Mg—Ag), ytterbium (Yb), silver-ytterbium (Ag—Yb), ITO, IZO, or any combination thereof. The second electrode 150 may be a transmissive electrode, a semi-transmissive electrode, or a reflective electrode.

The second electrode 150 may have a single-layered structure or a multi-layered structure including two or more layers.

[Capping Layer]

A first capping layer may be located outside the first electrode 110, and/or a second capping layer may be located outside the second electrode 150. The light-emitting device 10 may have a structure in which the first capping layer, the first electrode 110, the interlayer 130, and the second electrode 150 are sequentially stacked in this stated order, a structure in which the first electrode 110, the interlayer 130, the second electrode 150, and the second capping layer are sequentially stacked in this stated order, or a structure in which the first capping layer, the first electrode 110, the interlayer 130, the second electrode 150, and the second capping layer are sequentially stacked in this stated order.

Light generated in an emission layer of the interlayer 130 of the light-emitting device 10 may be emitted toward the outside through the first electrode 110, which is a semi-transmissive electrode or a transmissive electrode, and the first capping layer, and light generated in an emission layer of the interlayer 130 of the light-emitting device 10 may be emitted toward the outside through the second electrode 150, which is a semi-transmissive electrode or a transmissive electrode, and the second capping layer.

The first capping layer and the second capping layer may increase external light emission efficiency according to the principle of constructive interference. Accordingly, light emission efficiency of the light-emitting device 10 is increased, so that the light emission efficiency of the light-emitting device 10 may be improved.

The first capping layer and the second capping layer may each include a material having a refractive index of equal to or greater than about 1.6 (at 589 nm).

The first capping layer and the second capping layer may each independently be an organic capping layer including an organic material, an inorganic capping layer including an inorganic material, or a composite capping layer including an organic material and an inorganic material.

At least one of the first capping layer and the second capping layer may each independently include a carbocyclic compound, a heterocyclic compound, an amine group-containing compound, a porphyrine derivative, a phthalocyanine derivative, a naphthalocyanine derivative, an alkali metal complex, an alkaline earth-metal complex, or any combination thereof. The carbocyclic compound, the heterocyclic compound, and the amine group-containing compound may be optionally substituted with a substituent containing O, N, S, Se, Si, F, Cl, Br, I, or any combination thereof. In an embodiment, at least one of the first capping layer and the second capping layer may each independently include an amine group-containing compound.

In an embodiment, at least one of the first capping layer and second capping layer may each independently include a compound represented by Formula 201, a compound represented by Formula 202, or any combination thereof.

In an embodiment, at least one of the first capping layer and the second capping layer may each independently include one of Compounds HT28 to HT33, one of Compounds CP1 to CP6, β-NPB, or any combination thereof:

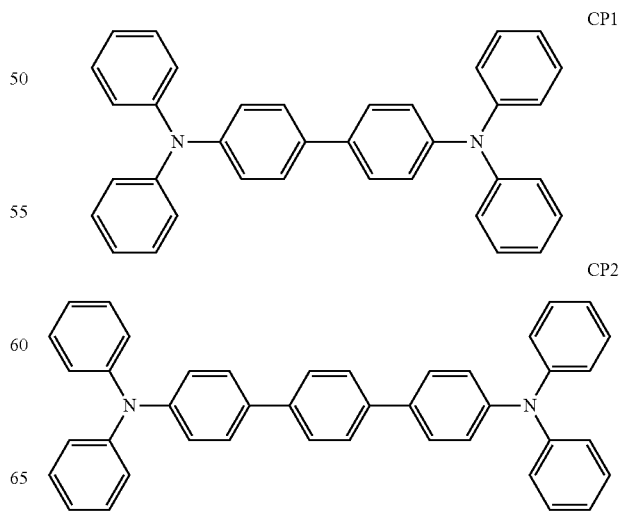

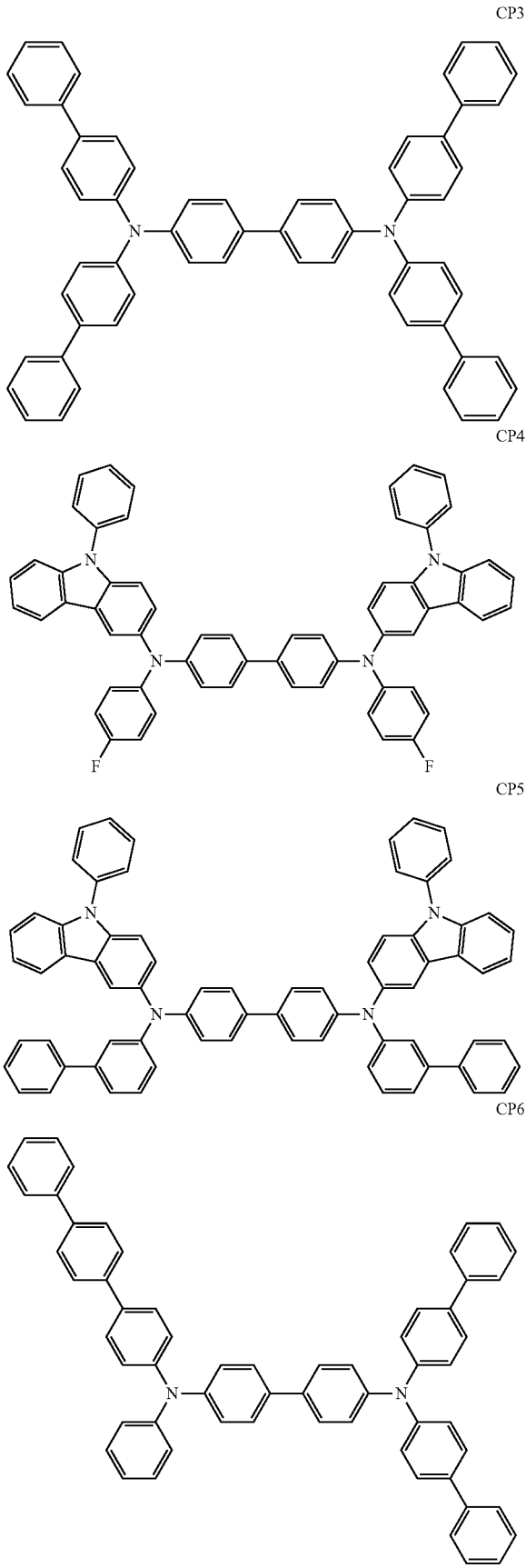

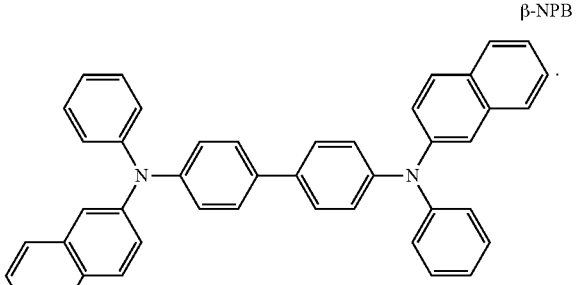

[Electronic Apparatus]

The light-emitting device may be included in various electronic apparatuses. In an embodiment, an electronic apparatus including the light-emitting device may be a light-emitting apparatus, an authentication apparatus, or the like.

The electronic apparatus (for example, a light-emitting apparatus) may further include, in addition to the light-emitting device, a color filter, a color conversion layer, or a color filter and a color conversion layer. The color filter and/or the color conversion layer may be located in at least one traveling direction of light emitted from the light-emitting device. In an embodiment, light emitted from the light-emitting device may be blue light or white light. The light-emitting device may be the same as described above. In an embodiment, the color conversion layer may include a quantum dot. The quantum dot may be, for example, a quantum dot as described herein.

The electronic apparatus may include a first substrate. The first substrate may include subpixels, the color filter may include color filter areas respectively corresponding to the subpixels, and the color conversion layer may include color conversion areas respectively corresponding to the subpixels.

A pixel-defining film may be between the subpixels to define each of the subpixels.

The color filter may further include color filter areas and light-blocking patterns between the color filter areas, and the color conversion layer may further include color conversion areas and light-blocking patterns between the color conversion areas.

The color filter areas (or the color conversion areas) may include a first area emitting first-color light, a second area emitting second-color light, and/or a third area emitting third-color light, and the first-color light, the second-color light, and/or the third-color light may have different maximum emission wavelengths from one another. In an embodiment, the first-color light may be red light, the second-color light may be green light, and the third-color light may be blue light. In an embodiment, the color filter areas (or the color conversion areas) may include quantum dots. The first area may include a red quantum dot, the second area may include a green quantum dot, and the third area may not include a quantum dot. The quantum dot is the same as described in the specification. Each of the first area, the second area and/or the third area may further include a scattering body.

In an embodiment, the light-emitting device may emit first light, the first area may absorb the first light to emit first first-color light, the second area may absorb the first light to emit second first-color light, and the third area may absorb the first light to emit third first-color light. In this regard, the first first-color light, the second first-color light, and the third first-color light may have different maximum emission wavelengths from one another. The first light may be blue light, the first first-color light may be red light, the second first-color light may be green light, and the third first-color light may be blue light.

The electronic apparatus may further include a thin-film transistor in addition to the light-emitting device as described above. The thin-film transistor may include a source electrode, a drain electrode, and an active layer, wherein any one of the source electrode and the drain electrode may be electrically connected to any one of the first electrode and the second electrode of the light-emitting device.

The thin-film transistor may further include a gate electrode, a gate insulation layer, or the like.

The active layer may include crystalline silicon, amorphous silicon, an organic semiconductor, an oxide semiconductor, or the like.

The electronic apparatus may further include a sealing portion for sealing the light-emitting device. The sealing portion may be between the color filter and/or the color conversion layer and the light-emitting device. The sealing portion allows light from the light-emitting device to be emitted to the outside, while simultaneously preventing ambient air and moisture from penetrating into the light-emitting device. The sealing portion may be a sealing substrate including a transparent glass substrate or a plastic substrate. The sealing portion may be a thin film encapsulation layer including one or more organic layers and/or one or more inorganic layers. When the sealing portion is a thin film encapsulation layer, the electronic apparatus may be flexible.

On the sealing portion, in addition to the color filter and/or the color conversion layer, various functional layers may be further located according to the use of the electronic apparatus. Examples of the functional layers may include a touch screen layer, a polarizing layer, and the like. The touch screen layer may be a pressure-sensitive touch screen layer, a capacitive touch screen layer, or an infrared touch screen layer. The authentication apparatus may be, for example, a biometric authentication apparatus for authenticating an individual by using biometric information of a biometric body (for example, a fingertip, a pupil, or the like).

The authentication apparatus may further include, in addition to the light-emitting device, a biometric information collector.

The electronic apparatus may be applied to various displays, light sources, lighting, personal computers (for example, a mobile personal computer), mobile phones, digital cameras, electronic organizers, electronic dictionaries, electronic game machines, medical instruments (for example, electronic thermometers, sphygmomanometers, blood glucose meters, pulse measurement devices, pulse wave measurement devices, electrocardiogram displays, ultrasonic diagnostic devices, or endoscope displays), fish finders, various measuring instruments, meters (for example, meters for a vehicle, an aircraft, and a vessel), projectors, and the like.

Figure 2:
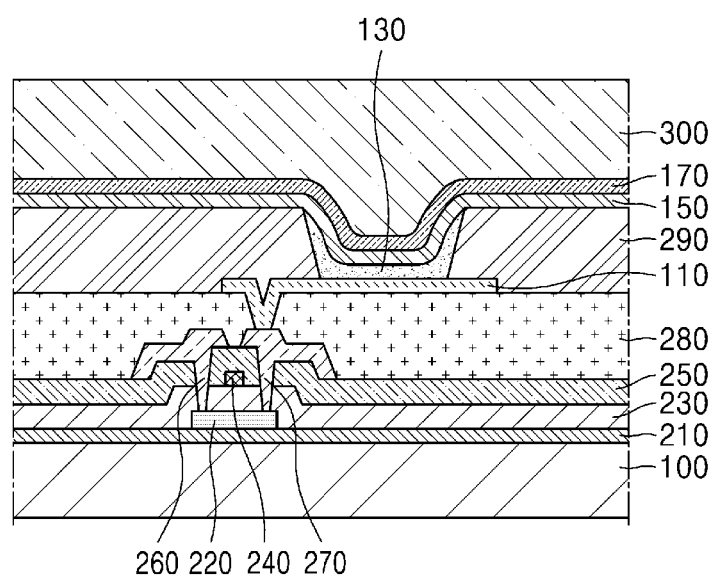
FIGS. 2 and 3 are each a schematic cross-sectional view of a structure of an electronic apparatus according to an embodiment.
Figure 3:
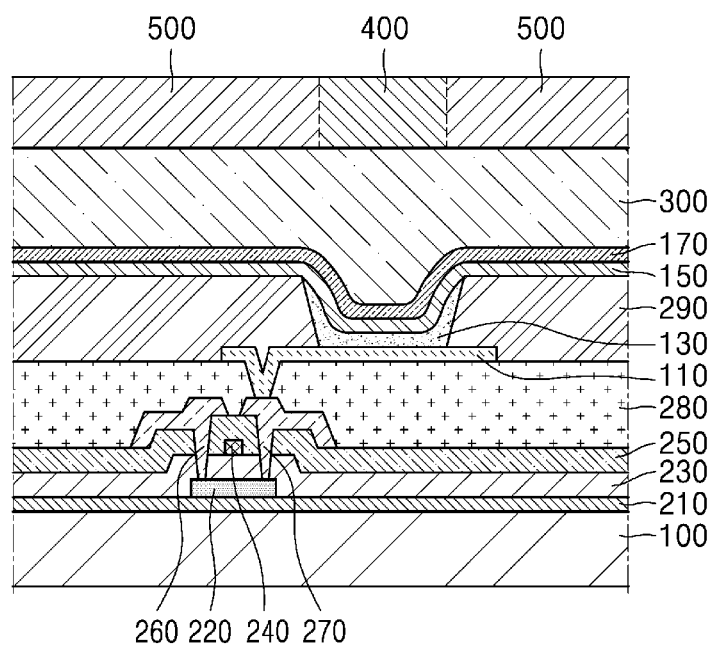

[Description of FIGS. 2 and 3]

FIG. 2 is a schematic cross-sectional view of a light-emitting apparatus according to an embodiment.

The light-emitting apparatus of FIG. 2 includes a substrate 100, a thin-film transistor (TFT), a light-emitting device, and an encapsulation portion 300 that seals the light-emitting device.

The substrate 100 may be a flexible substrate, a glass substrate, or a metal substrate. A buffer layer 210 may be on the substrate 100. The buffer layer 210 prevents penetration of impurities through the substrate 100 and may provide a flat surface on the substrate 100.

The TFT may be on the buffer layer 210. The TFT may include an active layer 220, a gate electrode 240, a source electrode 260, and a drain electrode 270.

The active layer 220 may include an inorganic semiconductor such as silicon or polysilicon, an organic semiconductor, or an oxide semiconductor, and may include a source region, a drain region, and a channel region.

A gate insulating film 230 for insulating the active layer 220 from the gate electrode 240 may be on the active layer 220, and the gate electrode 240 may be on the gate insulating film 230.

An interlayer insulating film 250 may be on the gate electrode 240. The interlayer insulating film 250 is located between the gate electrode 240 and the source electrode 260 to insulate the gate electrode 240 from the source electrode 260 and between the gate electrode 240 and the drain electrode 270 to insulate the gate electrode 240 from the drain electrode 270.

The source electrode 260 and the drain electrode 270 may be on the interlayer insulating film 250. The interlayer insulating film 250 and the gate insulating film 230 may be formed to expose the source region and the drain region of the active layer 220, and the source electrode 260 and the drain electrode 270 may be located to be in contact with the exposed portions of the source region and the drain region of the active layer 220.

The TFT may be electrically connected to the light-emitting device to drive the light-emitting device and may be protected by being covered with a passivation layer 280. The passivation layer 280 may include an inorganic insulating film, an organic insulating film, or a combination thereof. The light-emitting device is provided on the passivation layer 280. The light-emitting device includes the first electrode 110, the interlayer 130, and the second electrode 150.

The first electrode 110 may be on the passivation layer 280. The passivation layer 280 does not completely cover the drain electrode 270 and exposes a certain portion of the drain electrode 270, and the first electrode 110 may be connected to the exposed portion of the drain electrode 270.

A pixel defining layer 290 including an insulating material may be located on the first electrode 110. The pixel defining layer 290 may expose a certain region of the first electrode 110, and the interlayer 130 may be formed in the exposed region of the first electrode 110. The pixel defining layer 290 may be a polyimide or polyacryl-based organic film. Although not shown in FIG. 2, at least some layers of the interlayer 130 may extend beyond the upper portion of the pixel defining layer 290 and may thus be located in the form of a common layer.

The second electrode 150 may be located on the interlayer 130, and a capping layer 170 may be additionally formed on the second electrode 150. The capping layer 170 may be formed to cover the second electrode 150.

The encapsulation portion 300 may be located on the capping layer 170. The encapsulation portion 300 may be located on the light-emitting device and protects the light-emitting device from moisture or oxygen. The encapsulation portion 300 may include: an inorganic film including silicon nitride ($SiN_x$), silicon oxide ($SiO_x$), indium tin oxide, indium zinc oxide, or a combination thereof; an organic film including polyethylene terephthalate, polyethylene naphthalate, polycarbonate, polyimide, polyethylene sulfonate, polyoxymethylene, polyarylate, hexamethyldisiloxane, an acrylic resin (for example, polymethyl methacrylate or polyacrylic acid), an epoxy-based resin (for example, aliphatic glycidyl ether (AGE)), or any combination thereof; or a combination of an inorganic film and an organic film.

FIG. 3 is a schematic cross-sectional view of a light-emitting apparatus according to another embodiment.

The light-emitting apparatus of FIG. 3 is the same as the light-emitting apparatus of FIG. 2, except that a light-blocking pattern 500 and a functional region 400 are additionally located on the encapsulation portion 300. The functional region 400 may be a color filter area, a color conversion area, or a combination of the color filter area and the color conversion area. In an embodiment, the light-emitting device included in the light-emitting apparatus of FIG. 3 may be a tandem light-emitting device.

[Preparation Method]

Layers constituting the hole transport region, an emission layer, and layers constituting the electron transport region may be formed in a certain region by using one or more suitable methods selected from vacuum deposition, spin coating, casting, Langmuir-Blodgett (LB) deposition, ink-jet printing, laser-printing, and laser-induced thermal imaging.

When layers constituting the hole transport region, the emission layer, and layers constituting the electron transport region are formed by vacuum deposition, the deposition may be performed at a deposition temperature of about 100° C. to about 500° C., a vacuum degree of about $10^{-8}$ torr to about $10^{-3}$ torr, and a deposition speed of about 0.01 Å/sec to about 100 Å/sec by taking into account a material to be included in a layer to be formed and the structure of a layer to be formed.

Definition of Terms

The term "$C_3$-$C_{60}$ carbocyclic group" as used herein refers to a cyclic group that consists of carbon and hydrogen only and has three to sixty carbon atoms (for example 3 to 30, 3 to 24 or 3 to 18 carbon atoms), and the term "$C_1$-$C_{60}$ heterocyclic group" as used herein refers to a cyclic group that has one to sixty carbon atoms (for example 1 to 30, 1 to 24 or 1 to 18 carbon atoms) and further includes, in addition to carbon, a heteroatom (for example, 1 to 5 or 1 to 3, such as 1, 2, 3, 4 or 5 heteroatoms). The $C_3$-$C_{60}$ carbocyclic group and the $C_1$-$C_{60}$ heterocyclic group may each be a monocyclic group that consists of one ring or a polycyclic group in which two or more rings are condensed with each other. In an embodiment, the number of ring-forming atoms of the $C_1$-$C_{60}$ heterocyclic group may be from 3 to 61.

The term "cyclic group" as used herein includes the $C_3$-$C_{60}$ carbocyclic group and the $C_1$-$C_{60}$ heterocyclic group.

The term "π electron-rich $C_3$-$C_{60}$ cyclic group" as used herein refers to a cyclic group that has three to sixty carbon atoms (for example 3 to 30, 3 to 24 or 3 to 18 carbon atoms) and does not include *—N=*' as a ring-forming moiety, and the term "π-electron-deficient nitrogen-containing $C_1$-$C_{60}$ cyclic group" as used herein refers to a heterocyclic group that has one to sixty carbon atoms (for example 1 to 30, 1 to 24 or 1 to 18 carbon atoms) and includes *—N=*' as a ring-forming moiety.

In an embodiment, the $C_3$-$C_{60}$ carbocyclic group may be i) a group $T_1$ or ii) a condensed cyclic group in which two or more groups $T_1$ are condensed with each other (for example, a cyclopentadiene group, an adamantane group, a norbornane group, a benzene group, a pentalene group, a naphthalene group, an azulene group, an indacene group, acenaphthylene group, a phenalene group, a phenanthrene group, an anthracene group, a fluoranthene group, a triphenylene group, a pyrene group, a chrysene group, a perylene group, a pentaphene group, a heptalene group, a naphthacene group, a picene group, a hexacene group, a pentacene group, a rubicene group, a coronene group, an ovalene group, an indene group, a fluorene group, a spiro-bifluorene group, a benzofluorene group, an indenophenanthrene group, or an indenoanthracene group), the $C_1$-$C_{60}$ heterocyclic group may be i) a group $T_2$, ii) a condensed cyclic group in which two or more groups $T_2$ are condensed with each other, or iii) a condensed cyclic group in which at least one group $T_2$ and at least one group $T_1$ are condensed with each other (for example, a pyrrole group, a thiophene group, a furan group, an indole group, a benzoindole group, a naphthoindole group, an isoindole group, a benzoisoindole group, a naphthoisoindole group, a benzosilole group, a benzothiophene group, a benzofuran group, a carbazole group, a dibenzosilole group, a dibenzothiophene group, a dibenzofuran group, an indenocarbazole group, an indolocarbazole group, a benzofurocarbazole group, a benzothienocarbazole group, a benzosilolocarbazole group, a benzoindolocarbazole group, a benzocarbazole group, a benzonaphthofuran group, a benzonaphthothiophene group, a benzonaphthosilole group, a benzofurodibenzofuran group, a benzofurodibenzothiophene group, a benzothieno dibenzothiophene group, a pyrazole group, an imidazole group, a triazole group, an oxazole group, an isoxazole group, an oxadiazole group, a thiazole group, an isothiazole group, a thiadiazole group, a benzopyrazole group, a benzimidazole group, a benzoxazole group, a benzoisoxazole group, a benzothiazole group, a benzoisothiazole group, a pyridine group, a pyrimidine group, a pyrazine group, a pyridazine group, a triazine group, a quinoline group, an isoquinoline group, a benzoquinoline group, a benzoisoquinoline group, a quinoxaline group, a benzoquinoxaline group, a quinazoline group, a benzoquinazoline group, a phenanthroline group, a cinnoline group, a phthalazine group, a naphthyridine group, an imidazopyridine group, an imidazopyrimidine group, an imidazotriazine group, an imidazopyrazine group, an imidazopyridazine group, an azacarbazole group, an azafluorene group, an azadibenzosilole group, an azadibenzothiophene group, or an azadibenzofuran group), the π electron-rich $C_3$-$C_{60}$ cyclic group may be i) a group $T_1$, ii) a condensed cyclic group in which two or more groups $T_1$ are condensed with each other, iii) a group $T_3$, iv) a condensed cyclic group in which two or more groups $T_3$ are condensed with each other, or v) a condensed cyclic group in which at least one group $T_3$ and at least one group $T_1$ are condensed with each other (for example, a $C_3$-$C_{60}$ carbocyclic group, a pyrrole group, a thiophene group, a furan group, an indole group, a benzoindole group, a naphthoindole group, an isoindole group, a benzoisoindole group, a naphthoisoindole group, a benzosilole group, a benzothiophene group, a benzofuran group, a carbazole group, a dibenzosilole group, a dibenzothiophene group, a dibenzofuran group, an indenocarbazole group, an indolocarbazole group, a benzofurocarbazole group, a benzothienocarbazole group, a benzosilolocarbazole group, a benzoindolocarbazole group, a benzocarbazole group, a benzonaphthofuran group, a benzonaphthothiophene group, a benzonaphthosilole group, a benzofurodibenzofuran group, a benzofurodibenzothiophene group, or a benzothienodibenzothiophene group), the π-electron-deficient nitrogen-containing $C_1$-$C_{60}$ cyclic group may be i) a group $T_4$, ii) a condensed cyclic group in which two or more groups $T_4$ are condensed with each other, iii) a condensed cyclic group in which at least one group $T_4$ and at least one group $T_1$ are condensed with each other, iv) a condensed cyclic group in which at least one group $T_4$ and at least one group $T_3$ are condensed with each other, or v) a condensed cyclic group in which at least one group $T_4$, at least one group $T_1$, and at least one group $T_3$ are condensed with each other (for example, a pyrazole group, an imidazole group, a triazole group, an oxazole group, an isoxazole group, an oxadiazole group, a thiazole group, an isothiazole group, a thiadiazole group, a benzopyrazole group, a benzimidazole group, a benzoxazole group, a benzoisoxazole group, a benzothiazole group, a benzoisothiazole group, a pyridine group, a pyrimidine group, a pyrazine group, a pyridazine group, a triazine group, a quinoline group, an isoquinoline group, a benzoquinoline group, a benzoisoquinoline group, a quinoxaline group, a benzoquinoxaline group, a quinazoline group, a benzoquinazoline group, a phenanthroline group, a cinnoline group, a phthalazine group, a naphthyridine group, an imidazopyridine group, an imidazopyrimidine group, an imidazotriazine group, an imidazopyrazine group, an imidazopyridazine group, an azacarbazole group, an azafluorene group, an azadibenzosilole group, an azadibenzothiophene group, or an azadibenzofuran group), the group $T_1$ may be a cyclopropane group, a cyclobutane group, a cyclopentane group, a cyclohexane group, a cycloheptane group, a cyclooctane group, a cyclobutene group, a cyclopentene group, a cyclopentadiene group, a cyclohexene group, a cyclohexadiene group, a cycloheptene group, an adamantane group, a norbornane group (or, a bicyclo[2.2.1]heptane group), a norbornene group, a bicyclo[1.1.1]pentane group, a bicyclo[2.1.1]hexane group, a bicyclo[2.2.2]octane group, or a benzene group, the group $T_2$ may be a furan group, a thiophene group, a 1H-pyrrole group, a silole group, a borole group, a 2H-pyrrole group, a 3H-pyrrole group, an imidazole group, a pyrazole group, a triazole group, a tetrazole group, an oxazole group, an isoxazole group, an oxadiazole group, a thiazole group, an isothiazole group, a thiadiazole group, an azasilole group, an azaborole group, a pyridine group, a pyrimidine group, a pyrazine group, a pyridazine group, a triazine group, or a tetrazine group, the group $T_3$ may be a furan group, a thiophene group, a 1H-pyrrole group, a silole group, or a borole group, and the group $T_4$ may be a 2H-pyrrole group, a 3H-pyrrole group, an imidazole group, a pyrazole group, a triazole group, a tetrazole group, an oxazole group, an isoxazole group, an oxadiazole group, a thiazole group, an isothiazole group, a thiadiazole group, an azasilole group, an azaborole group, a pyridine group, a pyrimidine group, a pyrazine group, a pyridazine group, a triazine group, or a tetrazine group.

The term "the cyclic group, the $C_3$-$C_{60}$ carbocyclic group, the $C_1$-$C_{60}$ heterocyclic group, the π electron-rich $C_3$-$C_{60}$ cyclic group, or the π-electron-deficient nitrogen-containing $C_1$-$C_{60}$ cyclic group" as used herein refer to a group that is condensed with a cyclic group, a monovalent group, a polyvalent group (for example, a divalent group, a trivalent group, a tetravalent group, or the like), according to the structure of a formula described with corresponding terms. In an embodiment, "a benzene group" may be a benzo group, a phenyl group, a phenylene group, or the like, which may be easily understand by one of ordinary skill in the art according to the structure of a formula including the "benzene group."

In an embodiment, examples of the monovalent $C_3$-$C_{60}$ carbocyclic group and the monovalent $C_1$-$C_{60}$ heterocyclic group may include a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group, and examples of the divalent $C_3$-$C_{60}$ carbocyclic group and the divalent $C_1$-$C_{60}$ heterocyclic group may include a $C_3$-$C_{10}$ cycloalkylene group, a $C_1$-$C_{10}$ heterocycloalkylene group, a $C_3$-$C_{10}$ cycloalkenylene group, a $C_1$-$C_{10}$ heterocycloalkenylene group, a $C_6$-$C_{60}$ arylene group, a $C_1$-$C_{60}$ heteroarylene group, a divalent non-aromatic condensed polycyclic group, and a divalent non-aromatic condensed heteropolycyclic group.

The term "$C_1$-$C_{60}$ alkyl group" as used herein refers to a linear or branched aliphatic hydrocarbon monovalent group having 1 to 60 carbon atoms, and examples thereof includes a methyl group, an ethyl group, an n-propyl group, an isopropyl group, an n-butyl group, a sec-butyl group, an isobutyl group, a tert-butyl group, an n-pentyl group, a tert-pentyl group, a neopentyl group, an isopentyl group, a sec-pentyl group, a 3-pentyl group, a sec-isopentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, and a tert-decyl group. In embodiments, $C_1$-$C_{60}$ alkyl group may be $C_1$-$C_{30}$ alkyl group, $C_1$-$C_{20}$ alkyl group or $C_1$-$C_{10}$ alkyl group. The term "$C_1$-$C_{60}$ alkylene group" as used herein refers to a divalent group having the same structure as the $C_1$-$C_{60}$ alkyl group.

The term "$C_2$-$C_{60}$ alkenyl group" as used herein refers to a monovalent hydrocarbon group having at least one carbon-carbon double bond in the middle or at the terminus of a $C_2$-$C_{60}$ alkyl group, and examples thereof include an ethenyl group, a propenyl group, and a butenyl group. In embodiments, $C_2$-$C_{60}$ alkenyl group may be $C_2$-$C_{30}$ alkenyl group, $C_2$-$C_{20}$ alkenyl group or $C_2$-$C_{10}$ alkenyl group. The term "$C_2$-$C_{60}$ alkenylene group" as used herein refers to a divalent group having the same structure as the $C_2$-$C_{60}$ alkenyl group.

The term "$C_2$-$C_{60}$ alkynyl group" as used herein refers to a monovalent hydrocarbon group having at least one carbon-carbon triple bond in the middle or at the terminus of a $C_2$-$C_{60}$ alkyl group, and examples thereof include an ethynyl group and a propynyl group. In embodiments, $C_2$-$C_{60}$ alkynyl group may be $C_2$-$C_{30}$ alkynyl group, $C_2$-$C_{20}$ alkynyl group or $C_2$-$C_{10}$ alkynyl group. The term "$C_2$-$C_{60}$ alkynylene group" as used herein refers to a divalent group having the same structure as the $C_2$-$C_{60}$ alkynyl group.

The term "$C_1$-$C_{60}$ alkoxy group" as used herein refers to a monovalent group represented by —$OA_{101}$ (wherein $A_{101}$ is the $C_1$-$C_{60}$ alkyl group), and examples thereof include a methoxy group, an ethoxy group, and an isopropyloxy group.

The term "$C_3$-$C_{10}$ cycloalkyl group" as used herein refers to a monovalent saturated hydrocarbon cyclic group having 3 to 10 carbon atoms, and examples thereof include a cyclopropyl group, a cyclobutyl group, a cyclopentyl group, a cyclohexyl group, a cycloheptyl group, a cyclooctyl group, an adamantanyl group, a norbornanyl group (or a bicyclo[2.2.1]heptyl group), a bicyclo[1.1.1]pentyl group, a bicyclo[2.1.1]hexyl group, and a bicyclo [2.2.2]octyl group. The term "$C_3$-$C_{10}$ cycloalkylene group" as used herein refers to a divalent group having the same structure as the $C_3$-$C_{10}$ cycloalkyl group.

The term "$C_1$-$C_{10}$ heterocycloalkyl group" as used herein refers to a monovalent cyclic group that further includes, in addition to a carbon atom, at least one heteroatom (for example, 1 to 5 or 1 to 3, such as 1, 2, 3, 4 or 5 heteroatoms) as a ring-forming atom and has 1 to 10 carbon atoms, and examples thereof include a1,2,3,4-oxatriazolidinyl group, a tetrahydrofuranyl group, and a tetrahydrothiophenyl group. The term "$C_1$-$C_{10}$ heterocycloalkylene group" as used herein refers to a divalent group having the same structure as the $C_1$-$C_{10}$ heterocycloalkyl group.

The term "$C_3$-$C_{10}$ cycloalkenyl group" as used herein refers to a monovalent cyclic group that has 3 to 10 carbon atoms and at least one carbon-carbon double bond in the ring thereof and no aromaticity, and examples thereof include a cyclopentenyl group, a cyclohexenyl group, and a cycloheptenyl group. The term "$C_3$-$C_{10}$ cycloalkenylene group" as used herein refers to a divalent group having the same structure as the $C_3$-$C_{10}$ cycloalkenyl group.

The term "$C_1$-$C_{10}$ heterocycloalkenyl group" as used herein refers to a monovalent cyclic group that has, in addition to a carbon atom, at least one heteroatom (for example, 1 to 5 or 1 to 3, such as 1, 2, 3, 4 or 5 heteroatoms) as a ring-forming atom, 1 to 10 carbon atoms, and at least one double bond in the cyclic structure thereof. Examples of the $C_1$-$C_{10}$ heterocycloalkenyl group include a 4,5-dihydro-1,2,3,4-oxatriazolyl group, a 2,3-dihydrofuranyl group, and a 2,3-dihydrothiophenyl group. The term "$C_1$-$C_{10}$ heterocycloalkenylene group" as used herein refers to a divalent group having the same structure as the $C_1$-$C_{10}$ heterocycloalkenyl group.

The term "$C_6$-$C_{60}$ aryl group" as used herein refers to a monovalent group having a carbocyclic aromatic system having 6 to 60 carbon atoms, and the term "$C_6$-$C_{60}$ arylene group" as used herein refers to a divalent group having a carbocyclic aromatic system having 6 to 60 carbon atoms. Examples of the $C_6$-$C_{60}$ aryl group include a phenyl group, a pentalenyl group, a naphthyl group, an azulenyl group, an indacenyl group, an acenaphthyl group, a phenalenyl group, a phenanthrenyl group, an anthracenyl group, a fluoranthenyl group, a triphenylenyl group, a pyrenyl group, a chrysenyl group, a perylenyl group, a pentaphenyl group, a heptalenyl group, a naphthacenyl group, a picenyl group, a hexacenyl group, a pentacenyl group, a rubicenyl group, a coronenyl group, and an ovalenyl group. In embodiments, $C_6$-$C_{60}$ aryl group may be $C_6$-$C_{30}$ aryl group, $C_6$-$C_{24}$ aryl group or $C_6$-$C_{18}$ aryl group. When the $C_6$-$C_{60}$ aryl group and the $C_6$-$C_{60}$ arylene group each include two or more rings, the two or more rings may be condensed to each other.

The term "$C_1$-$C_{60}$ heteroaryl group" as used herein refers to a monovalent group having a heterocyclic aromatic system that has, in addition to a carbon atom, at least one heteroatom (for example, 1 to 5 or 1 to 3, such as 1, 2, 3, 4 or 5 heteroatoms) as a ring-forming atom, and 1 to 60 carbon atoms. The term "$C_1$-$C_{60}$ heteroarylene group" as used herein refers to a divalent group having a heterocyclic aromatic system that has, in addition to a carbon atom, at least one heteroatom (for example, 1 to 5 or 1 to 3, such as 1, 2, 3, 4 or 5 heteroatoms) as a ring-forming atom, and 1 to 60 carbon atoms. Examples of the $C_1$-$C_{60}$ heteroaryl group include a pyridinyl group, a pyrimidinyl group, a pyrazinyl group, a pyridazinyl group, a triazinyl group, a quinolinyl group, a benzoquinolinyl group, an isoquinolinyl group, a benzoisoquinolinyl group, a quinoxalinyl group, a benzoquinoxalinyl group, a quinazolinyl group, a benzoquinazolinyl group, a cinnolinyl group, a phenanthrolinyl group, a phthalazinyl group, and a naphthyridinyl group. In some embodiments, $C_1$-$C_{60}$ heteroaryl group may be $C_1$-$C_{30}$ heteroaryl group, $C_1$-$C_{24}$ heteroaryl group or $C_1$-$C_{18}$ heteroaryl group. When the $C_1$-$C_{60}$ heteroaryl group and the $C_1$-$C_{60}$ heteroarylene group each include two or more rings, the two or more rings may be condensed with each other.

The term "monovalent non-aromatic condensed polycyclic group" as used herein refers to a monovalent group (for example, having 8 to 60 carbon atoms, such as 8 to 30 or 8 to 24 carbon atoms) having two or more rings condensed with each other, only carbon atoms as ring-forming atoms, and non-aromaticity in its entire molecular structure. Examples of the monovalent non-aromatic condensed polycyclic group include an indenyl group, a fluorenyl group, a spiro-bifluorenyl group, a benzofluorenyl group, an indenophenanthrenyl group, and an indenoanthracenyl group. The term "divalent non-aromatic condensed polycyclic group" as used herein refers to a divalent group having the same structure as the monovalent non-aromatic condensed polycyclic group.

The term "monovalent non-aromatic condensed heteropolycyclic group" as used herein refers to a monovalent group (for example, having 1 to 60 carbon atoms, such as 1 to 30 or 1 to 24 carbon atoms) having two or more rings condensed to each other, at least one heteroatom other than carbon atoms (for example, 1 to 5 or 1 to 3, such as 1, 2, 3, 4 or 5 heteroatoms), as a ring-forming atom, and non-aromaticity in its entire molecular structure. Examples of the monovalent non-aromatic condensed heteropolycyclic group include a pyrrolyl group, a thiophenyl group, a furanyl group, an indolyl group, a benzoindolyl group, a naphthoindolyl group, an isoindolyl group, a benzoisoindolyl group, a naphthoisoindolyl group, a benzosilolyl group, a benzothiophenyl group, a benzofuranyl group, a carbazolyl group, a dibenzosilolyl group, a dibenzothiophenyl group, a dibenzofuranyl group, an azacarbazolyl group, an azafluorenyl group, an azadibenzosilolyl group, an azadibenzothiophenyl group, an azadibenzofuranyl group, a pyrazolyl group, an imidazolyl group, a triazolyl group, a tetrazolyl group, an oxazolyl group, an isoxazolyl group, a thiazolyl group, an isothiazolyl group, an oxadiazolyl group, a thiadiazolyl group, a benzopyrazolyl group, a benzimidazolyl group, a benzoxazolyl group, a benzothiazolyl group, a benzoxadiazolyl group, a benzothiadiazolyl group, an imidazopyridinyl group, an imidazopyrimidinyl group, an imidazotriazinyl group, an imidazopyrazinyl group, an imidazopyridazinyl group, an indenocarbazolyl group, an indolocarbazolyl group, a benzofurocarbazolyl group, a benzothienocarbazolyl group, a benzosilolocarbazolyl group, a benzoindolocarbazolyl group, a benzocarbazolyl group, a benzonaphthofuranyl group, a benzonaphthothiophenyl group, a benzonaphthosilolyl group, a benzofurodibenzofuranyl group, a benzofurodibenzothiophenyl group, and a benzothienodibenzothiophenyl group. The term "divalent non-aromatic condensed heteropolycyclic group" as used herein refers to a divalent group having the same structure as the monovalent non-aromatic condensed heteropolycyclic group.

The term "$C_6$-$C_{60}$ aryloxy group" as used herein refers to —$OA_{102}$ (wherein $A_{102}$ is the $C_6$-$C_{60}$ aryl group), and the term "$C_6$-$C_{60}$ arylthio group" as used herein refers to —$SA_{103}$ (wherein $A_{103}$ is the $C_6$-$C_{60}$ aryl group).

The group $R_{10a}$ as used herein may be:

deuterium (-D), —F, —Cl, —Br, —I, a hydroxyl group, a cyano group, or a nitro group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each unsubstituted or substituted with deuterium, —F, —Cl, —Br, —I, a hydroxyl group, a cyano group, a nitro group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, —$C(Q_{11})(Q_{12})(Q_{13})$, —$Si(Q_{11})(Q_{12})(Q_{13})$, —$N(Q_{11})(Q_{12})$, —$B(Q_{11})(Q_{12})$, —$C(=O)(Q_{11})$, —$S(=O)_2(Q_{11})$, —$P(=O)(Q_{11})(Q_{12})$, or any combination thereof;

a $C_3$-$C_{60}$ carbocyclic group, a $C_1$-$C_{60}$ heterocyclic group, a $C_6$-$C_{60}$ aryloxy group, or a $C_6$-$C_{60}$ arylthio group, each unsubstituted or substituted with deuterium, —F, —Cl, —Br, —I, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, —$C(Q_{21})(Q_{22})(Q_{23})$, —$Si(Q_{21})(Q_{22})(Q_{23})$, —$N(Q_{21})(Q_{22})$, —$B(Q_{21})(Q_{22})$, —$C(=O)(Q_{21})$, —$S(=O)_2(Q_{21})$, —$P(=O)(Q_{21})(Q_{22})$, or any combination thereof; or —$C(Q_{31})(Q_{32})(Q_{33})$, —$Si(Q_{31})(Q_{32})(Q_{33})$, —$N(Q_{31})(Q_{32})$, —$B(Q_{31})(Q_{32})$, —$C(=O)(Q_{31})$, —$S(=O)_2(Q_{31})$, or —$P(=O)(Q_{31})(Q_{32})$.

$Q_1$ to $Q_3$, $Q_{11}$ to $Q_{13}$, $Q_{21}$ to $Q_{23}$ and $Q_{31}$ to $Q_{33}$ as used herein may each independently be: hydrogen; deuterium; —F; —Cl; —Br; —I; a hydroxyl group; a cyano group; a nitro group; a $C_1$-$C_{60}$ alkyl group; a $C_2$-$C_{60}$ alkenyl group; a $C_2$-$C_{60}$ alkynyl group; a $C_1$-$C_{60}$ alkoxy group; or a $C_3$-$C_{60}$ carbocyclic group or a $C_1$-$C_{60}$ heterocyclic group, each unsubstituted or substituted with deuterium, —F, a cyano group, a $C_1$-$C_{60}$ alkyl group, a $C_1$-$C_{60}$ alkoxy group, a phenyl group, a biphenyl group, or any combination thereof.

The term "heteroatom" as used herein refers to any atom other than a carbon atom and a hydrogen atom. Examples of the heteroatom include O, S, N, P, Si, B, Ge, Se, or any combination thereof.

The term "Ph" as used herein refers to a phenyl group, the term "Me" as used herein refers to a methyl group, the term "Et" as used herein refers to an ethyl group, the term "tert-Bu" or "Bu$^t$" as used herein refers to a tert-butyl group, and the term "OMe" as used herein refers to a methoxy group.

The term "biphenyl group" as used herein refers to "a phenyl group substituted with a phenyl group." In other words, the "biphenyl group" is a substituted phenyl group having a $C_6$-$C_{60}$ aryl group as a substituent.

The term "terphenyl group" as used herein refers to "a phenyl group substituted with a biphenyl group". In other words, the "terphenyl group" is a substituted phenyl group having, as a substituent, a $C_6$-$C_{60}$ aryl group substituted with a $C_6$-$C_{60}$ aryl group.

* and *' as used herein, unless defined otherwise, each refer to a binding site to a neighboring atom in a corresponding formula.

Hereinafter, a compound according to embodiments and a light-emitting device according to embodiments will be described in detail with reference to Synthesis Examples and Examples. The wording "B was used instead of A" used in describing Synthesis Examples refers to that an identical molar equivalent of B was used in place of A.

EXAMPLES

Synthesis Example 1: Synthesis of Compound 1-1

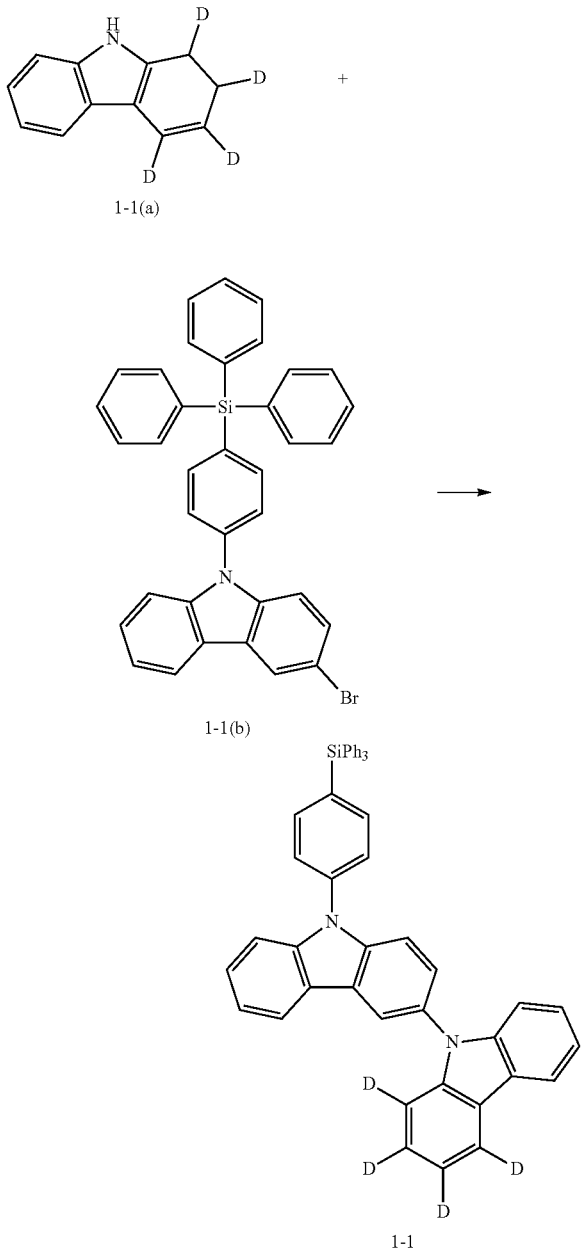

Synthesis of Intermediate 1-1 (a)

1) Synthesis of Intermediate A-1

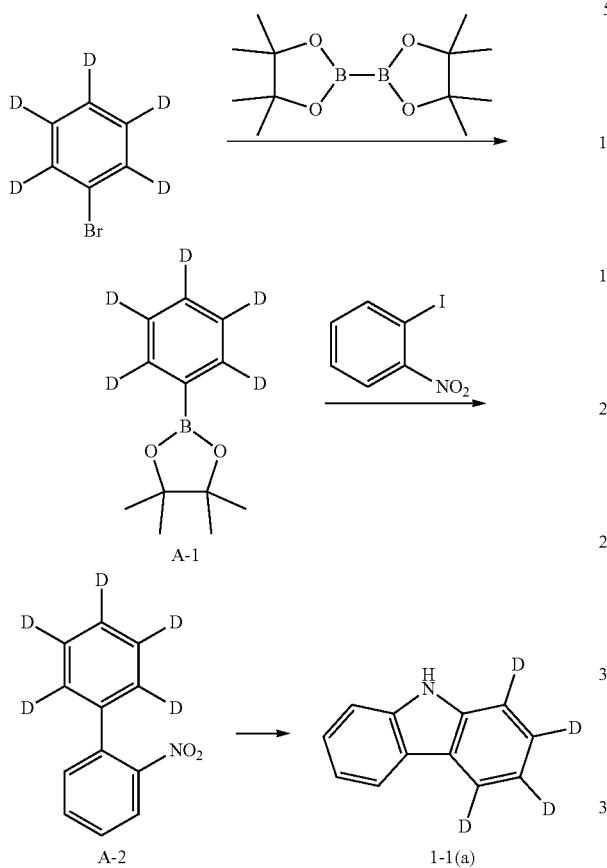

Bromobenzene-d5 (25 g, 1 eq), 4,4,4',4', 5,5,5',5'-octamethyl-2,2'-bi(1,3,2-dioxaborolane) (47 g, 1.2 eq), potassium acetate (37.8 g, 2.5 eq), bis(triphenylphosphine)-palladium (II) dichloride (5.4 g, 0.05 eq), and toluene (770 mL) were put into a round bottom flask (RBF), and stirred overnight while refluxing at 130° C. After completion of the reaction, a solvent was removed therefrom by a silica filtration using dichloromethane (MC) and purified by a column chromatography by using hexane. The resultant was solidified by using MeOH and dried, to thereby obtain Intermediate A-1. (yield of 77%)

$C_{12}H_{12}D_5BO_2$ [M]+: calculation: 209.11, measurement: 208

2) Synthesis of Intermediate A-2

1-Iodo-2-nitrobenzene (27 g, 1 eq), Intermediate A-1 (25 g, 1.1 eq), $K_2CO_3$ (37.6 g, 2.5 eq), tetrakis(triphenylphosphine)palladium (5 g, 0.04 eq), THF (540 mL), and $H_2O$ (135 mL) were put into an RBF, and stirred overnight while refluxing at 90° C. After completion of the reaction, a work-up was performed by using $EA/H_2O$, and a solvent was removed therefrom. After the reactant was dissolved in a small amount of MC and subjected to a silica filtration using hexane and MC at a volume ratio of 1:1, a solvent was removed therefrom. The resultant was solidified by using MeOH and dried, to thereby obtain Intermediate A-2. (29 g (Crude))

$C_{12}H_4D_5NO_2$ [M]+: calculation: 204.24, measurement: 203

3) Synthesis of Intermediate 1-1 (a)

2-nitro-1,1'-biphenyl-2',3',4',5',6'-d5 (29.5 g, 1 eq), triphenylphosphine (71 g, 2.5 eq), and 1,2-dichlorobenzene (500 mL) were put into an RBF, and stirred overnight while refluxing at 200° C. After completion of the reaction, the reactant was cooled to room temperature, and a solvent was removed therefrom as much as possible. After a silica filtration using hexane and MC at a volume ratio of 2:1, the solvent was removed therefrom. The resultant was solidified by using hexane and dried, and subjected to a sublimation purification (final temperature=160° C.), to thereby obtain Intermediate 1-1(a). (yield of 55.7%)

$C_{12}H_5D_4N$ [M]+: calculation: 171.24, measurement: 170

Synthesis of Intermediate 1-1 (b)

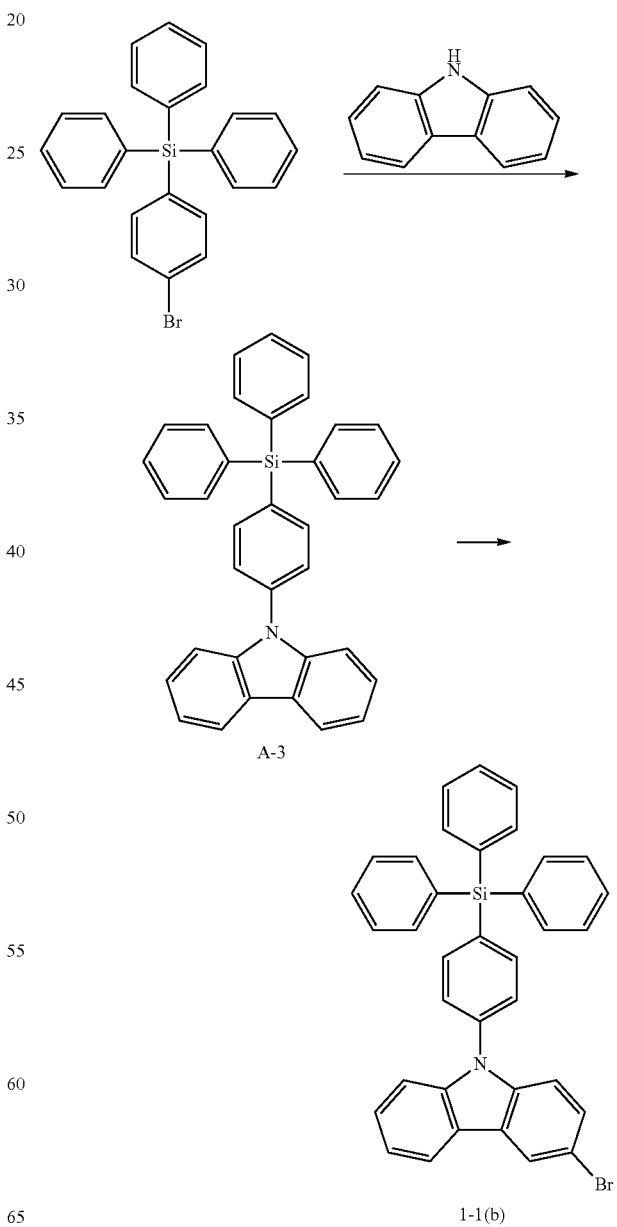

1) Synthesis of Intermediate A-3

(4-bromophenyl)triphenylsilane (10 g, 1 eq), 9H-carbazole (4.4 g, 1 eq), sodium tert-butoxide (3.5 g, 1.5 eq), tris(dibenzylideneacetone)dipalladium (0) (0.88 g, 0.04 eq), tri-tert-butylphosphine (0.8 mL, 0.08 eq), and toluene (120 mL) were put into an RBF, and stirred overnight while refluxing at 130° C. After completion of the reaction, the reactant was subjected to a silica filtration using MC, and a solvent was removed therefrom. The resultant was purified by a column chromatography by using hexane and MC at a volume ratio of 4:1. The resultant was solidified by using MeOH and subjected to filtration and drying, to thereby obtain Intermediate A-3. (yield of 91%)

$C_{36}H_{27}NSi$ [M]+: calculation: 501.70, measurement: 500

2) Synthesis of Intermediate 1-1(b)

In an RBF, Intermediate A-3 (11 g, 1 eq) was dissolved in dimethylformamide (DMF) (200 mL) and stirred at 0° C. for 30 minutes. N-bromosuccinimide (NBS) (3.8 g, 0.95 eq) dissolved in DMF (20 mL) was slowly added dropwise thereto and stirred at room temperature overnight. After completion of the reaction, $H_2O$ was added thereto and stirred, and a solid generated therefrom was subjected to filtration. Afterward, the dried solid was dissolved in MC and treated with $MgSO_4$, and a solvent was removed therefrom. After a silica filtration using MC, the solvent was removed therefrom. The resultant was solidified by using MeOH and dried, to thereby obtain Intermediate 1-1(b). (yield of 78%)

$C_{36}H_{26}BrNSi$ [M]+: calculation: 580.60, measurement: 579

Synthesis of Compound 1-1

Intermediate 1-1 (b) (1 eq), Intermediate 1-1 (a) (1.2 eq), sodium tert-butoxide (1.5 eq), tris(dibenzylideneacetone) dipalladium (0) (0.04 eq), tri-tert-butylphosphine (0.08 eq), and toluene (110 mL) were put into an RBF, and stirred overnight while refluxing at 130° C. After completion of the reaction, the reactant was subjected to a silica filtration using MC, and a solvent was removed therefrom. The resultant was purified by a column chromatography by using hexane and MC at a volume ratio of 8:1. The resultant was solidified by using MeOH, dried, and dissolved by boiling in toluene (25 mL). Hexane (50 mL) was added dropwise thereto and subjected to solidification and filtration (amount of solvent at 8.5 g), to thereby obtain Compound 1-1. (yield of 78.4%)

$C_{48}H_{30}D_4N_2Si$ [M]+: calculation: 670.27, measurement: 669

Elemental Analysis Calculated: C, 85.93; H, 5.71; N, 4.18; Si, 4.19

Synthesis Example 2: Synthesis of Compound 1-5

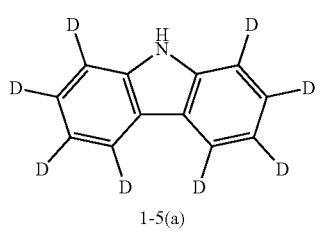

1-5(a)

+

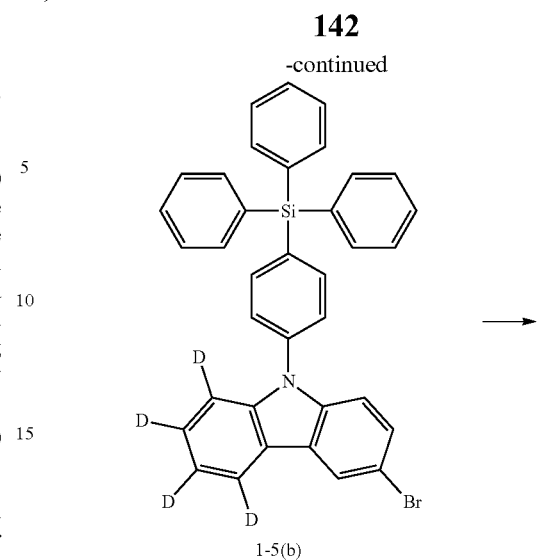

1-5(b)

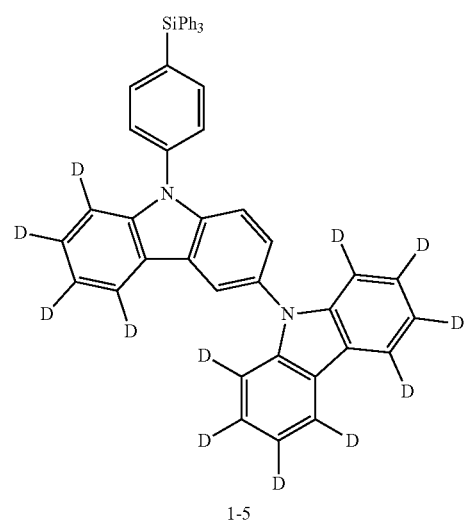

1-5

Synthesis of Intermediate 1-5(b)

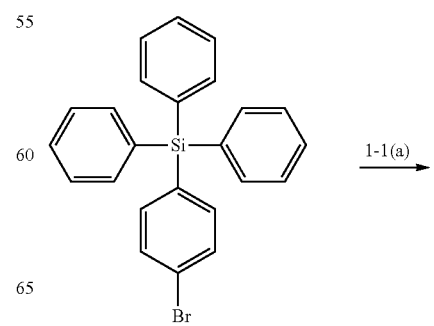

1-1(a)

143
-continued

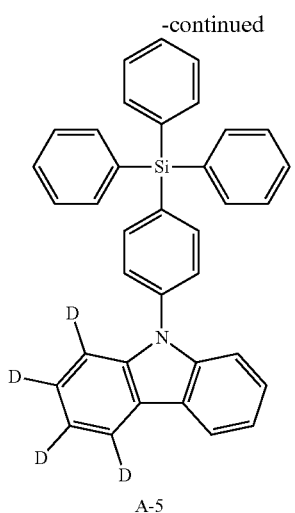

A-5

1-5(b)

1) Synthesis of Intermediate A-5

Intermediate A-5 was synthesized in the same manner as used in the synthesis method of Intermediate A-3, except that Intermediate 1-1 (a) was used instead of 9H-carbazole.

$C_{36}H_{23}D_4NSi$ [M]+: calculation: 505.73, measurement: 504

2) Synthesis of Intermediate 1-5(b)

Intermediate 1-5(b) was synthesized in the same manner as used in the synthesis method of Intermediate 1-1(b), except that Intermediate A-5 was used instead of Intermediate A-3.

$C_{36}H_{22}D_4BrNSi$ [M]+: calculation: 584.73, measurement: 583

Synthesis of Compound 1-5

Compound 1-5 was synthesized in the same manner as used in the synthesis method of Compound 1-1, except that Intermediate 1-5(b) was used instead of Intermediate 1-1 (b), and Intermediate 1-5(a) was used instead of Intermediate 1-1 (a).

$C_{48}H_{22}D_{12}N_2Si$ [M]+: calculation: 678.97, measurement: 677

Elemental Analysis Calculated: C, 84.91; H, 6.83; N, 4.13; Si, 4.14

144

Synthesis Example 3: Synthesis of Compound 1-7

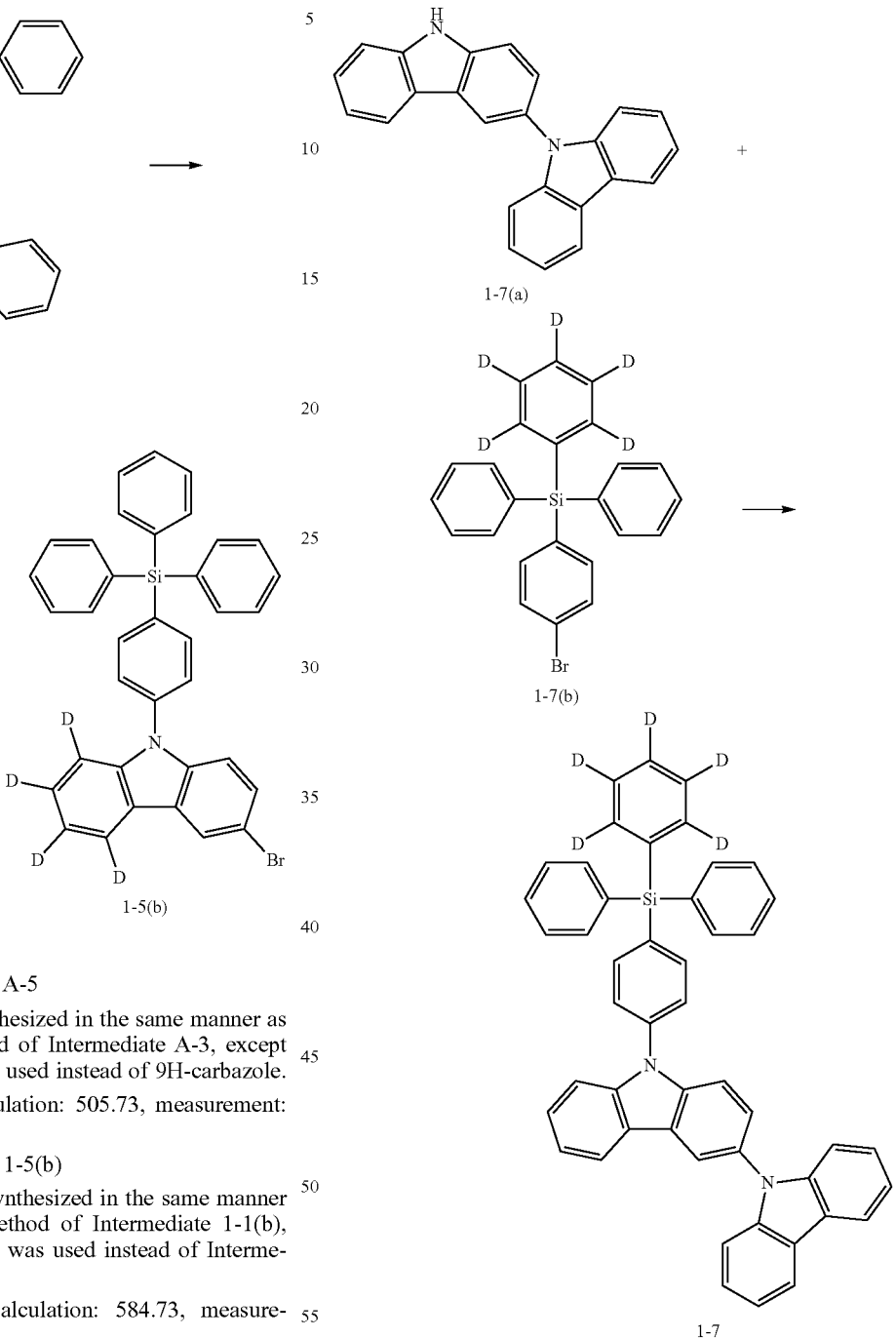

Pd(dba)$_3$ (0.03 eq), (t-Bu)$_3$P (0.06 eq), and toluene (0.1 M based on 1 eq of reagent) were added into a flask containing 1 eq of Intermediate 1-7(b) and 1.1 eq of Intermediate 1-7(a), and stirred while refluxing for 5 hours. The resultant was cooled to room temperature, extracted by using MC, and washed by using distilled water. The resultant was dried by using MgSO$_4$ and distilled under reduced pressure, and the residue was separated by a column chromatography, to thereby obtain Compound 1-7. (yield of 77.64%)

$C_{48}H_{29}D_5N_2Si$ [M]+: calculation: 671.93, measurement: 670

Elemental Analysis Calculated: C, 85.80; H, 5.85; N, 4.17; Si, 4.18

Synthesis Example 4: Synthesis of Compound 1-8

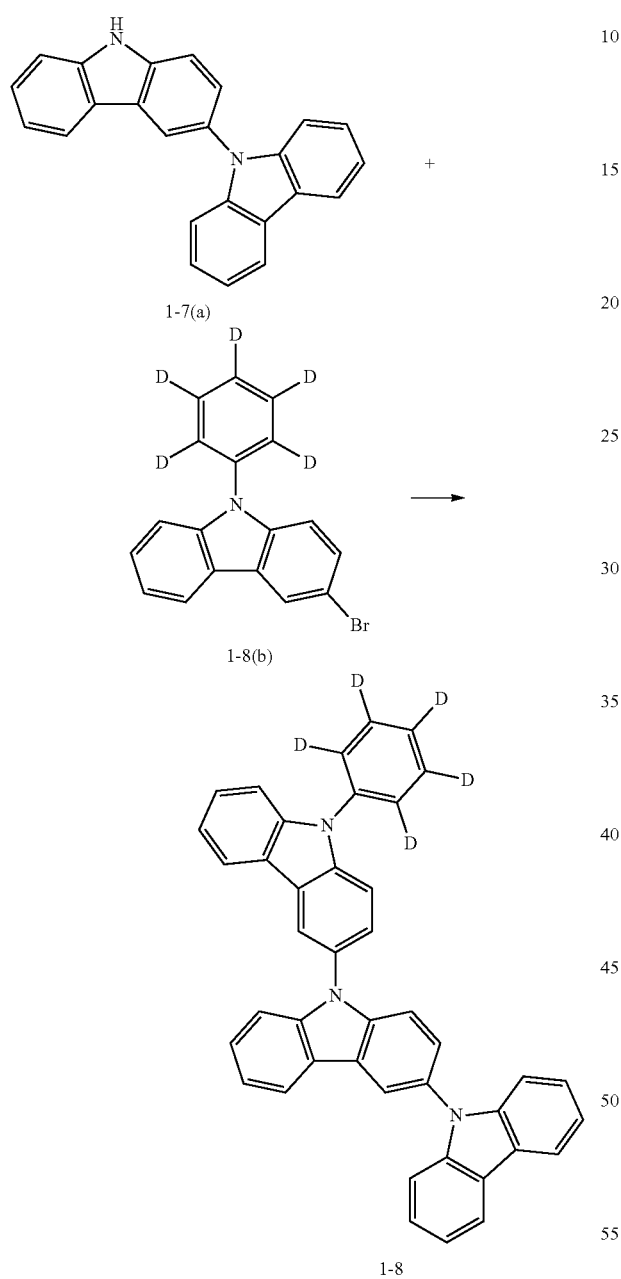

Pd(dba)₃ (0.03 eq), (t-Bu)₃P (0.06 eq), and toluene (0.1 M based on 1 eq of reagent) were added into a flask containing 1 eq of Intermediate 1-8(b) and 1.1 eq of Intermediate 1-7(a), and stirred while refluxing for 5 hours. The resultant was cooled to room temperature, extracted by using MC, and washed by using distilled water. The resultant was dried by using MgSO₄ and distilled under reduced pressure, and the residue was separated by a column chromatography, to thereby obtain Compound 1-8. (yield of 79.11%)

$C_{42}H_{22}D_5N_3$ [M]+: calculation: 578.73, measurement: 577

Elemental Analysis Calculated: C, 87.17; H, 5.57; N, 7.26

Synthesis Example 5: Synthesis of Compound 2-1

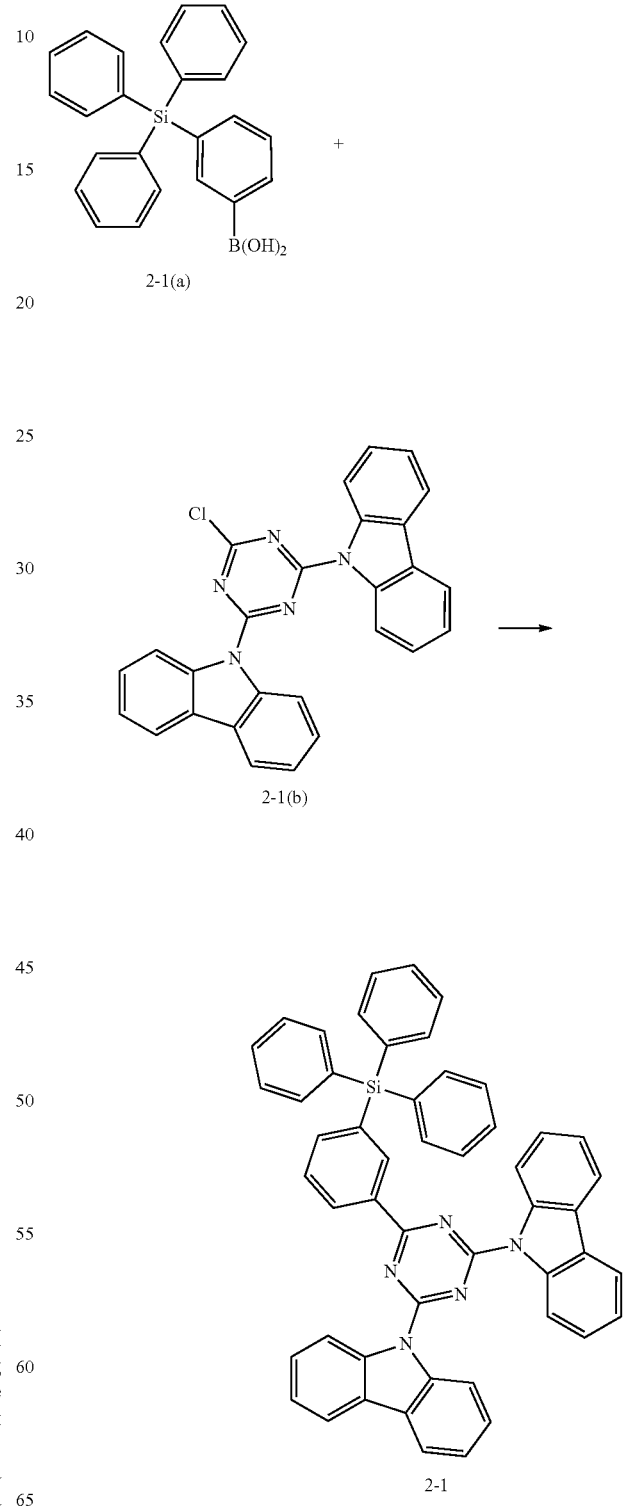

Synthesis of Intermediate 2-1 (a)

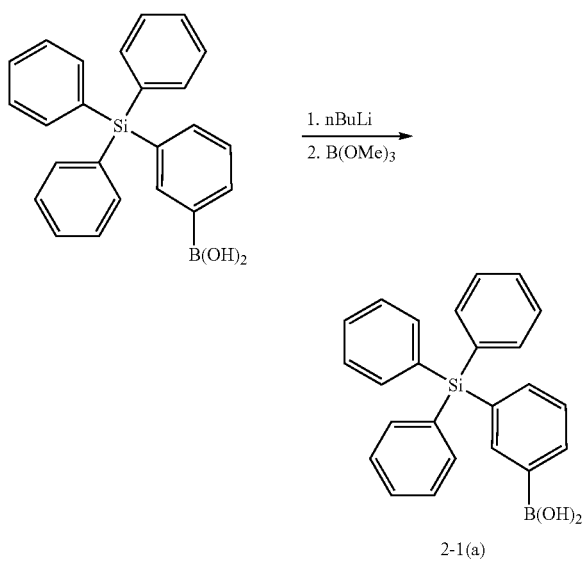

(3-bromophenyl)triphenylsilane (1 eq) was added into an RBF, and THF (150 mL) was added thereto. nBuLi (2 M in hexane, 17 mL. 1.2 eq) was slowly added dropwise thereto at −78° C. After 40 minutes, trimethyl borate (5.75 mL, 1.5 eq) was slowly added dropwise thereto. The temperature was slowly raised to room temperature, and the resultant was stirred overnight. The resultant was subjected to quenching by using water and NH$_4$Cl solution. The resultant was washed by using EA/H$_2$O. The resultant was dried by using MgSO$_4$ and subjected to a column chromatography using MC and EA, to thereby obtain Intermediate 2-1 (a). (yield of 77%)

$C_{24}H_{21}BO_2Si$ [M]+: calculation: 380.33, measurement: 379

Synthesis of Intermediate 2-1 (b)

Carbazole (2 eq) was put into an RBF, and THF was added thereto. At room temperature, nBuLi (2 M in hexane, 1.9 eq) was slowly added dropwise thereto and stirred for 30 minutes. 2,4,6-trichlorotriazine (1 eq) was put into an RBF, and THF was added thereto. Prepared Li-Carbazole solution was slowly added dropwise thereto for 30 minutes by using a dropping funnel. The reacting solution was refluxed for 2 hours and cooled to room temperature. Water was added dropwise thereto to carry out quenching and stirred for 30 minutes. A solid generated therefrom was subjected to filtration, and the solid was washed by using distilled water, methanol, and hexane, to thereby obtain Intermediate 2-1 (b). (yield of 84%)

$C_{27}H_{16}ClN_5$ [M]+: calculation: 445.91, measurement: 444

Synthesis of Compound 2-1

Intermediate 2-1 (b) (1 eq), Intermediate 2-1 (a) (1.1 eq), Pd(PPh$_3$)$_4$ (0.05 eq), K$_2$CO$_3$ (2.5 eq), THF (400 mL), and H$_2$O (100 mL) were put into an RBF, and stirred overnight while refluxing at 100° C. After completion of the reaction, EA/H$_2$O were added thereto and stirred for 30 minutes. Only the organic layer was separated out by using a separatory funnel. The resultant was dried by using MgSO$_4$ and subjected to a silica filtration using MC, and a solid generated therefrom was subjected to filtration by using MeOH and dried. The dried solid was dissolved by boiling in toluene (100 mL), and ether and hexane at a volume ratio of 1:1(100 mL) were added dropwise thereto for solidification. Again, the solid was dissolved in MC (400 mL), and hexane (400 mL) was added thereto to slowly recrystallize the solid, to thereby obtain Compound 2-1. (yield of 84.1%)

$C_{51}H_{35}N_5Si$ [M]+: calculation: 745.96, measurement: 744

Elemental Analysis Calculated: C, 82.12; H, 4.73; N, 9.39; Si, 3.76

Synthesis Example 6: Synthesis of Compound 2-2

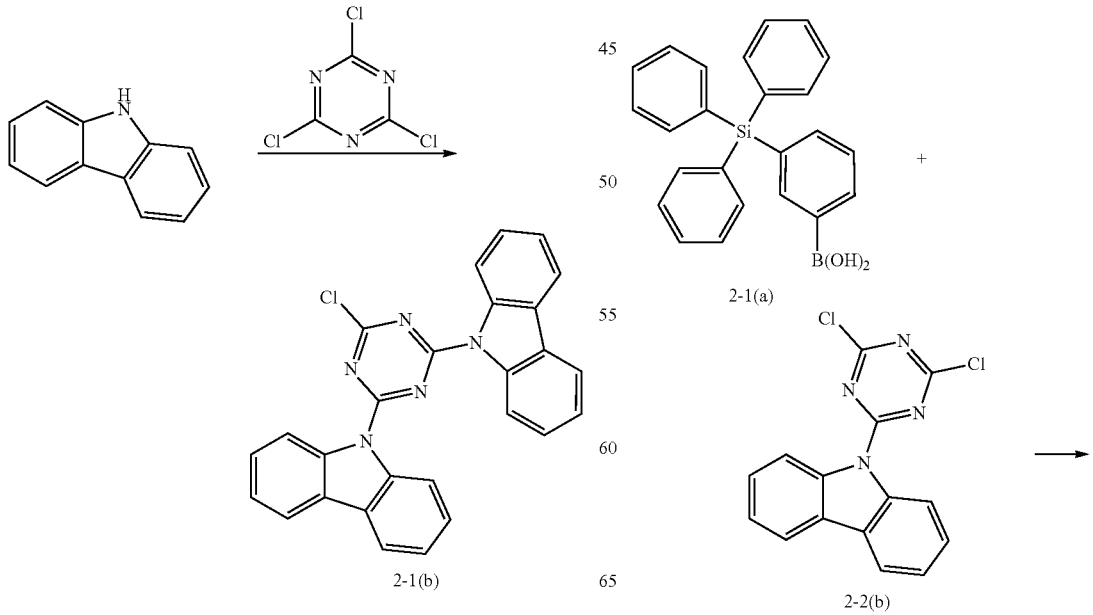

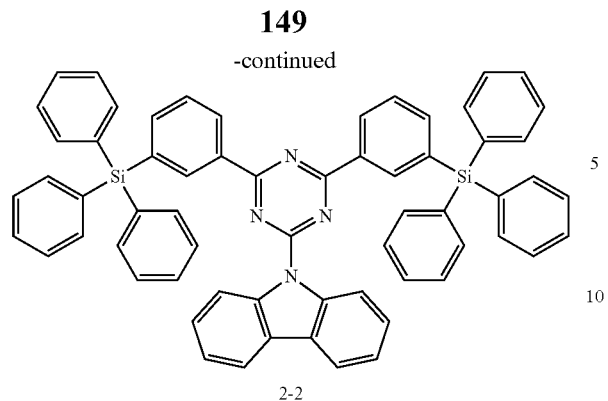

2-2

Synthesis of Intermediate 2-2(b)

Intermediate 2-2(b) was obtained in the same manner as used in the synthesis method of Intermediate 2-1 (b), except that carbazole was adjusted to 1 eq from 2 eq in an RBF. (yield of 71%)

$C_{15}H_8Cl_2N_4$ [M]+: calculation: 315.16, measurement: 314

Synthesis of Compound 2-2

Compound 2-2 was obtained in the same manner as used in the synthesis method of Compound 2-1, except that Intermediate 2-2(b) was used instead of Intermediate 2-1 (b), and an equivalent (eq) of Intermediate 2-1 (a) was 2.2 eq rather than 1.1 eq. (yield of 79%)

$C_{63}H_{46}N_4Si_2$ [M]+: calculation: 915.26, measurement: 914

Elemental Analysis Calculated: C, 82.68; H, 5.07; N, 6.12; Si, 6.14

Compounds other than the compounds synthesized in Synthesis Examples 1 to 6 may be easily recognized by those skilled in the art by referring to the above synthesis routes and source materials.

Example 1

As an anode, an ITO/Ag/ITO substrate (hereinafter, referred to as "ITO substrate") was cut to a size of 50 mm×50 mm×0.5 mm, sonicated by using isopropyl alcohol and pure water for 10 minutes each, and, cleaned by irradiation of ultraviolet rays and exposure of zone thereto for 10 minutes. The ITO substrate was loaded onto a vacuum deposition apparatus.

m-MTDATA was vacuum-deposited on the ITO substrate to form a hole injection layer having a thickness of 4 nm, and NPB was vacuum-deposited on the hole injection layer to form a hole transport layer having a thickness of 1 nm.

Compound 1-1 (host 1), Compound 2-1 (host 2), and Compound 3-1 (dopant) were co-deposited on the hole transport layer at a weight ratio of 6:3:1 to form an emission layer having a thickness of 40 nm. Subsequently, BAlq was vacuum-deposited thereon to form a hole blocking layer having a thickness of 10 nm. Subsequently, ET1 was deposited on the hole blocking layer to form an electron transport layer having a thickness of 30 nm, LiF, which is an alkali metal halide, was deposited on the electron transport layer to form an electron injection layer having a thickness of 1 nm, and Al was vacuum-deposited thereon to form an LiF/Al cathode having a thickness of 120 nm, thereby completing manufacture of a light-emitting device.

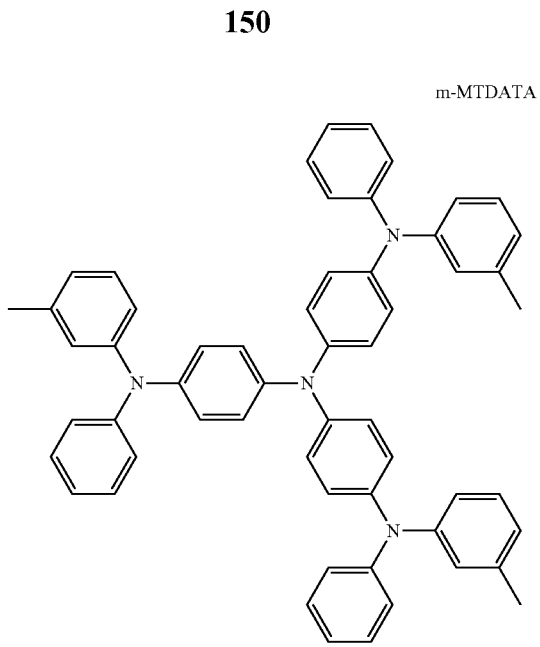

m-MTDATA

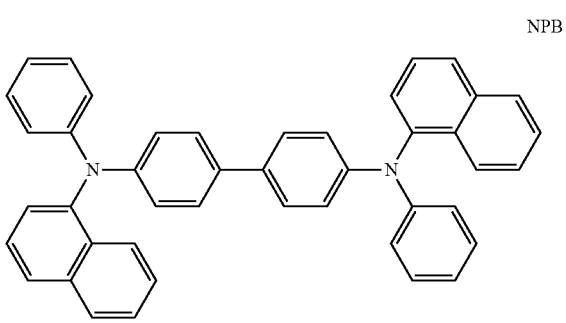

NPB

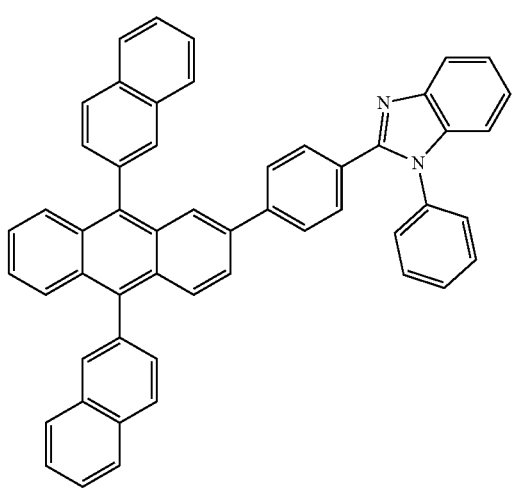

ET1

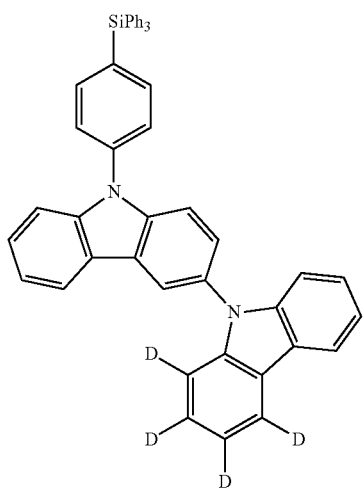

1-1

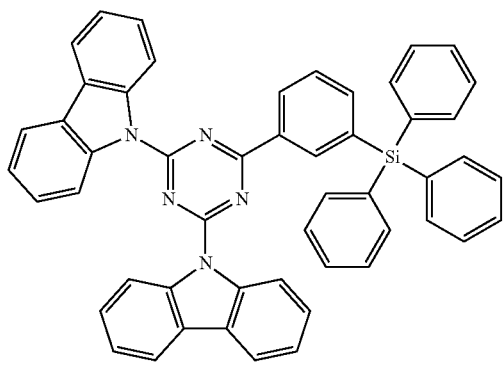

2-1

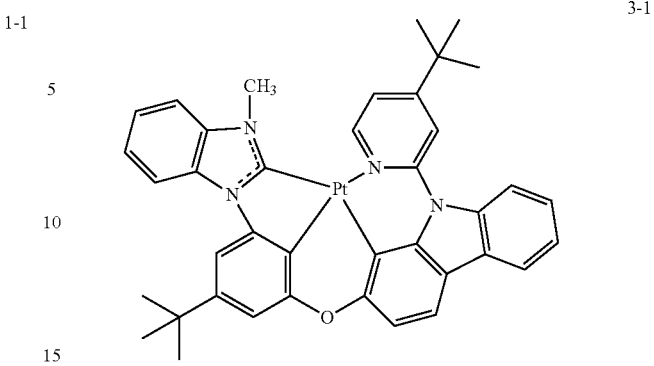

3-1

Examples 2 to 10 and Comparative Examples 1 and 2

A light-emitting device was manufactured in the same manner as in Example 1, except that, compounds shown in Table 2 was used instead of Compounds 1-1, 2-1, and 3-1, which were used in Example 1, in forming an emission layer. In cases of Comparative Examples 1 and 2, host (CBP) and dopant (Compound 3-1 or 3-2) were co-deposited at a weight ratio of 9:1.

Evaluation Example 1

In order to evaluate characteristics of the light-emitting devices manufactured in Examples 1 to 10 and Comparative Examples 1 and 2, with respect to the light-emitting devices, light emission efficiency (cd/A) at 1000 cd/m$^2$, lifespan ($T_{90}$), and an emission color were each measured by using Keithley MU 236 and a luminance meter PR650, and results thereof are shown in Table 1. In Table 1, the lifespan ($T_{90}$) is a measure of the time taken when the luminance reaches 90% of the initial luminance.

TABLE 1

|  | Host 1 | Host 2 | Dopant | Light emission efficiency (cd/A) | Lifespan ($T_{90}$, h) |
|---|---|---|---|---|---|
| Example 1 | Compound 1-1 | Compound 2-1 | Compound 3-1 | 16.9 | 110 |
| Example 2 | Compound 1-1 | Compound 2-2 | Compound 3-1 | 18.6 | 86 |
| Example 3 | Compound 1-1 | Compound 2-1 | Compound 3-3 | 13.0 | 70 |
| Example 4 | Compound 1-2 | Compound 2-1 | Compound 3-1 | 18.2 | 112 |
| Example 5 | Compound 1-2 | Compound 2-2 | Compound 3-1 | 18.5 | 113 |
| Example 6 | Compound 1-2 | Compound 2-1 | Compound 3-3 | 14.2 | 90 |
| Example 7 | Compound 1-5 | Compound 2-1 | Compound 3-3 | 14.8 | 95 |
| Example 8 | Compound 1-7 | Compound 2-1 | Compound 3-3 | 14.0 | 102 |
| Example 9 | Compound 1-8 | Compound 2-1 | Compound 3-3 | 13.8 | 105 |
| Example 10 | Compound 1-8 | Compound 2-2 | Compound 3-3 | 13.5 | 89 |
| Comparative Example 1 | CBP | — | Compound 3-1 | 13.6 | 20 |
| Comparative Example 2 | CBP | — | Compound 3-3 | 10.1 | 16 |

1-1 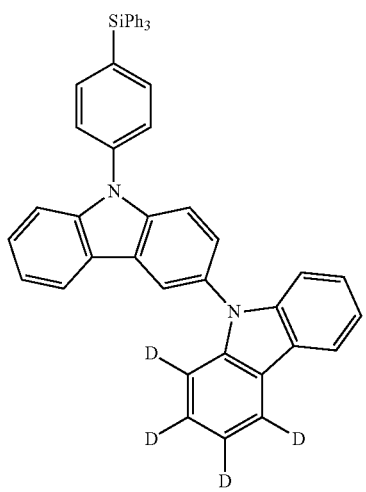
1-2 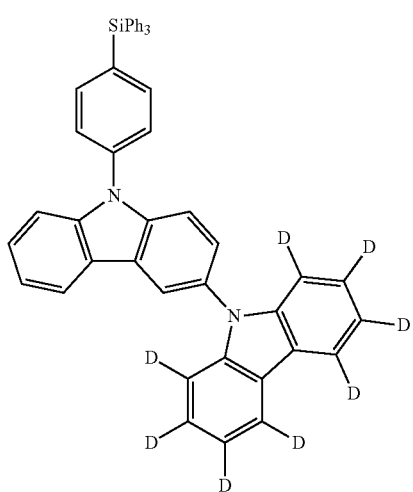
1-5 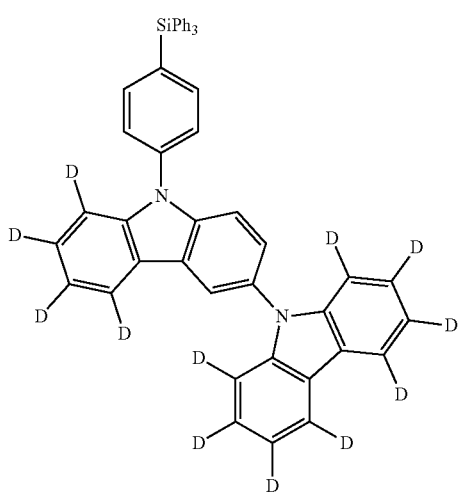
1-7 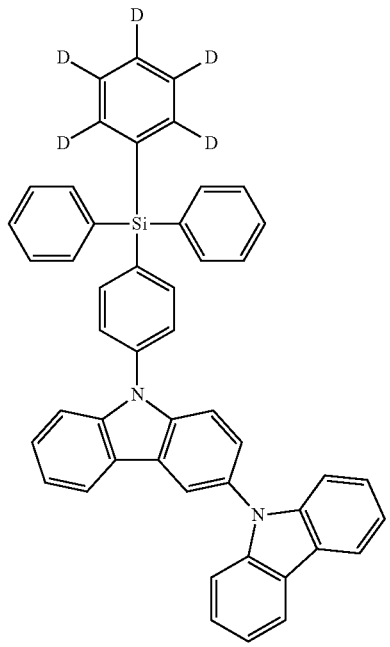
1-8 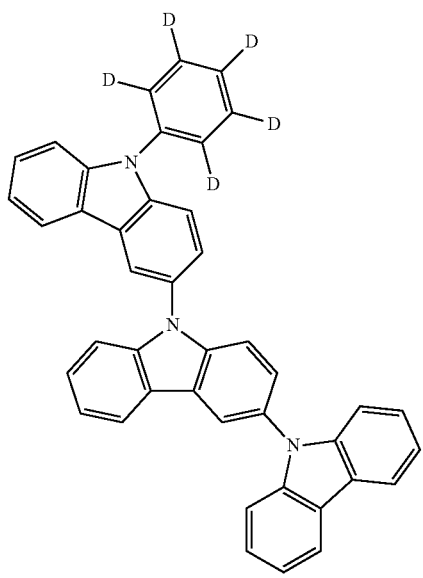
2-1 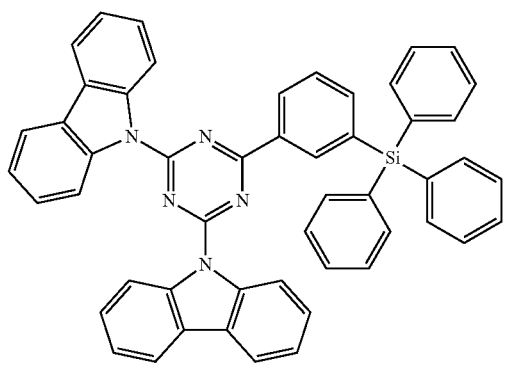

-continued 2-2
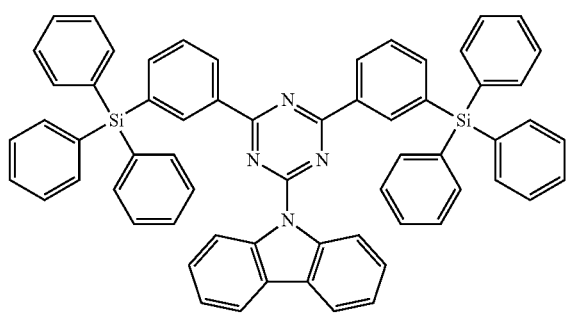

3-1
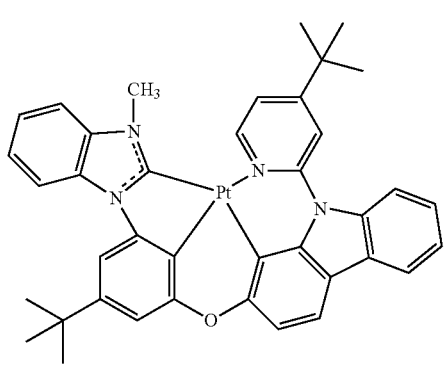

3-3
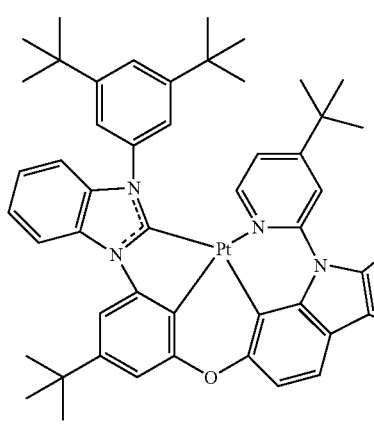

CBP
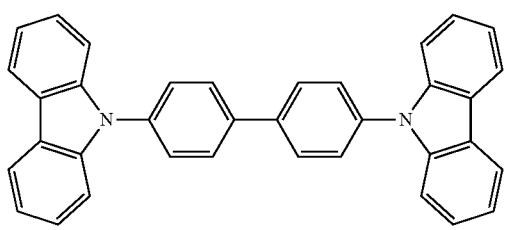

From Table 1, it can be seen that the light-emitting devices of Examples 1 to 10 have higher efficiency or a longer lifespan than the light-emitting devices of Comparative Examples 1 and 2.

The light-emitting device may have high efficiency and long lifespan and may be used to manufacture high-quality electronic apparatuses having excellent light emission efficiency and long lifespan.

It should be understood that embodiments described herein should be considered in a descriptive sense only and not for purposes of limitation. Descriptions of features or aspects within each embodiment should typically be considered as available for other similar features or aspects in other embodiments. While embodiments have been described with reference to the figures, it will be understood by those of ordinary skill in the art that various changes in form and details may be made therein without departing from the spirit and scope as defined by the claims.

What is claimed is:

1. A light-emitting device comprising:
   a first electrode;
   a second electrode facing the first electrode; and
   an interlayer disposed between the first electrode and the second electrode and including an emission layer, wherein
   the interlayer includes:
      a first compound represented by Formula 1;
      a second compound selected from one of Compounds 2-1 to 2-24; and
      a third compound, and
      the third compound is a blue phosphorescent compound:

[Formula 1]
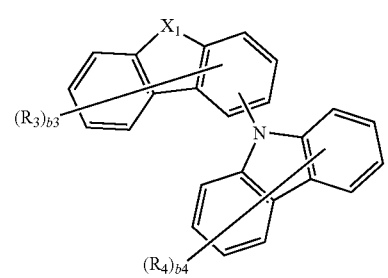

2-1
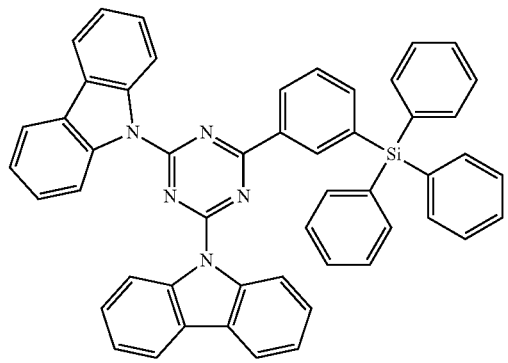

2-2
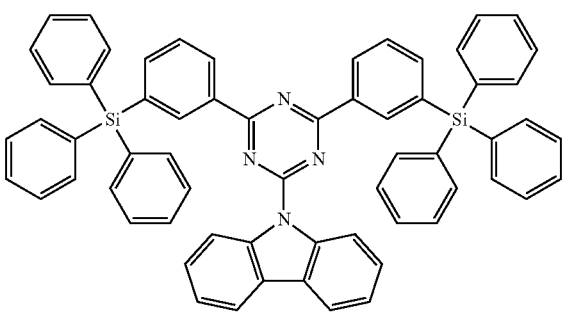

-continued
2-3
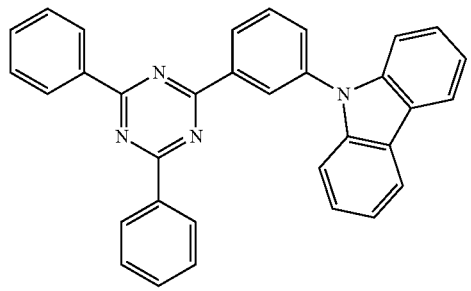
2-4
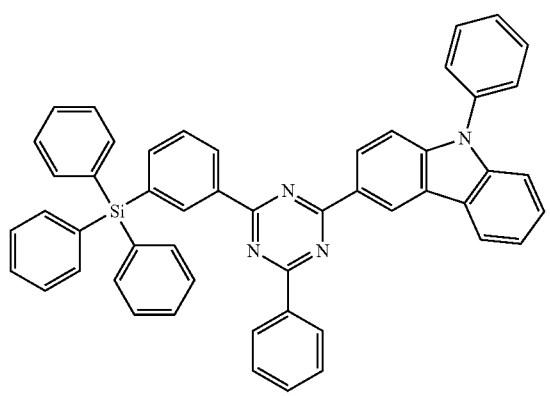
2-5
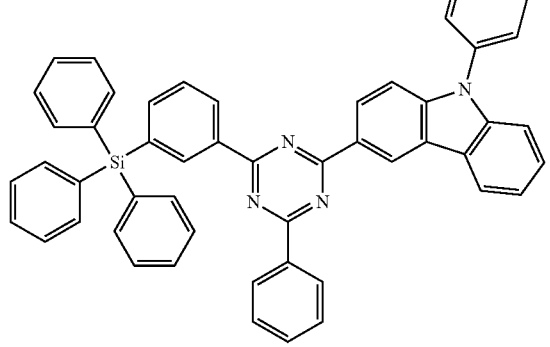
2-6
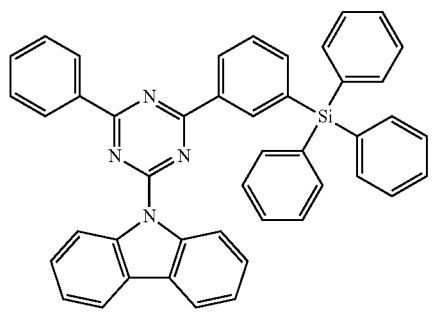
-continued
2-7
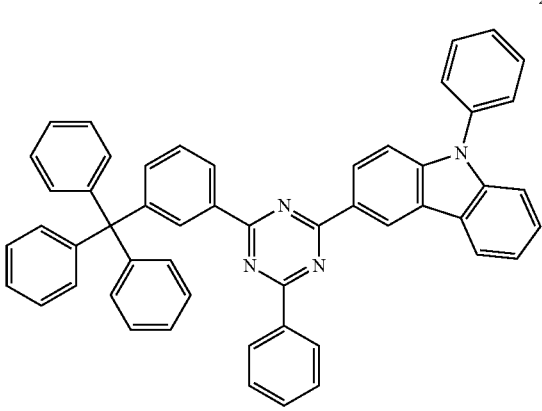
2-8
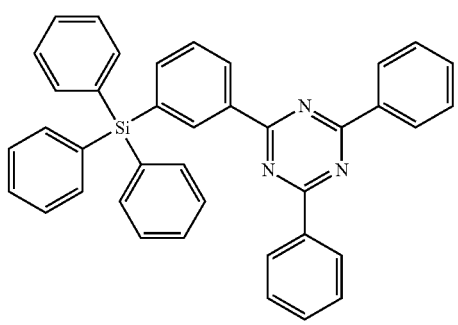
2-9
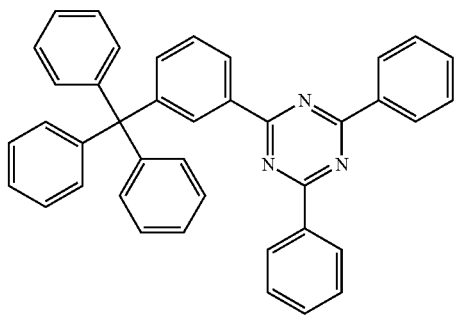
2-10
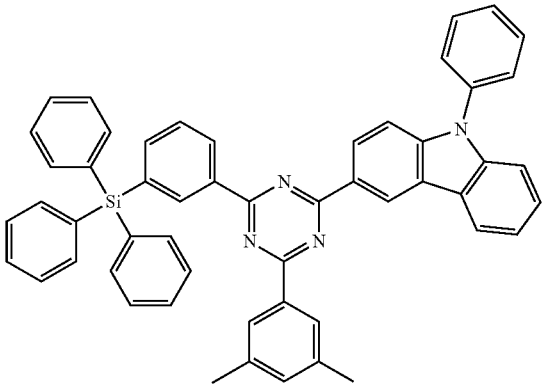

-continued
2-11
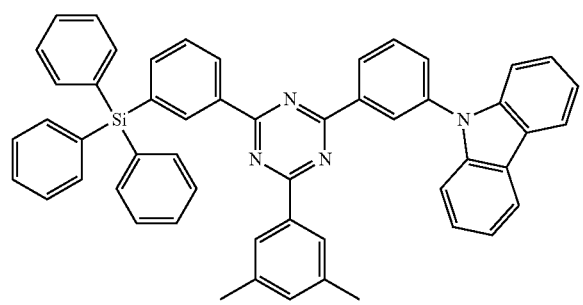
2-15
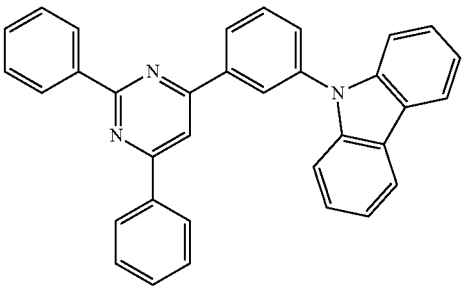
2-12
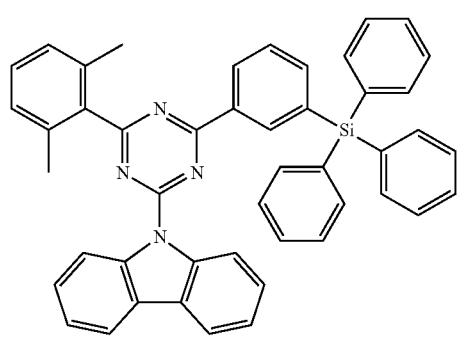
2-16
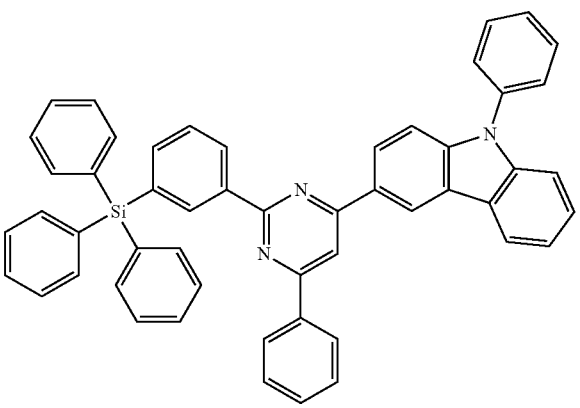
2-13
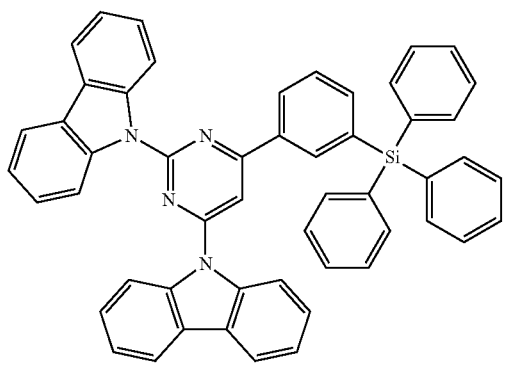
2-17
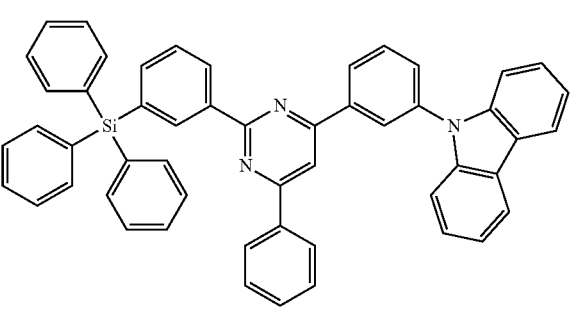
2-14
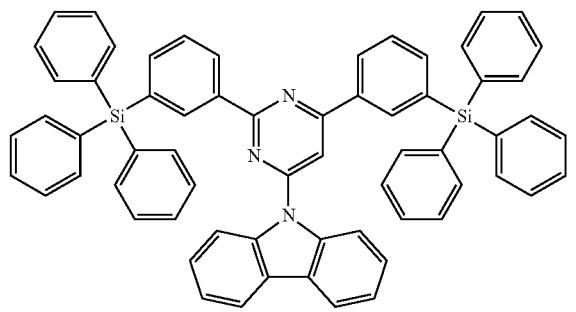
2-18
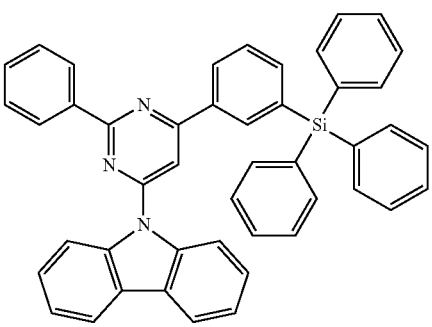

-continued 2-19
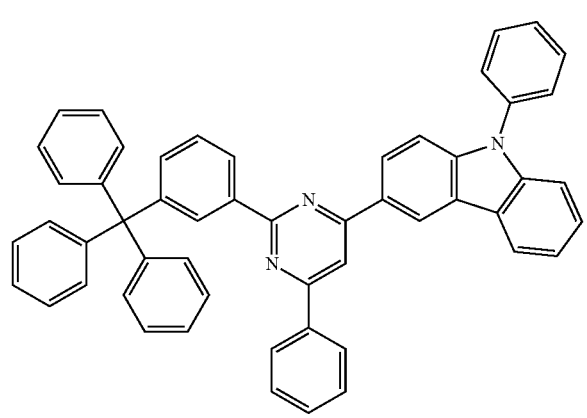

2-20
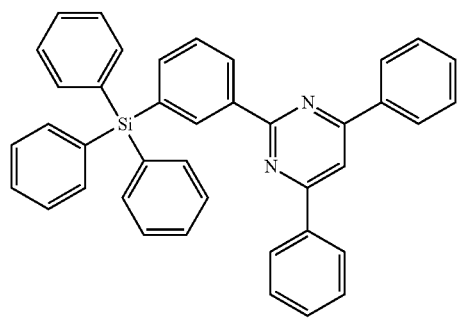

2-21
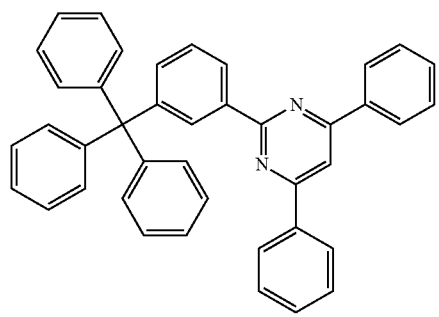

2-22
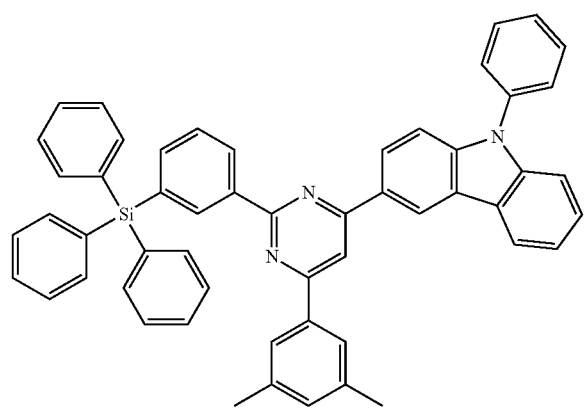

2-23
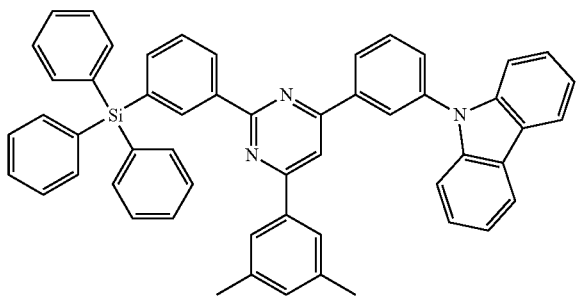

2-24
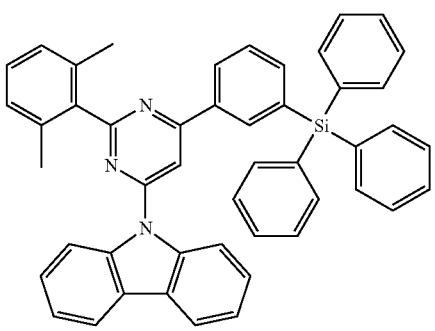

wherein in Formula 1, $X_1$ is $C(R_1)(R_2)$, $Si(R_1)(R_2)$, $N-[(L_1)_{a1}-(R_1)_{b1}]$, O, or S, $L_1$ is a $C_4$-$C_{60}$ carbocyclic group unsubstituted or substituted with at least one $R_{10a}$ or a $C_1$-$C_{60}$ heterocyclic group unsubstituted or substituted with at least one $R_{10a}$, a1 is an integer from 0 to 5, $R_1$ to $R_4$ are each independently hydrogen, deuterium, —F, —Cl, —Br, —I, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, —B $(Q_1)(Q_2)$, —P $(Q_1)(Q_2)$, —C(=O) $(Q_1)$, or —Si$(Q_1)(Q_2)(Q_3)$, b1 is an integer from 0 to 10, b3 is an integer from 0 to 7, b4 is an integer from 0 to 8, and the first compound includes at least one deuterium (D), and $R_{10a}$ is:

deuterium (-D), —F, —Cl, —Br, —I, a hydroxyl group, a cyano group, or a nitro group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each unsubstituted or substituted with deuterium, —F, —Cl, —Br, —I, a hydroxyl group, a cyano group, a nitro group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, —C$(Q_{11})(Q_{12})(Q_{13})$, —Si $(Q_{11})(Q_{12})(Q_{13})$, —N$(Q_{11})$ $(Q_{12})$, —B$(Q_{11})(Q_{12})$, —C(=O) $(Q_{11})$, —S(=O)$_2$ $(Q_{11})$, —P(=O)$(Q_{11})(Q_{12})$, or a combination thereof;

a C₃-C₆₀ carbocyclic group, a C₁-C₆₀ heterocyclic group, a C₆-C₆₀ aryloxy group, or a C₆-C₆₀ arylthio group, each unsubstituted or substituted with deuterium, —F, —C₁, —Br, —I, a hydroxyl group, a cyano group, a nitro group, a C₁-C₆₀ alkyl group, a C₂-C₆₀ alkenyl group, a C₂-C₆₀ alkynyl group, a C₁-C₆₀ alkoxy group, a C₃-C₆₀ carbocyclic group, a C₁-C₆₀ heterocyclic group, a C₆-C₆₀ aryloxy group, a C₆-C₆₀ arylthio group, —C(Q₂₁)(Q₂₂)(Q₂₃), —Si(Q₂₁)(Q₂₂)(Q₂₃), —N(Q₂₁)(Q₂₂), —B(Q₂₁)(Q₂₂), —C(=O) (Q₂₁), —S(=O)₂(Q₂₁), —P(=O) (Q₂₁)(Q₂₂), or a combination thereof, or —C(Q₃₁)(Q₃₂)(Q₃₃), —Si(Q₃₁)(Q₃₂)(Q₃₃), —N(Q₃₁)(Q₃₂), —B(Q₃₁)(Q₃₂), —C(=O) (Q₃₁), —S(=O)₂(Q₃₁), or —P(=O) (Q₃₁)(Q₃₂), and Q₁ to Q₃, Q₁₁ to Q₁₃, Q₂₁ to Q₂₃, and Q₃₁ to Q₃₃ are each independently: hydrogen; deuterium; —F; —C₁; —Br; —I; a hydroxyl group; a cyano group; a nitro group; a C₁-C₆₀ alkyl group; a C₂-C₆₀ alkenyl group; a C₂-C₆₀ alkynyl group; a C₁-C₆₀ alkoxy group; or a C₃-C₆₀ carbocyclic group or a C₁-C₆₀ heterocyclic group, each unsubstituted or substituted with deuterium, —F, a cyano group, a C₁-C₆₀ alkyl group, a C₁-C₆₀ alkoxy group, a phenyl group, a biphenyl group, or a combination thereof.

2. The light-emitting device of claim 1, wherein L₁ in Formula 1 is a π electron-rich C₃-C₆₀ cyclic group unsubstituted or substituted with at least one R₁₀ₐ.

3. The light-emitting device of claim 1, wherein R₁ to R₄ in Formula 1 are each independently:

hydrogen, deuterium, —F, —C₁, —Br, —I, a hydroxyl group, a cyano group, or a nitro group;

a C₁-C₂₀ alkyl group, a C₂-C₂₀ alkenyl group, a C₂-C₂₀ alkynyl group, or a C₁-C₂₀ alkoxy group, each unsubstituted or substituted with deuterium, —F, —C₁, —Br, —I, —CD₃, —CD₂H, —CDH₂, —CF₃, —CF₂H, —CFH₂, a hydroxyl group, a cyano group, a nitro group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, —Si(Q₃₁)(Q₃₂)(Q₃₃), —N(Q₃₁)(Q₃₂), —B(Q₃₁)(Q₃₂), —C(=O) (Q₃₁), —S(=O)₂(Q₃₁), —P(=O) (Q₃₁)(Q₃₂), or a combination thereof; or a π electron-rich C₃-C₆₀ cyclic group unsubstituted or substituted with at least one R₁₀ₐ.

4. The light-emitting device of claim 1, wherein the first compound is represented by one of Formulae 1(1) to 1(4):

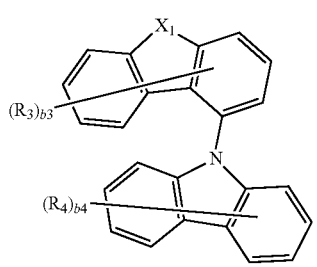

1(1)

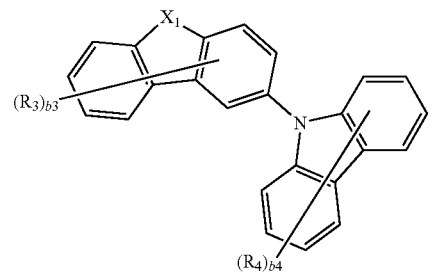

1(2)

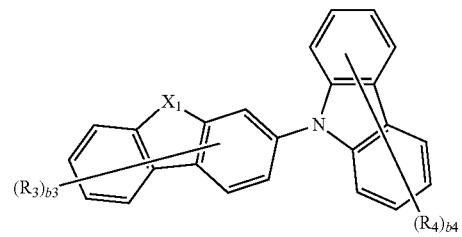

1(3)

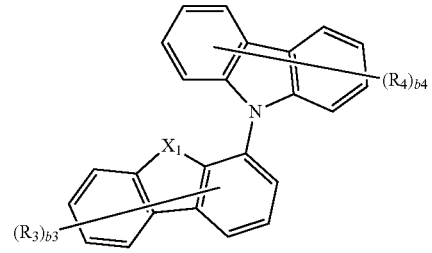

1(4)

wherein in Formulae 1(1) to 1(4),

X₁, R₃, R₄, b3, and b4 are the same as described in connection with Formula 1.

5. The light-emitting device of claim 1, wherein the first compound is selected from one of Compounds 1-1 to 1-9:

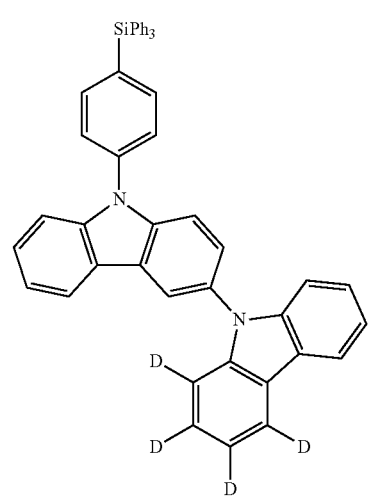

1-1

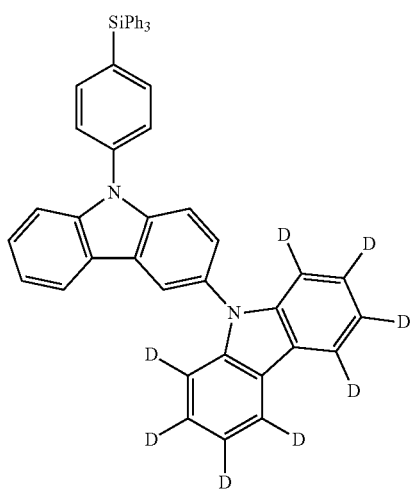
1-2
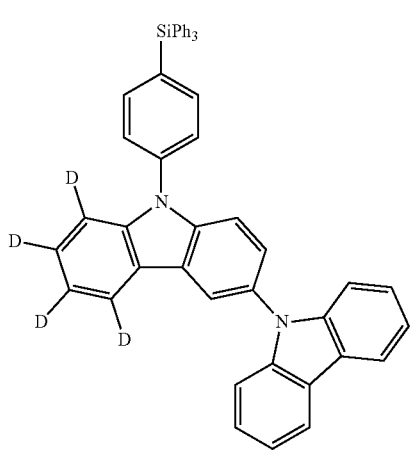
1-3
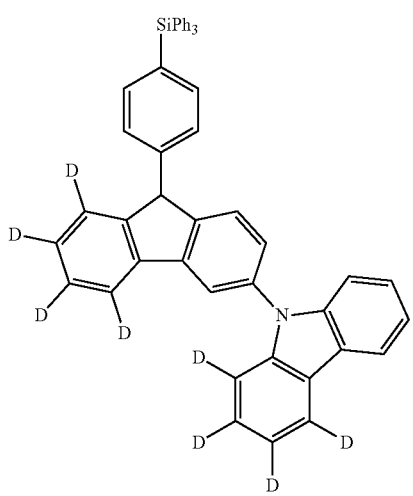
1-4
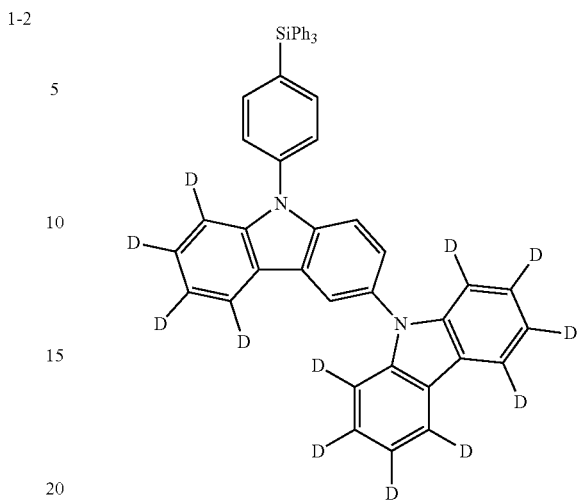
1-5
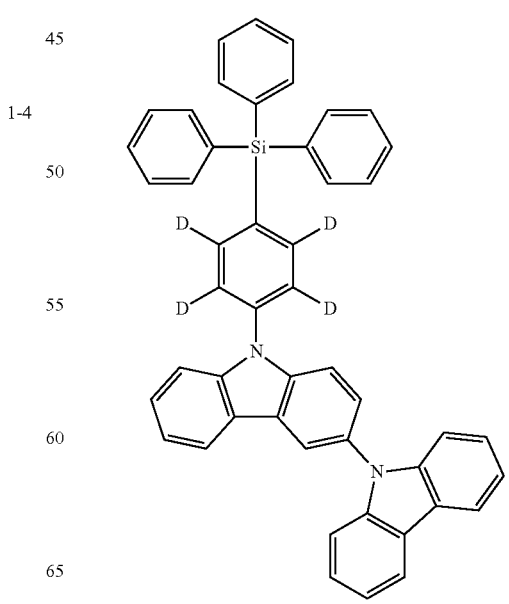
1-6

1-7
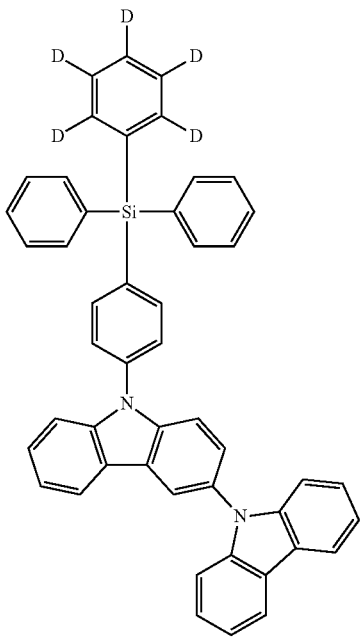

1-8

1-9
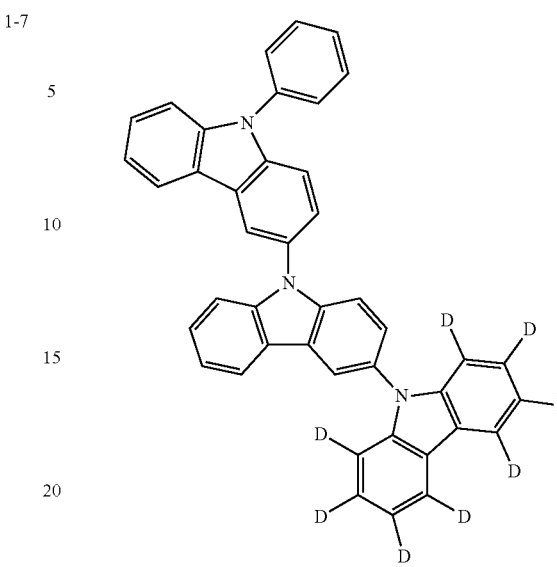

wherein Ph represents a phenyl group.

6. The light-emitting device of claim 1, wherein the third compound is a platinum (Pt) complex including a tetradentate ligand.

7. The light-emitting device of claim 1, wherein the third compound includes a carbene moiety in which carbon and Pt are bonded.

8. The light-emitting device of claim 1, wherein the third compound is represented by Formula 3:

[Formula 3]

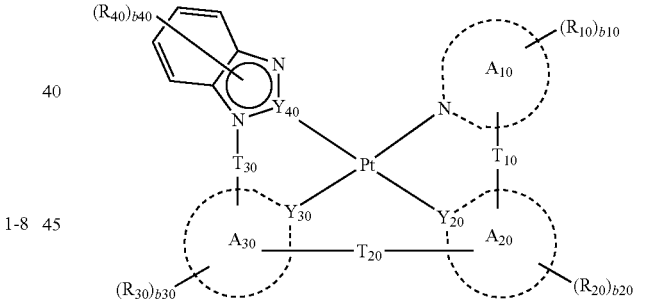

wherein in Formula 3, $Y_{20}$, $Y_{30}$, and $Y_{40}$ are each independently C or N, $T_{10}$ to $T_{30}$ are each independently selected from a single bond, *—O—*', *—S—*', *—C($Z_{10a}$)($Z_{10b}$)—*', *—C($Z_{10a}$)=*', *—C($Z_{10a}$)=C($Z_{10b}$)—*', *—C(=O)—*', *—C(=S)—*', *—C≡C—*', *—B($Z_{10a}$)—*', *—N($Z_{10a}$)—*', *—P($Z_{10a}$)—*', and *—Si($Z_{10a}$)($Z_{10b}$)—*', $A_{10}$, $A_{20}$, and $A_{30}$ are each independently a $C_4$-$C_{60}$ carbocyclic group or a $C_1$-$C_{60}$ heterocyclic group, $R_{10}$, $R_{20}$, $R_{30}$, and $R_{40}$ are each independently the same as described in connection with $R_1$ in Formula 1, $Z_{10a}$ and $Z_{10b}$ are each independently the same as defined in connection with $R_1$ in Formula 1, b10, b20, and b30 are each independently an integer from 0 to 10, b40 is an integer from 0 to 5, and and *' each indicate a binding site to a neighboring atom.

9. The light-emitting device of claim 8, wherein $Y_{40}$ is C, and a bond between $Y_{40}$ and Pt is a coordinate bond.

10. The light-emitting device of claim 8, wherein $T_{10}$ and $T_{30}$ are single bonds, and $T_{20}$ is not a single bond.

11. The light-emitting device of claim 8, wherein Formula 3 satisfies at least one of three conditions:

(i) $A_{10}$ is a pyridine group, (ii) $A_{20}$ is a carbazole group, and/or (iii) $A_{30}$ is a benzene group.

12. The light-emitting device of claim 8, wherein the third compound is represented by one of Formulae 3(1) and 3(2):

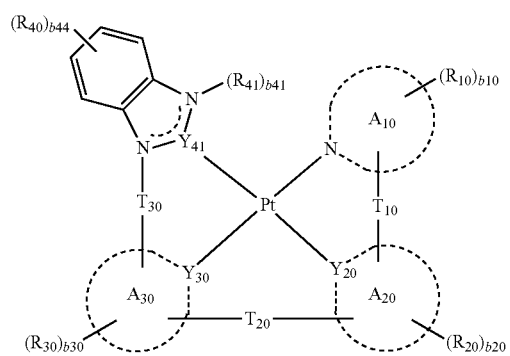

3(1)

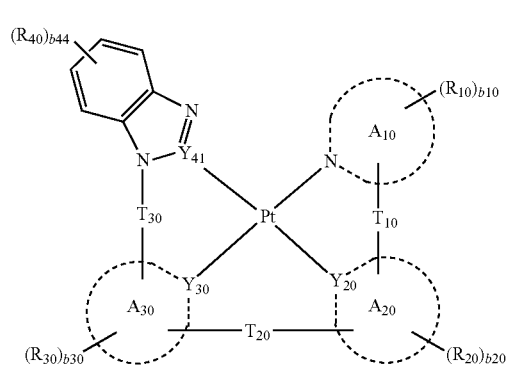

3(2)

wherein in Formulae 3(1) and 3(2), $Y_{20}$, $Y_{30}$, $T_{10}$, $T_{20}$, $T_{30}$, $A_{10}$, $A_{20}$, $A_{30}$, $R_{10}$, $R_{20}$, $R_{30}$, $R_{40}$, b10, b20, and b30 are the same as described in connection with Formula 3, $Y_{41}$ is C, $R_{41}$ is the same as described in connection with $R_{40}$ in Formula 3, b41 is 1, and b44 is an integer from 0 to 4.

13. The light-emitting device of claim 1, wherein the third compound is selected from one of Compounds 3-1 to 3-4:

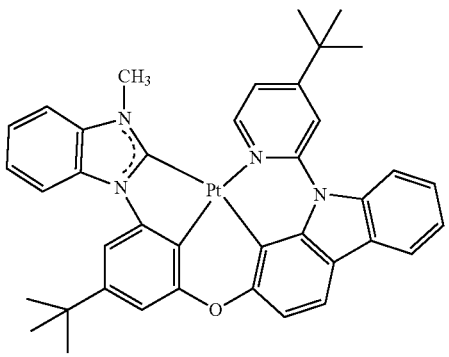

3-1

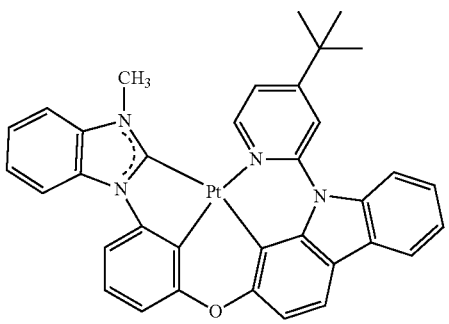

3-2

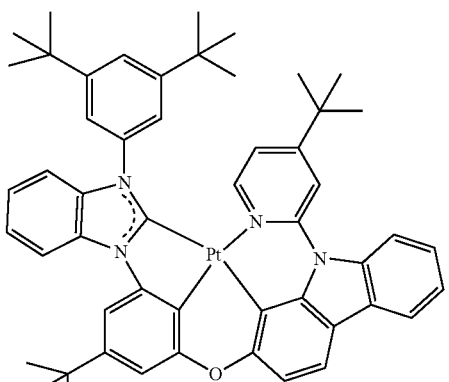

3-3

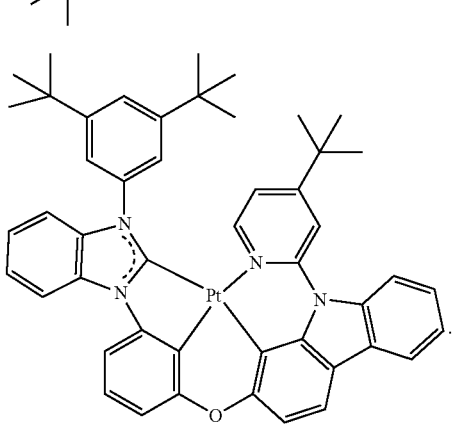

3-4

14. The light-emitting device of claim 1, wherein the light-emitting device emits blue light having a maximum luminescence wavelength in a range of about 400 nm to about 500 nm, and the emission layer has a difference of equal to or less than about 0.5 eV between a singlet energy level and a triplet energy level.

15. The light-emitting device of claim 1, further comprising a capping layer disposed outside the second electrode,
   wherein the capping layer includes a carbocyclic compound, a heterocyclic compound, an amine group-containing compound, a porphyrine derivative, a phthalocyanine derivative, a naphthalocyanine derivative, an alkali metal complex, an alkaline earth-metal complex, or a combination thereof.

16. An electronic apparatus comprising the light-emitting device of claim 1 and further comprising a thin-film transistor,
   wherein the thin-film transistor comprises a source electrode and a drain electrode, and
   the first electrode of the light-emitting device is electrically connected to the source electrode or the drain electrode.

17. The electronic apparatus of claim 16, further comprising an encapsulation portion,
   wherein the encapsulation portion comprises an organic layer, an inorganic layer, or a combination thereof.

18. The electronic apparatus of claim 16, further comprising a color filter, a color conversion layer, a touch screen layer, a polarizing layer, or a combination thereof.

\* \* \* \* \*